US012751956B2

(12) United States Patent
Corti et al.

(10) Patent No.: US 12,751,956 B2
(45) Date of Patent: Oct. 6, 2026

(54) COMBINATION THERAPY OF PD-1 AXIS BINDING ANTAGONISTS AND LRRK2 INHITIBORS

(71) Applicant: Hoffmann-La Roche Inc., Little Falls, NJ (US)

(72) Inventors: Denise Corti, Regensdorf (CH); Stephan Gasser, Fislisbach (CH); Gabor Gyulveszi, Schlieren (CH); Claudio Murgia, Baden (CH); Tobias Schmidt, Zurich (CH); Martha Liliana Serrano Serrano, Ormalingen (CH); Pablo Umaña, Wollerau (CH)

(73) Assignee: Hoffmann-La Roche Inc., Branchburg, NJ (US)

( * ) Notice: Subject to any disclaimer, the term of this patent is extended or adjusted under 35 U.S.C. 154(b) by 509 days.

(21) Appl. No.: 18/303,802

(22) Filed: Apr. 20, 2023

(65) Prior Publication Data

US 2024/0100063 A1 Mar. 28, 2024

Related U.S. Application Data

(63) Continuation of application No. PCT/EP2021/078732, filed on Oct. 18, 2021.

(30) Foreign Application Priority Data

Oct. 20, 2020 (EP) .................................... 20202857

(51) Int. Cl.
*A61K 31/551* (2006.01)
*A61K 31/506* (2006.01)
(Continued)

(52) U.S. Cl.
CPC .......... *A61K 31/551* (2013.01); *A61K 31/506* (2013.01); *A61K 31/5377* (2013.01); *C07K 16/2827* (2013.01); *A61K 2039/505* (2013.01)

(58) Field of Classification Search
CPC ................ A61K 31/551; A61K 31/506; A61K 31/5377; A61K 2039/505; A61K 45/06;
(Continued)

(56) References Cited

U.S. PATENT DOCUMENTS

2014/0005183 A1 1/2014 Galatsis et al.

FOREIGN PATENT DOCUMENTS

JP 2016514097 5/2019
WO 2010/077634 A1 7/2010
(Continued)

OTHER PUBLICATIONS

Ahmadzadeh, M., et al., "Tumor antigen-specific CD8 T cells infiltrating the tumor express high levels of PD-1 and are functionally impaired" Blood 114(8):1537-1544 (Aug. 20, 2009).
(Continued)

*Primary Examiner* — Kamal A Saeed
*Assistant Examiner* — Meghan C Heasley
(74) *Attorney, Agent, or Firm* — Roberto K. Rodriguez

(57) ABSTRACT

The present invention relates to combination therapies employing PD-1 axis binding antagonists and LRRK2 inhibitors and, and the use of these combination therapies for the treatment of cancer.

1 Claim, 23 Drawing Sheets

Specification includes a Sequence Listing.

(51) Int. Cl.
*A61K 31/5377* (2006.01)
*A61K 39/00* (2006.01)
*C07K 16/28* (2006.01)

(58) Field of Classification Search
CPC .......... A61K 39/39558; A61K 2300/00; C07K 16/2827; A61P 35/00
See application file for complete search history.

(56) References Cited

FOREIGN PATENT DOCUMENTS

| | | | | | |
|---|---|---|---|---|---|
| WO | 2011/151360 | A1 | | 12/2011 | |
| WO | 2012/062783 | A1 | | 5/2012 | |
| WO | 2015/176010 | A1 | | 11/2015 | |
| WO | WO-2019221566 | A1 | * | 11/2019 | .............. A61P 25/00 |
| WO | 2020/040591 | A1 | | 2/2020 | |
| WO | 2020/223770 | A1 | | 11/2020 | |

OTHER PUBLICATIONS

Berland, L., et al., "Current views on tumor mutational burden in patients with non-small cell lung cancer treated by immune checkpoint inhibitors" J Thoraic Dis 11( Suppl 1):S71-S80 (Jan. 1, 2019).
Broekman, F., et al., "Tyrosine kinase inhibitors: Multi-targeted or single-targeted?" World J Clin Oncol 2(2):80-93 (Feb. 10, 2011).
Cookson, M.R., "LRRK2 Pathways Leading to Neurodegeneration" Curr Neurol Neurosci Rep 15(7):42 (May 26, 2015).
Gajewski, T., et al., "Innate and adaptive immune cells in the tumor microenvironment" Nat Immunology 14(10):10145-1022 (Sep. 18, 2013).
Gardet, A., et al., "LRRK2 Is Involved in the IFN-γ Response and Host Response to Pathogens" J Immunol (EPUB: Oct. 4, 2010), 185(9):5577-5585 (Nov. 1, 2010).
Gloeckner, C., et al., "The Parkinson disease-associated protein kinase LRRK2 exhibits MAPKKK activity and phosphorylates MKK3/6 and MKK4/7, in vitro" J Neurochem (EPUB: Mar. 3, 2009), 109(4):959-968 (Apr. 14, 2009).
Hamanishi, J., et al., "PD-1/PD-L1 blockade in cancer treatment: perspectives and issues" Int J Clin Oncol 21(3):462-473 (Feb. 22, 2016).
"International Preliminary Report on Patentability—PCT/EP2021/078732" (Report Issuance Date:: Apr. 13, 2023; Chapter I), :pp. 1-13 (May 4, 2023).
"International Search Report—PCT/EP2021/078732" (w/Written Opinion), :pp. 1-20 (Jan. 18, 2022).
Iwai, Y., et al., "Cancer immunotherapies targeting the PD-1 signaling pathway" J Biomed Sci 24(26):1-11 (Apr. 4, 2017).
Kramer, T., et al., "Small Molecule Kinase Inhibitors for LRRK2 and Their Application to Parkinson's Disease Models" ACS Chem Neurosci 3(3):151-160 (Mar. 21, 2012).
Lafferty, K.,, "A new analysis of allogeneic interactions" Aust J Exp Biol Med Sci 53(1):27-42 (Feb. 1, 1975).
Lenschow, D., et al., "CD28/B7 system of T cell costimulation" Annu Rev Immunol 14:233-258 (Apr. 1, 1996).
Liu, Z., et al., "The kinase LRRK2 is a regulator of the transcription factor NFAT that modulates the severity of inflammatory bowel disease" Nat Immunology 12(11):1063-1070 (Oct. 9, 2011).
Nguyen, A., et al. Leucine-Rich Repeat Kinase 2 (LRRK2)—Advances in Neurobiology "Chapter 4: Understanding the GTPase Activity of LRRK2: Regulation, Function, and Neurotoxicity" Rideout, H., ed., First edition, Cham, Switzerland: Springer International Publishing AG, vol. 14:71-88 (Apr. 4, 2017).
Okazaki, T., et al., "PD-1 and PD-1 ligands: from discovery to clinical application" Int Immunol 19(7):813-824 (Jul. 2, 2007).
Papaetis, G., et al., "Sunitinib: A Multitargeted Receptor Tyrosine Kinase Inhibitor in the Era of Molecular Cancer Therapies" BioDrugs 23(6):377-389 ( 2009).
Porcelli, L., et al., "Synergistic effect of sunitinib and PD-1 inhibitor nivolumab on colorectal cancer in vitro and in vivo" Poster (2238; Cancer Res 80(16 Suppl)) AACR Annual Meeting, San Diego, California—US, pp. 1 (Apr. 24-29, 2020).
Thévenet, J., et al., "Regulation of LRRK2 Expression Points to a Functional Role in Human Monocyte Maturation" PLoS One 6(6):e21519 (1-14) (Jun. 27, 2011).
Thompson, R., et al., "Tumor B7-H1 Is Associated with Poor Prognosis in Renal Cell Carcinoma Patients with Long-term Follow-up" Cancer Res 66(7):3381-3385 (Apr. 1, 2006).
Wallings, R. et al., "Cellular processes associated with LRRK2 function and dysfunction" Febs J (Epub: May 9, 2015), 282(15):2806-2826 (Aug. 1, 2015).
Wallings, R., et al., "LRRK2 regulation of immune-pathways and inflammatory disease" Biochem Soc Trans 47(6):1581-1595 (Nov. 26, 2019).
Warø, B., et al., "Exploring cancer in LRRK2 mutation carriers and idiopathic Parkinson's disease" Brain & Behavior (Epub: Dec. 7, 2017), 8(1):e00858 (1-6) (Jan. 1, 2018).
Kubo et al., (2020) "Leucine-Rich Repeat Kinase 2 Controls Inflammatory Cytokines Production through NF-KB Phosphorylation and Antigen Presentation in Bone Marrow-Derived Dendritic Cells" Int. J. Mol. Sci. 21(5 SUPPL https://doi.org/10.3390/ijms21051890):1-12.

* cited by examiner

| | LRRK2-IN-1 | 9605 | JH-II-127 | HG-10-102-01 | PF-06447475 | 7915 | MLi-2 |
|---|---|---|---|---|---|---|---|
| Cross-presentation on DC2.4 | ✓ | ✓ | ✓ | ✓ | ✓ | ✓ | ✓ |
| Effect on cancer cells (upon co-culture with Tcells primed by DC treated with LRRK2 inh) | ≥ 1μM (Human) | > 10nM (Mouse) | > 100nM (Mouse) | 100nM≥X≥1μM (Mouse) | >1μM (Mouse) | > 10nM (Mouse) | > 1nM (Mouse) |

FIG. 5G

| Mli-2 | 0.1µM | 1µM | 10µM |
|---|---|---|---|
| S65 | 4 | 9 | 10 |
| S90 | 3 | 3 | 2 |
| S99 | 2 | 2 | 1 |
| Total non-mutated kinases | 403 | 403 | 403 |
| LRRK2 inh | 98% | 99% | 96% |

FIG. 10A

| PFE-360 | 0.1µM | 1µM | 10µM |
|---|---|---|---|
| S65 | 17 | 64 | 193 |
| S90 | 9 | 28 | 92 |
| S99 | 3 | 4 | 35 |
| Total non-mutated kinases | 403 | 403 | 403 |
| LRRK2 inh | 100% | 99% | 98% |

FIG. 10B

| Sunitinib | 0.1μM | 1μM | 10μM |
|---|---|---|---|
| S65 | 38 | 141 | 257 |
| S90 | 14 | 71 | 197 |
| S99 | 6 | 15 | 84 |
| Total non-mutated kinases | 403 | 403 | 403 |
| LRRK2 inh | <50% | 93% | 100% |

FIG. 10C

| Mli-2 | 0.1μM | 1μM | 10μM |
|---|---|---|---|
| S65 | 0.01 | 0.022 | 0.052 |
| S90 | 0.007 | 0.007 | 0.025 |
| S99 | 0.002 | 0.002 | 0.002 |

| PFE-360 | 0.1μM | 1μM | 10μM |
|---|---|---|---|
| S65 | 0.042 | 0.159 | 0.479 |
| S90 | 0.022 | 0.069 | 0.288 |
| S99 | 0.007 | 0.01 | 0.087 |

| Sunitinib | 0.1μM | 1μM | 10μM |
|---|---|---|---|
| S65 | 0.094 | 0.35 | 0.638 |
| S90 | 0.035 | 0.176 | 0.489 |
| S99 | 0.015 | 0.037 | 0.208 |

FIG. 11

SEQUENCE LISTING

Sequence total quantity: 30
SEQ ID NO: 1 moltype = AA length = 440
FEATURE Location/Qualifiers
REGION 1..440
note = anti-PD-L1 antibody heavy chain
source 1..440
mol_type = protein
organism = synthetic construct -continued

```
SEQUENCE: 1
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSSASTKGPS  120
VFPLAPCSRS TSESTAALGC LVKDYFPEPV TVSWNSGALT SGVHTFPAVL QSSGLYSLSS  180
VVTVPSSSLG TKTYTCNVDH KPSNTKVDKR VESKYGPPCP PCPAPEFLGG PSVFLFPPKP  240
KDTLMISRTP EVTCVVVDVS QEDPEVQFNW YVDGVEVHNA KTKPREEQFN STYRVVSVLT  300
VLHQDWLNGK EYKCKVSNKG LPSSIEKTIS KAKGQPREPQ VYTLPPSQEE MTKNQVSLTC  360
LVKGFYPSDI AVEWESNGQP ENNYKTTPPV LDSDGSFFLY SRLTVDKSRW QEGNVFSCSV  420
MHEALHNHYT QKSLSLSLGK                                             440

SEQ ID NO: 2           moltype = AA  length = 214
FEATURE                Location/Qualifiers
REGION                 1..214
                       note = anti-PD-L1 antibody light chain
source                 1..214
                       mol_type = protein
                       organism = synthetic construct
SEQUENCE: 2
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 3           moltype = AA  length = 447
FEATURE                Location/Qualifiers
REGION                 1..447
                       note = anti-PD-L1 antibody heavy chain
source                 1..447
                       mol_type = protein
                       organism = synthetic construct
SEQUENCE: 3
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                     447

SEQ ID NO: 4           moltype = AA  length = 218
FEATURE                Location/Qualifiers
REGION                 1..218
                       note = anti-PD-L1 antibody light chain
source                 1..218
                       mol_type = protein
                       organism = synthetic construct
SEQUENCE: 4
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                         218

SEQ ID NO: 5           moltype = AA  length = 447
FEATURE                Location/Qualifiers
REGION                 1..447
                       note = anti-PD-L1 antibody heavy chain
source                 1..447
                       mol_type = protein
                       organism = synthetic construct
SEQUENCE: 5
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYAST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                     447

SEQ ID NO: 6           moltype = AA  length = 214
FEATURE                Location/Qualifiers
REGION                 1..214
                       note = anti-PD-L1 antibody light chain
source                 1..214
                       mol_type = protein
                       organism = synthetic construct
SEQUENCE: 6
DIQMTQSPSS LSASVGDRVT ITCRASQDVS TAVAWYQQKP GKAPKLLIYS ASFLYSGVPS  60
```

-continued

```
RFSGSGSGTD FTLTISSLQP EDFATYYCQQ YLYHPATFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 7           moltype = AA  length = 118
FEATURE                Location/Qualifiers
REGION                 1..118
                       note = anti-PD-L1 antibody VH
source                 1..118
                       mol_type = protein
                       organism = synthetic construct
SEQUENCE: 7
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSS    118

SEQ ID NO: 8           moltype = AA  length = 122
FEATURE                Location/Qualifiers
REGION                 1..122
                       note = anti-PD-L1 antibody VH
source                 1..122
                       mol_type = protein
                       organism = synthetic construct
SEQUENCE: 8
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSSAS  120
TK                                                                 122

SEQ ID NO: 9           moltype = AA  length = 108
FEATURE                Location/Qualifiers
REGION                 1..108
                       note = anti-PD-L1 antibody VL
source                 1..108
                       mol_type = protein
                       organism = synthetic construct
SEQUENCE: 9
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKR               108

SEQ ID NO: 10          moltype = AA  length = 10
FEATURE                Location/Qualifiers
REGION                 1..10
                       note = HVR-H1
source                 1..10
                       mol_type = protein
                       organism = synthetic construct
SEQUENCE: 10
GFTFSDSWIH                                                         10

SEQ ID NO: 11          moltype = AA  length = 18
FEATURE                Location/Qualifiers
REGION                 1..18
                       note = HVR-H2
source                 1..18
                       mol_type = protein
                       organism = synthetic construct
SEQUENCE: 11
AWISPYGGST YYADSVKG                                                18

SEQ ID NO: 12          moltype = AA  length = 9
FEATURE                Location/Qualifiers
REGION                 1..9
                       note = HVR-H3
source                 1..9
                       mol_type = protein
                       organism = synthetic construct
SEQUENCE: 12
RHWPGGFDY                                                          9

SEQ ID NO: 13          moltype = AA  length = 11
FEATURE                Location/Qualifiers
REGION                 1..11
                       note = HVR-L1
source                 1..11
                       mol_type = protein
                       organism = synthetic construct
SEQUENCE: 13
RASQDVSTAV A                                                       11

SEQ ID NO: 14          moltype = AA  length = 7
```

```
FEATURE                 Location/Qualifiers
REGION                  1..7
                        note = HVR-L2
source                  1..7
                        mol_type = protein
                        organism = synthetic construct
SEQUENCE: 14
SASFLYS                                                                    7

SEQ ID NO: 15           moltype = AA  length = 9
FEATURE                 Location/Qualifiers
REGION                  1..9
                        note = HVR-L3
source                  1..9
                        mol_type = protein
                        organism = synthetic construct
SEQUENCE: 15
QQYLYHPAT                                                                  9

SEQ ID NO: 16           moltype = AA  length = 25
FEATURE                 Location/Qualifiers
REGION                  1..25
                        note = anti-PDL1 antibody HC-FR1
source                  1..25
                        mol_type = protein
                        organism = synthetic construct
SEQUENCE: 16
EVQLVESGGG LVQPGGSLRL SCAAS                                                25

SEQ ID NO: 17           moltype = AA  length = 13
FEATURE                 Location/Qualifiers
REGION                  1..13
                        note = anti-PDL1 antibody HC-FR2
source                  1..13
                        mol_type = protein
                        organism = synthetic construct
SEQUENCE: 17
WVRQAPGKGL EWV                                                             13

SEQ ID NO: 18           moltype = AA  length = 32
FEATURE                 Location/Qualifiers
REGION                  1..32
                        note = anti-PDL1 antibody HC-FR3
source                  1..32
                        mol_type = protein
                        organism = synthetic construct
SEQUENCE: 18
RFTISADTSK NTAYLQMNSL RAEDTAVYYC AR                                        32

SEQ ID NO: 19           moltype = AA  length = 11
FEATURE                 Location/Qualifiers
REGION                  1..11
                        note = anti-PDL1 antibody HC-FR4
source                  1..11
                        mol_type = protein
                        organism = synthetic construct
SEQUENCE: 19
WGQGTLVTVS A                                                               11

SEQ ID NO: 20           moltype = AA  length = 11
FEATURE                 Location/Qualifiers
REGION                  1..11
                        note = anti-PDL1 antibody HC-FR4
source                  1..11
                        mol_type = protein
                        organism = synthetic construct
SEQUENCE: 20
WGQGTLVTVS S                                                               11

SEQ ID NO: 21           moltype = AA  length = 23
FEATURE                 Location/Qualifiers
REGION                  1..23
                        note = LC-FR1
source                  1..23
                        mol_type = protein
                        organism = synthetic construct
SEQUENCE: 21
DIQMTQSPSS LSASVGDRVT ITC                                                  23
```

-continued

```
SEQ ID NO: 22          moltype = AA  length = 15
FEATURE                Location/Qualifiers
REGION                 1..15
                       note = LC-FR2
source                 1..15
                       mol_type = protein
                       organism = synthetic construct
SEQUENCE: 22
WYQQKPGKAP KLLIY                                                   15

SEQ ID NO: 23          moltype = AA  length = 32
FEATURE                Location/Qualifiers
REGION                 1..32
                       note = LC-FR3
source                 1..32
                       mol_type = protein
                       organism = synthetic construct
SEQUENCE: 23
GVPSRFSGSG SGTDFTLTIS SLQPEDFATY YC                                32

SEQ ID NO: 24          moltype = AA  length = 11
FEATURE                Location/Qualifiers
REGION                 1..11
                       note = LC-FR4
source                 1..11
                       mol_type = protein
                       organism = synthetic construct
SEQUENCE: 24
FGQGTKVEIK R                                                       11

SEQ ID NO: 25          moltype = AA  length = 118
FEATURE                Location/Qualifiers
REGION                 1..118
                       note = anti-PDL1 antibody VH
source                 1..118
                       mol_type = protein
                       organism = synthetic construct
SEQUENCE: 25
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSA    118

SEQ ID NO: 26          moltype = AA  length = 108
FEATURE                Location/Qualifiers
REGION                 1..108
                       note = anti-PDL1 antibody VL
source                 1..108
                       mol_type = protein
                       organism = synthetic construct
SEQUENCE: 26
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKR               108

SEQ ID NO: 27          moltype = AA  length = 2527
FEATURE                Location/Qualifiers
source                 1..2527
                       mol_type = protein
                       organism = Homo sapiens
SEQUENCE: 27
MASGSCQGCE EDEETLKKLI VRLNNVQEGK QIETLVQILE DLLVFTYSER ASKLFQGKNI  60
HVPLLIVLDS YMRVASVQQV GWSLLCKLIE VCPGTMQSLM GPQDVGNDWE VLGVHQLILK  120
MLTVHNASVN LSVIGLKTLD LLLTSGKITL LILDEESDIF MLIFDAMHSF PANDEVQKLG  180
CKALHVLFER VSEEQLTEFV ENKDYMILLS ALTNFKDEEE IVLHVLHCLH SLAIPCNNVE  240
VLMSGNVRCY NIVVEAMKAF PMSERIQEVS CCLLHRLTLG NFFNILVLNE VHEFVVKAVQ  300
QYPENAALQI SALSCLALLT ETIFLNQDLE EKNENQENDD EGEEDKLFWL EACYKALTWH  360
RKNKHVQEAA CWALNNLLMY QNSLHEKIGD EDGHFPAHRE VMLSMLMHSS SKEVFQASAN  420
ALSTLLEQNV NFRKILLSKG IHLNVLELMQ KHIHSPEVAE SGCKMLNHLF EGSNTSLDIM  480
AAVVPKILTV MKRHETSLPV QLEALRAILH FIVPGMPEES REDTEFHHKL NMVKKQCFKN  540
DIHKLVLAAL NRFIGNPGIQ KCGLKVISSI VHFPDALEML SLEGAMDSVL HTLQMYPDDQ  600
EIQCLGLSLI GYLITKKNVF IGTGHLLAKI LVSSLYRFKD VAEIQTKGFQ TILAILKLSA  660
SFSKLLVHHS FDLVIFHQMS SNIMEQKDQQ FLNLCCKCFA KVAMDDYLKN VMLERACDQN  720
NSIMVECLLL LGADANQAKE GSSLICQVCE KESSPKLVEL LLNSGSREQD VRKALTISIG  780
KGDSQIISLL LRRLALDVAN NSICLGGFCI GKVEPSWLGP LFPDKTSNLR KQTNIASTLA  840
RMVIRYQMKS AVEEGTASGS DGNFSEDVLS KFDEWTFIPD SSMDSVFAQS DDLDSEGSEG  900
SFLVKKKSNS ISVGEFYRDA VLQRCSPNLQ RHSNSLGPIF DHEDLLKRKR KILSSDDSLR  960
SSKLQSHMRH SDSISSLASE REYITSLDLS ANELRDIDAL SQKCCISVHL EHLEKLELHQ  1020
NALTSFPQQL CETLKSLTHL DLHSNKFTSF PSYLLKMSCI ANLDVSRNDI GPSVVLDPTV  1080
KCPTLKQFNL SYNQLSFVPE NLTDVVEKLE QLILEGNKIS GICSPLRLKE LKILNLSKNH  1140
ISSLSENFLE ACPKVESFSA RMNFLAAMPF LPPSMTILKL SQNKFSCIPE AILNLPHLRS  1200
LDMSSNDIQY LPGPAHWKSL NLRELLFSHN QISILDLSEK AYLWSRVEKL HLSHNKLKEI  1260
```

-continued

```
PPEIGCLENL TSLDVSYNLE LRSFPNEMGK LSKIWDLPLD ELHLNFDFKH IGCKAKDIIR  1320
FLQQRLKKAV PYNRMKLMIV GNTGSGKTTL LQQLMKTKKS DLGMQSATVG IDVKDWPIQI  1380
RDKRKRDLVL NVWDFAGREE FYSTHPHFMT QRALYLAVYD LSKGQAEVDA MKPWLFNIKA  1440
RASSSPVILV GTHLDVSDEK QRKACMSKIT KELLNKRGFP AIRDYHFVNA TEESDALAKL  1500
RKTIINESLN FKIRDQLVVG QLIPDCYVEL EKIILSERKN VPIEFPVIDR KRLLQLVREN  1560
QLQLDENELP HAVHFLNESG VLLHFQDPAL QLSDLYFVEP KWLCKIMAQI LTVKVEGCPK  1620
HPKGIISRRD VEKFLSKKRK FPKNYMSQYF KLLEKFQIAL PIGEEYLLVP SSLSDHRPVI  1680
ELPHCENSEI IIRLYEMPYF PMGFWSRLIN RLLEISPYML SGRERALRPN RMYWRQGIYL  1740
NWSPEAYCLV GSEVLDNHPE SFLKITVPSC RKGCILLGQV VDHIDSLMEE WFPGLLEIDI  1800
CGEGETLLKK WALYSFNDGE EHQKILLDDL MKKAEEGDLL VNPDQPRLTI PISQIAPDLI  1860
LADLPRNIML NNDELEFEQA PEFLLGDGSF GSVYRAAYEG EEVAVKIFNK HTSLRLLRQE  1920
LVVLCHLHHP SLISLLAAGI RPRMLVMELA SKGSLDRLLQ QDKASLTRTL QHRIALHVAD  1980
GLRYLHSAMI IYRDLKPHNV LLFTLYPNAA IIAKIADYGI AQYCCRMGIK TSEGTPGFRA  2040
PEVARGNVIY NQQADVYSFG LLLYDILTTG GRIVEGLKFP NEFDELEIQG KLPDPVKEYG  2100
CAPWPMVEKL IKQCLKENPQ ERPTSAQVFD ILNSAELVCL TRRILLPKNV IVECMVATHH  2160
NSRNASIWLG CGHTDRGQLS FLDLNTEGYT SEEVADSRIL CLALVHLPVE KESWIVSGTQ  2220
SGTLLVINTE DGKKRHTLEK MTDSVTCLYC NSFSKQSKQK NFLLVGTADG KLAIFEDKTV  2280
KLKGAAPLKI LNIGNVSTPL MCLSESTNST ERNVMWGGCG TKIFSFSNDF TIQKLIETRT  2340
SQLFSYAAFS DSNIITVVVD TALYIAKQNS PVVEVWDKKT EKLCGLIDCV HFLREVMVKE  2400
NKESKHKMSY SGRVKTLCLQ KNTALWIGTG GGHILLLDLS TRRLIRVIYN FCNSVRVMMT  2460
AQLGSLKNVM LVLGYNRKNT EGTQKQKEIQ SCLTVWDINL PHEVQNLEKH IEVRKELAEK  2520
MRRTSVE                                                            2527

SEQ ID NO: 28           moltype = AA  length = 8
FEATURE                 Location/Qualifiers
REGION                  1..8
                        note = SIINFEKL peptide
source                  1..8
                        mol_type = protein
                        organism = synthetic construct
SEQUENCE: 28
SIINFEKL                                                           8

SEQ ID NO: 29           moltype = AA  length = 25
FEATURE                 Location/Qualifiers
REGION                  1..25
                        note = Mutated long Melan-A/MART-1 peptide
source                  1..25
                        mol_type = protein
                        organism = synthetic construct
SEQUENCE: 29
HGHSYTTAEE LAGIGILTVI LGVLP                                        25

SEQ ID NO: 30           moltype = AA  length = 10
FEATURE                 Location/Qualifiers
REGION                  1..10
                        note = Mutated short Melan-A/MART-126-35 peptide
source                  1..10
                        mol_type = protein
                        organism = synthetic construct
SEQUENCE: 30
ELAGIGILTV                                                         10
```

COMBINATION THERAPY OF PD-1 AXIS BINDING ANTAGONISTS AND LRRK2 INHITIBORS

CROSS REFERENCE TO RELATED APPLICATIONS

This application is a Continuation of International Patent Application No. PCT/EP2021/078732, filed Oct. 18, 2021, which claims priority to European Application No. 20202857.7, filed Oct. 20, 2020, the contents of which are hereby incorporated by reference.

SEQUENCE LISTING

The instant application contains a Sequence Listing with 30 sequences submitted electronically in XML format and is hereby incorporated by reference in its entirety. Said XML copy, created Apr. 17, 2023, is named P36397-US_Sequence_Listing.xml and is 42,905 bytes in size.

FIELD OF THE INVENTION

The present invention relates to combination therapies employing PD-1 axis binding antagonists and LRRK2 inhibitors, and the use of these combination therapies for the treatment of cancer.

BACKGROUND

Clinical data demonstrated that therapeutic response to cancer immunotherapy is highly connected to the tumor mutational burden. High mutation load is postulated to be linked to neo-antigen generation. Neo-antigens presented on major histocompatibility complexes can be recognized as foreign by the host immune system and trigger an immune response.

Dendritic cells have the capability to take up tumor antigens/neo-antigens (Léa Berland, et Al. 2019), present the antigens on major histocompatibility complex I and II (hereafter MHC-I and MHC-II) and subsequently activate the adaptive immune response through the priming of T-cells (Thomas F Gajewski et Al. 2014). In particular, the antigen presentation on MHC-I by dendritic cells (cross-presentation) and the subsequent priming of cytotoxic CD8+ T cells is in the focus of cancer immunotherapy.

Because of this orchestrating role of dendritic cells in the anti-tumor immune response, the identification of genes pivotal for antigen processing and cross-presentation that have the potential to enhance the T cell mediated cytotoxic immune response against the tumor would provide access to novel and hitherto unknown drug targets for the treatment of cancer.

The applicant developed a new CRISPR/Cas9 based screening approach for the identification of novel target for cancer immunotherapy in dendritic cells. The screening readout was FACS-based and detected cross-presented SIINFEKL peptide on H2Kb by an H2Kb-SIINFEKL monoclonal antibody. The applicant surprisingly identified and validated Leucine-rich repeat kinase 2 (LRRK2) as the most promising drug target candidate. The applicant could show that the knockout of LRRK2 as well as the inhibition of LRRK2 kinase activity, specifically in dendritic cells, leads to an increased cross-presentation, subsequent T cell priming and T cell mediated cytotoxicity. In addition, the applicant demonstrates that pharmacological intervention in tumor bearing animals leads to a significant tumor growth inhibition and has a synergistic effect with checkpoint inhibition.

LRRK2 is expressed in a variety of peripheral organs (e.g., kidney, lung, liver, heart, and spleen) and in the brain. LRRK2 is a large protein (286 kDa) with several distinct domains, two of which have a distinct enzymatic activity: a GTPase and a kinase functions (Cookson, 2015; Wallings et al., 2015). LRRK2 is a serine-threonine kinase capable of auto-phosphorylating LRRK2 itself, as well as phosphorylating heterologous substrates (Gloeckner, Schumacher, Boldt, & Ueffing, 2009). The GTPase activity is mediated by the ROC (Ras of complex proteins) domain however, the contribution of the GTPase activity to the function of LRRK2 is not fully understood (An Phu Tran Nguyen and Darren J. Moore, 2018). Moreover, LRRK2 is reported to act as structural scaffold for protein-protein interactions in a complex that was described as a repressor of the Nuclear factor of activated T-cells (NFAT) transcription factor (Zhihua Liu et al, 2011).

Subcellular localization studies indicated that LRRK2 associates with membranous and vesicular structures, including mitochondria, lysosomes, endosomes, lipid rafts and vesicles and multiple evidences linked LRRK2 to a diverse range of cellular functions, including autophagy, cytoskeletal dynamics, intracellular membrane trafficking, synaptic vesicle cycling and inflammatory response (Cookson, 2015; Wallings et al., 2015). Interestingly, LRRK2 is highly expressed in immune cells, mostly monocytes, macrophages, B lymphocytes and dendritic cells (Gardet et al., 2010; Thevenet, Pescini Gobert, Hooft van Huijsduijnen, Wiessner, & Sagot, 2011). LRRK2 has been implicated in human diseases, such as Parkinson's disease (PD) and a number of chronic inflammatory conditions as Crohn's disease (CD), inflammatory bowel disease and Leprosy (Rebecca L. Wallings and Malú G. Tansey, 2019).

Activation of resting T lymphocytes, or T cells, by antigen-presenting cells (APCs) appears to require two signal inputs. Lafferty et al, Aust. J. Exp. Biol. Med. ScL 53: 27-42 (1975). The primary, or antigen specific, signal is transduced through the T-cell receptor (TCR) following recognition of foreign antigen peptide presented in the context of the major histocompatibility-complex (MHC). The second, or co-stimulatory, signal is delivered to T-cells by co-stimulatory molecules expressed on antigen-presenting cells (APCs), and promotes T-cell clonal expansion, cytokine secretion and effector function. Lenschow et al., Ann. Rev. Immunol. 14:233 (1996).

Recently, it has been discovered that T cell dysfunction or anergy occurs concurrently with an induced and sustained expression of the inhibitory receptor, programmed death 1 polypeptide (PD-1). One of its ligands, PD-L1 is overexpressed in many cancers and is often associated with poor prognosis (Okazaki T et al., Intern. Immun. 2007 19(7):813) (Thompson R H et al., Cancer Res 2006, 66(7):3381). Interestingly, the majority of tumor infiltrating T lymphocytes predominantly express PD-1, in contrast to T lymphocytes in normal tissues and peripheral blood T lymphocytes indicating that up-regulation of PD-1 on tumor-reactive T cells can contribute to impaired antitumor immune responses (Blood 2009 1 14(8): 1537).

Current therapeutic strategies for the treatment of cancer are primarily focused on immunotherapies targeting known oncogenes, tumor repressor genes and well established pathways involved in the formation of cancers. While these therapies have undeniably provided huge benefits for the patients suffering from cancer, the effect of such therapies is in many cases limited in time. Therefore, there is an urgent need to identify and develop novel strategies with the potential to enhance and complement the current therapies.

Hence, there remains a need for an optimal therapy for treating, stabilizing, preventing, and/or delaying development of various cancers.

SUMMARY

The present invention relates to PD-1 axis binding antagonists, in particular antibodies, and their use in combination with a LRRK2 inhibitor, e.g., for the treatment of cancer. The methods and combinations of the present invention enable improved immunotherapy, in particular for treating or delaying progression of advanced and/or metastatic solid tumors. It has been found that the combination therapy described herein is more effective in inhibiting tumor growth and eliminating tumor cells than treatment with the PD-1 axis antagonist antibodies alone.

Provided is a PD-1 axis binding antagonist for use in a method for treating or delaying progression of cancer, wherein the PD-1 axis binding antagonist is used in combination with a LRRK2 inhibitor.

In one embodiment, the PD-1 axis binding antagonist the PD-1 axis binding antagonist is selected from the group consisting of a PD-1 binding antagonist, a PD-L1 binding antagonist and a PD-L2 binding antagonist. In one embodiment, the PD-1 axis binding antagonist inhibits the binding of PD-1 to its ligand binding partners. In one embodiment, the PD-1 binding antagonist is an antibody. In one embodiment, the PD-1 axis binding antagonist is an antibody fragment selected from the group consisting of Fab, Fab'-SH, Fv, scFv, and (Fab')2 fragments. In one embodiment, the PD-1 axis binding antagonist is a monoclonal antibody.

In one embodiment, the PD-1 axis binding antagonist is a humanized antibody or a human antibody. In one embodiment, the PD-1 axis binding agonist is an antibody comprising a heavy chain comprising HVR-H1 sequence of SEQ ID NO:10, HVR-H2 sequence of SEQ ID NO:11, and HVR-H3 sequence of SEQ ID NO:12; and a light chain comprising HVR-L1 sequence of SEQ ID NO:13, HVR-L2 sequence of SEQ ID NO:14, and HVR-L3 sequence of SEQ ID NO:15. In one embodiment, wherein the PD-1 axis binding agonist is an antibody comprising a heavy chain variable region comprising the amino acid sequence of SEQ ID NO:7 or SEQ ID NO:8 and a light chain variable region comprising the amino acid sequence of SEQ ID NO:9.

In one embodiment, the PD-1 axis binding antagonist is an antibody comprising a heavy chain comprising the amino acid sequence of SEQ ID NO:5 and a light chain comprising the amino acid sequence of SEQ ID NO:6. In one embodiment, the PD-1 axis binding antagonist is selected from the group consisting of nivolumab, pembrolizumab, and pidilizumab. In one embodiment, the PD-1 axis binding antagonist is AMP-224. In one embodiment, the PD-1 axis binding agonist is selected from the group consisting of YW243.55.S70, atezolizumab, MDX-1105, and durvalumab. In one embodiment, the LRRK2 inhibitor has a molecular weight of 200-900 dalton. In one embodiment, the LRRK2 inhibitor comprises an aromatic cycle, which is attached to a heterocycle via a nitrogen atom, wherein the nitrogen atom can form part of the heterocycle. In one embodiment, the heterocycle comprises at least two heteroatoms. In one embodiment, the LRRK2 inhibitor has an IC50 value below 1 μM, below 500 nM, below 200 nM, below 100 nM, below 50 nM, below 25 nM, below 10 nM, below 5 nM, 2 nM or below 1 nM. In one embodiment, the LRRK2 inhibitor is a compound of formula (I)

(I)

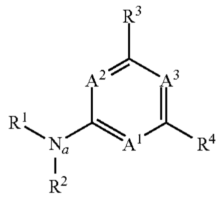

wherein, $A^1$ is —N— or —$CR^5$—;

$A^2$ is —N— or —$CR^6$—;

$A^3$ is —N— or —$CR^7$—;

$N_a$ is —N—;

$R^1$ is alkylamino(haloalkylpyrimidinyl), cyanoalkyl(alkylpyrazolyl), alkylamino(halopyrimidinyl), oxetanyl (halopiperidinyl)halopyrazolyl, halo(N-alkyl-3H-pyrrolo[2,3-d]pyrimidine-amine), 5,11-dialkylpyrimido[4,5-b][1,4]benzodiazepin-6-one, phenyl optionally substituted with one, two or three substituents independently selected from $R_a$, pyrazolyl optionally substituted with one, two or three substituents independently selected from $R_a$, or a condensed bicyclic system optionally substituted with one, two or three substituents independently selected from $R_a$;

$R_a$ is (heterocyclyl)carbonyl, (heterocyclyl)alkyl, heterocyclyl, alkoxy, aminocarbonyl, alkylaminocarbonyl, amino(alkylamino)carbonyl, oxetanylaminocarbonyl, (tetrahydropyranyl)aminocarbonyl, (dialkylamino)carbonyl, (cycloalkylamino)carbonyl, hydroxy, haloalkoxy, cycloalkoxy, (hydroxyalkyl)aminocarbonyl, (alkoxyalkyl)aminocarbonyl, (alkylpiperidinyl) aminocarbonyl, (alkoxyalkyl)alkylaminocarbonyl, (hydroxyalkyl)(alkylamino)carbonyl, (cyanocycloalkyl) aminocarbonyl, (cycloaklyl)alkylaminocarbonyl, (haloazetidinyl)aminocarbonyl, (haloalkyl)aminocarbonyl, morpholinylcarbonylalkyl, morpholinylalkyl, alkyl, fluorine, chlorine, bromine, iodine, (perdeuteromorpholinyl)carbonyl, (halocycloalkyl)aminocarbonyl, oxetanyloxy, (cycloalkyl)alkoxy, cycloalkyl, cyano, alkenyl, alkynyl, alkoxyalkyl, hydroxyalkyl, (cycloalkyl)alkyl, alkylsulfonyl, phenyl, haloalkyl, cyanophenyl, cycloalkylsulfonyl, cyanoalkyl, alkylsulfonylphenyl, (dialkylamino)carbonylphenyl, halophenyl, (alkyloxetanyl)alkyl, (dialkylamino)phenyl, (cycloalkylsulfonyl)phenyl, alkoxycycloalkyl, (alkylamino)carbonylalkyl, pyridazinylalkyl, pyrimidinylalkyl, (alkylpyrazolyl)alkyl, triazolylalkyl, (alkyltriazolyl)alkyl, hydroxycycloalkyl, (oxadiazolyl) alkyl, (dialkylamino)carbonylalkyl, pyrrolidinylcarbonylalkyl, cyanocycloalkyl, alkoxycarbonylalkyl, (haloalkyl)aminocarbonylalkyl, (cycloalkyl) alkylaminocarbonylalkyl, (alkylamino) carbonylcycloalkyl, alkylpiperidinyl(alkylamino) carbonyl, alkylpyrazolyl(alkylamino)carbonyl, (hydroxycycloalkyl)alkylaminocarbonyl, (hydroxycycloalkyl)alkyl, (dialkylimidazolyl)alkyl, (alkyloxazolyl)alkyl, alkoxyalkylsulfonyl, hydroxycarbonyl, morpholinylsulfonyl or alkyl(oxadiazolyl)alkyl, $R^2$ is alkyl or hydrogen;

or $R^1$ and $R^2$ together with $N_a$ form a morpholino optionally substituted with one, two or three alkyl;

$R^3$ and $R^4$ are independently selected from alkoxy, cycloalkylamino, (cycloalkyl)alkylamino, (tetrahydrofuranyl)alkylamino, alkoxyalkylamino, (tetrahydropyranyl)amino, (tetrahydropyranyl)oxy, (tetrahydropyranyl)alkylamino, haloalkylamino, piperidinyl, pyrrolidinyl, (oxetanyl)oxy, haloalkoxy, hydrogen, halogen, alkylamino, morpholinyl and alkyl(cycloalkyloxy)indazolyl;

or $R^3$ is hydrogen, and $R^4$ together with $R^5$ form a pyrrolyl substituted with $R^8$, wherein the pyrrolyl is fused to the aromatic cycle comprising $A^1$, $A^2$ and $A^3$;

$R^5$ and $R^6$ are independently selected from hydrogen and alkyloxy;

$R^7$ is hydrogen, halogen, alkyl, cycloalkyl, alkenyl, alkynyl, cyano, haloalkoxy, (cycloalkyl)alkyl, haloalkyl, (alkylpiperazinyl)piperidinylcarbonyl or morpholinocarbonyl; and $R^8$ is pyrrolyl substituted with cyano(alkylpyrrolyl) or cyanophenyl;

or a pharmaceutically acceptable salt thereof.

In one embodiment, the LRRK2 inhibitor is a compound of formula (I)

(I)

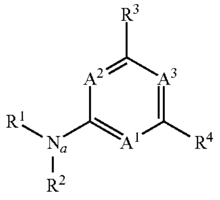

wherein, $A^1$ is —N— or —$CR^5$—;

$A^2$ is —N— or —$CR^6$—;

$A^3$ is —N— or —$CR^7$—;

$N_a$ is —N—;

$R^1$ is alkylamino(haloalkylpyrimidinyl), cyanoalkyl(alkylpyrazolyl), alkylamino(halopyrimidinyl), oxetanyl(halopiperidinyl)halopyrazolyl, halo(N-alkyl-3H-pyrrolo[2,3-d]pyrimidine-amine) or 5,11-dialkylpyrimido[4,5-b][1,4]benzodiazepin-6-one;

$R^2$ is hydrogen;

or $R^1$ and $R^2$ together with $N_a$ form a morpholino optionally substituted with one, two or three alkyl;

$R^3$ and $R^4$ are independently selected from hydrogen, halogen, alkylamino, morpholinyl and alkyl(cycloalkyloxy)indazolyl;

or $R^3$ is hydrogen, and $R^4$ together with $R^5$ form a pyrrolyl substituted with wherein the pyrrolyl is fused to the aromatic cycle comprising $A^1$, $A^2$ and $A^3$;

$R^5$ and $R^6$ are independently selected from hydrogen and alkyloxy;

$R^7$ is haloalkyl, (alkylpiperazinyl)piperidinylcarbonyl or morpholinocarbonyl; and $R^8$ is pyrrolyl substituted with cyano(alkylpyrrolyl) or cyanophenyl;

or a pharmaceutically acceptable salt thereof.

In one embodiment, the LRRK2 inhibitor is a compound of formula (I a)

($I_a$)

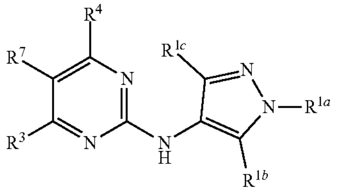

wherein $R^{1a}$ is cyanoalkyl or oxetanyl(halopiperidinyl).

$R^{1b}$ and $R^{1c}$ are independently selected from hydrogen, alkyl and halogen;

$R^3$ and $R^4$ are independently selected from hydrogen and alkylamino; and $R^7$ is haloalkyl;

or a pharmaceutically acceptable salt thereof.

In one embodiment, the LRRK2 inhibitor is a compound of formula ($I_b$)

($I_b$)

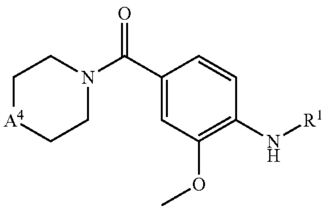

wherein $R^1$ is alkylamino(halopyrimidinyl), halo(N-alkyl-3H-pyrrolo[2,3-d]pyrimidine-amine) or 5,11-dialkylpyrimido[4,5-b][1,4]benzodiazepin-6-one;

$R^3$ is halogen;

$A^4$ is —O— or —$CR^9$—; and $R^9$ is alkylpiperazinyl;

or a pharmaceutically acceptable salt thereof.

In one embodiment, the LRRK2 inhibitor is a compound of formula ($I_c$)

($I_c$)

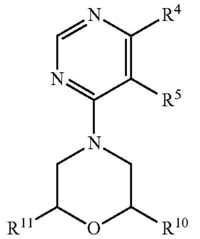

wherein, $R^4$ is alkyl(cycloalkyloxy)indazolyl, and $R^5$ is hydrogen;

or $R^4$ together with $R^5$ forms a pyrrolyl substituted with $R^8$, wherein the pyrrolyl is fused to the pyrimidine of the compound of formula ($I_c$);

$R^8$ is pyrrolyl substituted with cyano(alkylpyrrolyl) or cyanophenyl; and $R^{10}$ and $R^{11}$ are independently selected from hydrogen and alkyl;

or a pharmaceutically acceptable salt thereof.

In one embodiment, the LRRK2 inhibitor is selected from

[4-[[4-(ethylamino)-5-(trifluoromethyl)pyrimidin-2-yl]amino]-2-fluoro-5-methoxy-phenyl]-morpholino-methanone;

2-methyl-2-[3-methyl-4-[[4-(methylamino)-5-(trifluoromethyl)pyrimidin-2-yl]amino]pyrazol-1-yl]propanenitrile;

N2-[5-chloro-1-[3-fluoro-1-(oxetan-3-yl)-4-piperidyl]pyrazol-4-yl]-N4-methyl-5-(trifluoromethyl)pyrimidine-2,4-diamine;

[4-[[5-chloro-4-(methylamino)pyrimidin-2-yl]amino]-3-methoxy-phenyl]-morpholino-methanone;

[4-[[5-chloro-4-(methylamino)-3H-pyrrolo[2,3-d]pyrimidin-2-yl]amino]-3-methoxy-phenyl]-morpholino-methanone;

2-[2-methoxy-4-[4-(4-methylpiperazin-1-yl)piperidine-1-carbonyl]anilino]-5,11-dimethyl-pyrimido[4,5-b][1,4]benzodiazepin-6-one;

3-(4-morpholino-7H-pyrrolo[2,3-d]pyrimidin-5-yl)benzonitrile; cis-2,6-dimethyl-4-[6-[5-(1-methylcyclopropoxy)-1H-indazol-3-yl]pyrimidin-4-yl]morpholine;

1-methyl-4-(4-morpholino-7H-pyrrolo[2,3-d]pyrimidin-5-yl)pyrrole-2-carbonitrile; or a pharmaceutically acceptable salt thereof.

In one embodiment, the cancer is selected from the group consisting of ovarian cancer, lung cancer, breast cancer, renal cancer, colorectal cancer, endometrial cancer. In one embodiment, the LRRK2 inhibitor with a PD-1 axis binding antagonist to treat or delay progression of cancer in an individual.

In a further embodiment, provided is a kit comprising a LRRK2 inhibitor and a PD-1 axis binding antagonist, and a package insert comprising instructions for using the LRRK2 inhibitor and the PD-1 axis binding antagonist to treat or delay progression of cancer in an individual. In one embodiment, the PD-1 axis binding antagonist is an anti-PD-1 antibody or an anti-PD-L1 antibody. In one embodiment, the PD-1 axis binding antagonist is an anti-PD-1 immunoadhesin.

In a further embodiment, provided is a pharmaceutical product comprising (A) a first composition comprising as active ingredient a PD-1 axis binding antagonist antibody and a pharmaceutically acceptable carrier; and (B) a second composition comprising as active ingredient a LRRK2 inhibitor and a pharmaceutically acceptable carrier, for use in the combined, sequential or simultaneous, treatment of a disease, in particular cancer.

In a further embodiment, provided is a pharmaceutical composition comprising a LRRK2 inhibitor, a PD-1 axis binding antagonist and a pharmaceutically acceptable carrier. In one embodiment, provided is the pharmaceutical product or the pharmaceutical composition as herein described for use in treating or delaying progression of cancer, in particular for treating or delaying of ovarian cancer, lung cancer, breast cancer, renal cancer, colorectal cancer, endometrial cancer.

In a further embodiment, provided is the use of a combination of a LRRK2 inhibitor and a PD-1 axis binding antagonist in the manufacture of a medicament for treating or delaying progression of a proliferative disease, in particular cancer. In one embodiment, the medicament is for treatment of ovarian cancer, lung cancer, breast cancer, renal cancer, colorectal cancer, endometrial cancer.

In a further embodiment, provided is a method for treating or delaying progression of a cancer in an individual comprising administering to the individual an effective amount of a LRRK2 inhibitor and a PD-1 axis binding antagonist. In one embodiment, the PD-1 axis binding antagonist is selected from the group consisting of a PD-1 binding antagonist, a PD-L1 binding antagonist and a PD-L2 binding antagonist. In one embodiment, the PD-1 axis binding antagonist is an antibody.

BRIEF DESCRIPTION OF THE FIGURES

FIG. 2B: FACS evaluation of OT-1 CD8a T cell activation through proliferation measurement. All experiments were performed in triplicates.

FIG. 3A: Schematic representation of the killing assay experimental setup. Co-cultured of MC38-RFP-Ova cells with OT1 CD8a T cells primed by DC2.4 SCR, LRRK2 or B2M knockout. FIG. 3B: Evaluation of T cell cytotoxicity over time depicted as MC38-RFP-OVA cancer cell viability. Data are normalized to SCR DC2.4 co-cultured with CD8a T cells but un-loaded with OVA long peptide (241-270). All experiments were performed in triplicates.

FIG. 4A, FIG. 4C, FIG. 4E, FIG. 4G) FACS based measurement of DC2.4 antigen cross-presentation upon treatment with the LRRK2 inhibitors. Cells were stained with anti-mouse H-2Kb/SIINFEKL antibody. FIG. 4B, FIG. 4D, FIG. 4H) FACS based evaluation of murine OT1 CD8a T cell proliferation upon co-culture with DC2.4 pre-treated with the LRRK2 inhibitors. FIG. 4F) FACS evaluation of human MART-1 T cell proliferation, upon co-culture with human cord blood derived dendritic cells pre-treated with the LRRK2 inhibitor LRRK2-IN-1. All the experiments were performed in triplicates.

FIG. 5G) Recapitulating table of the seven different LRRK2 inhibitors tested on dendritic cells for enhancement of cross-presentation capabilities and in a killing assay where T cells were primed by dose escaleted treated dendritic cells and, subsequently, used for co-culture with cancer cells.

FIG. 2: In vivo efficacy of PFE-360 and Mli-2 in NSG (NOD scid gamma mouse) tumor bearing mice. PFE-360 and Mli-2 are not impacting MC-38 tumor growth in comparison with vehicle treated mice. The average tumor growth from day zero to day 24 is expressed in mm3. Results are expressed as mean+/−SEM. All parameters were analyzed using GraphPad Prism software.

FIG. 10A, FIG. 10B, FIG. 10C: In vitro kinase selectivity test. Kinase selectivity of Mli-2 and PFE-360 was determined by running a KINOMEScan® (DiscoverX, CA, USA) for their selectivity against 403 non-mutated kinases. As a reference, the pan-kinase inhibitor sunitinib was tested. Displayed are the number of kinase where the binding to their ligand is reduced by greater than 65%, 90% or 99% respectively by Mli-2 (FIG. 10A), PFE-360 (FIG. 10B) and sunitinib (FIG. 10C) at 0.1 uM, 1 uM and 10 uM.

FIG. 11: Kinase selectivity of Mli-2 and PFE-360 was determined by running a KINOMEScan® (DiscoverX, CA, USA) for their selectivity against 403 non-mutated kinases. As a reference, the pan-kinase inhibitor sunitinib was tested. Displayed is the kinase selectivity score for each compound tested at different concentrations 0.1 uM, 1 uM and 10 uM. The selectivity score is a quantitative measure of compound selectivity and is calculated for a better comparison between compounds for the selectivity of >65% (S65), >90% (S90) and >99% (S99).

DETAILED DESCRIPTION OF EMBODIMENTS OF THE INVENTION

I. Definitions

Figure 1:
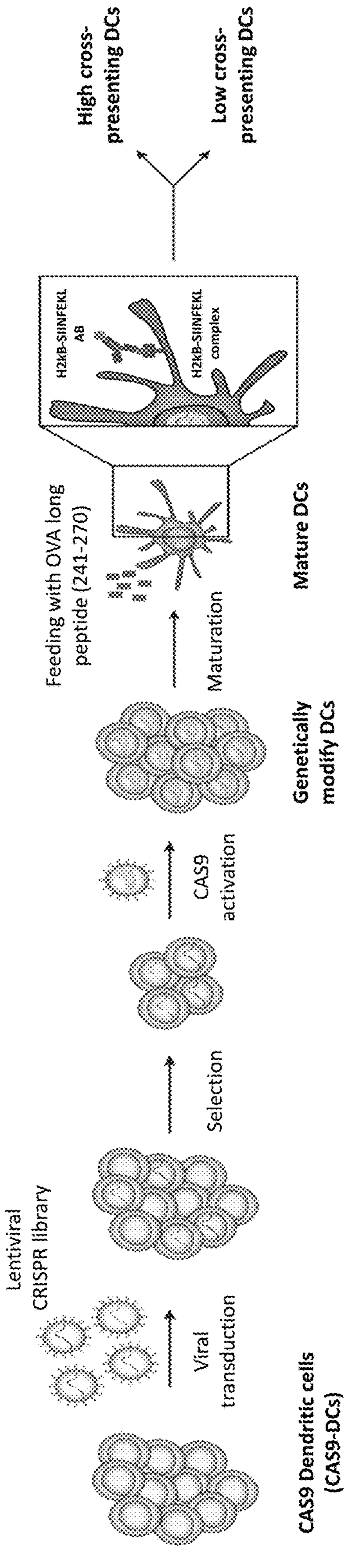
FIG. 1: Sorting based CRISPR/Cas9 screening strategy in Dendritic Cells (DCs). Schematic of the experimental setup from viral transduction with Cas9 and sgRNA mouse curated library, through the activation, maturation and feeding with the OVA long peptide (241-270), concluding with the DC2.4 sorting in high and low cross-presenting dendritic cells based on the quantity of the cell surface MHC-I/SIINFEKL complex detected by anti-mouse H-2Kb/SIINFEKL antibody.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some aspects, the number of amino acid changes are 10 or less, 9 or less, 8 or less, 7 or less, 6 or less, 5 or less, 4 or less, 3 or less, or 2 or less. In some aspects, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary methods for measuring binding affinity are described in the following.

An "affinity matured" antibody refers to an antibody with one or more alterations in one or more complementary determining regions (CDRs), compared to a parent antibody which does not possess such alterations, such alterations resulting in an improvement in the affinity of the antibody for antigen.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; single-chain antibody molecules (e.g., scFv, and scFab); single domain antibodies (dAbs); and multispecific antibodies formed from antibody fragments. For a review of certain antibody fragments, see Holliger and Hudson, Nature Biotechnology 23:1126-1136 (2005).

The term "linker" as used herein refers to a peptide linker and is preferably a peptide with an amino acid sequence with a length of at least 5 amino acids, preferably with a length of 5 to 100, more preferably of 10 to 50 amino acids. In one embodiment said peptide linker is $(G_xS)_n$ or $(G_xS)_nG_m$ with G=glycine, S=serine, and (x=3, n=3, 4, 5 or 6, and m=0, 1, 2 or 3) or (x=4, n=2, 3, 4 or 5 and m=0, 1, 2 or 3), preferably x=4 and n=2 or 3, more preferably with x=4, n=2. In one embodiment said peptide linker is $(G_4S)_2$.

The term "immunoglobulin molecule" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The heavy chain of an immunoglobulin may be assigned to one of five types, called α (IgA), δ (IgD), ε (IgE), γ (IgG), or μ (IgM), some of which may be further divided into subtypes, e.g. $\gamma_1$ ($IgG_1$), $\gamma_2$ ($IgG_2$), $\gamma_3$ ($IgG_3$), $\gamma_4$ ($IgG_4$), $\alpha_1$ ($IgA_1$) and $\alpha_2$ (IgA2). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "antigen binding domain" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more antibody variable domains (also called antibody variable regions). Preferably, an antigen binding domain comprises an antibody light chain variable region (VL) and an antibody heavy chain variable region (VH).

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. In certain aspects, the antibody is of the $IgG_1$ isotype. In certain aspects, the antibody is of the $IgG_1$ isotype with the P329G, L234A and L235A mutation to reduce Fc-region effector function. In other aspects, the antibody is of the $IgG_2$ isotype. In certain aspects, the antibody is of the $IgG_4$ isotype with the S228P mutation in the hinge region to improve stability of $IgG_4$ antibody. The heavy chain constant domains that correspond to the different classes of immunoglobulins are called α, δ, ε, γ, and μ, respectively. The light chain of an antibody may be assigned to one of two types, called kappa (κ) and lambda (λ), based on the amino acid sequence of its constant domain.

The terms "constant region derived from human origin" or "human constant region" as used in the current application denotes a constant heavy chain region of a human antibody of the subclass $IgG_1$, $IgG_2$, $IgG_3$, or $IgG_4$ and/or a constant light chain kappa or lambda region. Such constant regions are well known in the state of the art and e.g. described by Kabat, E. A., et al., Sequences of Proteins of Immunological Interest, 5th ed., Public Health Service, National Institutes of Health, Bethesda, MD (1991) (see also e.g. Johnson, G., and Wu, T. T., Nucleic Acids Res. 28 (2000) 214-218; Kabat, E. A., et al., Proc. Natl. Acad. Sci. USA 72 (1975) 2785-2788). Unless otherwise specified herein, numbering of amino acid residues in the constant region is according to the EU numbering system, also called the EU index of Kabat, as described in Kabat, E. A. et al., Sequences of Proteins of Immunological Interest, 5th ed., Public Health Service, National Institutes of Health, Bethesda, MD (1991), NIH Publication 91-3242.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor, or increased association with another peptide. Amino acid sequence deletions and insertions include amino- and/or carboxy-terminal deletions and insertions of amino acids. Particular amino acid mutations are amino acid substitutions. For the purpose of altering e.g. the binding characteristics of an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, omithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, G329, $G_{329}$, P329G, or Pro329Gly.

An "effective amount" of an agent, e.g., a pharmaceutical composition, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one aspect, a human IgG heavy chain Fc region extends from Cys226, or from Pro230, to the carboxyl-terminus of the heavy chain. However, antibodies produced by host cells may undergo post-translational cleavage of one or more, particularly one or two, amino acids from the C-terminus of the heavy chain. Therefore an antibody produced by a host cell by expression of a specific nucleic acid molecule encoding a full-length heavy chain may include the full-length heavy chain, or it may include a cleaved variant of the full-length heavy chain. This may be the case where the final two C-terminal amino acids of the heavy chain are glycine (G446) and lysine (K447, EU numbering system). Therefore, the C-terminal lysine (Lys447), or the C-terminal glycine (Gly446) and lysine (Lys447), of the Fc region may or may not be present. Amino acid sequences of heavy chains including an Fc region are denoted herein without C-terminal glycine-lysine dipeptide if not indicated otherwise. In one aspect, a heavy chain including an Fc region as specified herein, comprised in an antibody according to the invention, comprises an additional C-terminal glycine-lysine dipeptide (G446 and K447, EU numbering system). In one aspect, a heavy chain including an Fc region as specified herein, comprised in an antibody according to the invention, comprises an additional C-terminal glycine residue (G446, numbering according to EU index). Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, M D, 1991.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which might be non-identical in the sense that further components fused to each of the subunits (e.g. antigen binding moieties) are not the same. In some embodiments the modification promoting association comprises an amino acid mutation in the Fc domain, specifically an amino acid substitution. In a particular embodiment, the modification promoting association comprises a separate amino acid mutation, specifically an amino acid substitution, in each of the two subunits of the Fc domain.

"Framework" or "FR" refers to variable domain residues other than complementary determining regions (CDRs). The FR of a variable domain generally consists of four FR domains: FR1, FR2, FR3, and FR4. Accordingly, the CDR and FR sequences generally appear in the following sequence in VH (or VL): FR1-CDR-H1(CDR-L1)-FR2-CDR-H2(CDR-L2)-FR3-CDR-H3(CDR-L3)-FR4.

The terms "full length antibody", "intact antibody", and "whole antibody" are used herein interchangeably to refer to an antibody having a structure substantially similar to a native antibody structure or having heavy chains that contain an Fc region as defined herein.

The terms "host cell", "host cell line", and "host cell culture" are used interchangeably and refer to cells into which exogenous nucleic acid has been introduced, including the progeny of such cells. Host cells include "transformants" and "transformed cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3. In one aspect, for the VL, the subgroup is subgroup kappa I as in Kabat et al., supra. In one aspect, for the VH, the subgroup is subgroup III as in Kabat et al., supra.

A "humanized" antibody refers to a chimeric antibody comprising amino acid residues from non-human CDRs and amino acid residues from human FRs. In certain aspects, a humanized antibody will comprise substantially all of at least one, and typically two, variable domains, in which all or substantially all of the CDRs correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence and which determine antigen binding specificity, for example "complementarity determining regions" ("CDRs").

Generally, antibodies comprise six CDRs: three in the VH (CDR-H1, CDR-H2, CDR-H3), and three in the VL (CDR-L1, CDR-L2, CDR-L3). Exemplary CDRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, MD (1991)); and (c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)).

Unless otherwise indicated, the CDRs are determined according to Kabat et al., supra. One of skill in the art will understand that the CDR designations can also be determined according to Chothia, supra, McCallum, supra, or any other scientifically accepted nomenclature system.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain aspects, the individual or subject is a human.

An "isolated" antibody is one which has been separated from a component of its natural environment. In some aspects, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) methods. For a review of methods for assessment of antibody purity, see, e.g., Flatman et al., *J. Chromatogr. B* 848:79-87 (2007).

The term "nucleic acid molecule" or "polynucleotide" includes any compound and/or substance that comprises a polymer of nucleotides. Each nucleotide is composed of a base, specifically a purine- or pyrimidine base (i.e. cytosine (C), guanine (G), adenine (A), thymine (T) or uracil (U)), a sugar (i.e. deoxyribose or ribose), and a phosphate group. Often, the nucleic acid molecule is described by the sequence of bases, whereby said bases represent the primary structure (linear structure) of a nucleic acid molecule. The sequence of bases is typically represented from 5' to 3'. Herein, the term nucleic acid molecule encompasses deoxyribonucleic acid (DNA) including e.g., complementary DNA (cDNA) and genomic DNA, ribonucleic acid (RNA), in particular messenger RNA (mRNA), synthetic forms of DNA or RNA, and mixed polymers comprising two or more of these molecules. The nucleic acid molecule may be linear or circular. In addition, the term nucleic acid molecule includes both, sense and antisense strands, as well as single stranded and double stranded forms. Moreover, the herein described nucleic acid molecule can contain naturally occurring or non-naturally occurring nucleotides. Examples of non-naturally occurring nucleotides include modified nucleotide bases with derivatized sugars or phosphate backbone linkages or chemically modified residues. Nucleic acid molecules also encompass DNA and RNA molecules which are suitable as a vector for direct expression of an antibody of the invention in vitro and/or in vivo, e.g., in a host or patient. Such DNA (e.g., cDNA) or RNA (e.g., mRNA) vectors, can be unmodified or modified. For example, mRNA can be chemically modified to enhance the stability of the RNA vector and/or expression of the encoded molecule so that mRNA can be injected into a subject to generate the antibody in vivo (see e.g., Stadler et al, Nature Medicine 2017, published online 12 Jun. 2017, doi:10.1038/nm.4356 or EP 2 101 823 B1).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical composition.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable domain (VH), also called a variable heavy domain or a heavy chain variable region, followed by three constant heavy domains (CH1, CH2, and CH3). Similarly, from N- to C-terminus, each light chain has a variable domain (VL), also called a variable light domain or a light chain variable region, followed by a constant light (CL) domain.

A "blocking" antibody or an "antagonist" antibody is one that inhibits or reduces a biological activity of the antigen it binds. In some embodiments, blocking antibodies or antagonist antibodies substantially or completely inhibit the biological activity of the antigen. For example, the anti-PD-L1 antibodies of the invention block the signaling through PD-1 so as to restore a functional response by T-cells (e.g., proliferation, cytokine production, target cell killing) from a dysfunctional state to antigen stimulation.

An "agonist" or activating antibody is one that enhances or initiates signaling by the antigen to which it binds. In some embodiments, agonist antibodies cause or activate signaling without the presence of the natural ligand.

The term "package insert" is used to refer to instructions customarily included in commercial packages of therapeutic products, that contain information about the indications, usage, dosage, administration, combination therapy, contraindications and/or warnings concerning the use of such therapeutic products.

"No substantial cross-reactivity" means that a molecule (e.g., an antibody) does not recognize or specifically bind an antigen different from the actual target antigen of the molecule (e.g. an antigen closely related to the target antigen), particularly when compared to that target antigen. For example, an antibody may bind less than about 10% to less than about 5% to an antigen different from the actual target antigen, or may bind said antigen different from the actual target antigen at an amount consisting of less than about 10%, 9%, 8% 7%, 6%, 5%, 4%, 3%, 2%, 1%, 0.5%, 0.2%, or 0.1%, preferably less than about 2%, 1%, or 0.5%, and most preferably less than about 0.2% or 0.1% antigen different from the actual target antigen.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity for the purposes of the alignment. Alignment for purposes of determining percent amino acid sequence identity can be achieved in various ways that are within the skill in the art, for instance, using publicly available computer software such as BLAST, BLAST-2, Clustal W, Megalign (DNASTAR) software or the FASTA program package. Those skilled in the art can determine appropriate parameters for aligning sequences, including any algorithms needed to achieve maximal alignment over the full length of the sequences being compared. Alternatively, the percent identity values can be generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087 and is described in WO 2001/007611.

Unless otherwise indicated, for purposes herein, percent amino acid sequence identity values are generated using the ggsearch program of the FASTA package version 36.3.8c or later with a BLOSUM50 comparison matrix. The FASTA program package was authored by W. R. Pearson and D. J. Lipman (1988), "Improved Tools for Biological Sequence Analysis", PNAS 85:2444-2448; W. R. Pearson (1996) "Effective protein sequence comparison" Meth. Enzymol. 266:227-258; and Pearson et. al. (1997) Genomics 46:24-36 and is publicly available from www.fasta.bioch.virginia.edu/fasta_www2/fasta_down.shtml or www. ebi.ac.uk/Tools/sss/fasta. Alternatively, a public server accessible at fasta-.bioch.virginia.edu/fasta_www2/index.cgi can be used to compare the sequences, using the ggsearch (global protein: protein) program and default options (BLOSUM50; open: −10; ext: −2; Ktup=2) to ensure a global, rather than local, alignment is performed. Percent amino acid identity is given in the output alignment header The term "pharmaceutical composition" or "pharmaceutical formulation" refers to a preparation which is in such form as to permit the biological activity of an active ingredient contained therein to be effective, and which contains no additional components which are unacceptably toxic to a subject to which the pharmaceutical composition would be administered.

A "pharmaceutically acceptable carrier" refers to an ingredient in a pharmaceutical composition or formulation, other than an active ingredient, which is nontoxic to a subject. A pharmaceutically acceptable carrier includes, but is not limited to, a buffer, excipient, stabilizer, or preservative.

The term "PD-1 axis binding antagonist" is a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonists" is a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1106 described herein. In another specific aspect, a PD-1 binding antagonist is Merck 3745 described herein. In another specific aspect, a PD-1 binding antagonist is CT-01 1 described herein.

The term "PD-L1 binding antagonists" is a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is YW243.55.S70 described herein. In another specific aspect, an anti-PD-L1 antibody is MDX-1 105 described herein. In still another specific aspect, an anti-PD-L1 antibody is MPDL3280A described herein.

The term "PD-L2 binding antagonists" is a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g; enhancing effector responses to antigen recognition). In some embodiments, a PD-L2 binding antagonist is an immunoadhesin.

A "PD-1 oligopeptide", "PD-L1 oligopeptide" or "PD-L2 oligopeptide" is an oligopeptide that binds, preferably specifically, to a PD-1, PD-L1 or PD-L2 negative costimulatory polypeptide, respectively, including a receptor, ligand or signaling component, respectively, as described herein. Such oligopeptides may be chemically synthesized using known oligopeptide synthesis methodology or may be prepared and purified using recombinant technology. Such oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more. Such oligopeptides may be identified using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663, 143; PCT Publication Nos. WO 84/03506 and WO84/03564; Geysen et al., Proc. Natl. Acad. Sci. U.S.A., 81:3998-4002 (1984); Geysen et al, Proc. Natl. Acad. Sci. U.S.A., 82: 178-182 (1985); Geysen et al, in Synthetic Peptides as Antigens, 130-149 (1986); Geysen et al., J. Immunol. Metk, 102:259-274 (1987); Schoofs et al., J. Immunol., 140:61 1-616 (1988), Cwirla, S. E. et al. Proc. Natl. Acad. Sci. USA, 87:6378 (1990); Lowman, H. B. et al. Biochemistry, 30: 10832 (1991); Clackson, T. et al. Nature, 352: 624 (1991); Marks, J. D. et al., J. Mol. Biol., 222:581 (1991); Kang, A. S. et al. Proc. Natl. Acad. Sci. USA, 88:8363 (1991), and Smith, G. P., Current Opin. Biotechnol, 2:668 (1991).

The term "anergy" refers to the state of unresponsiveness to antigen stimulation resulting from incomplete or insufficient signals delivered through the T-cell receptor (e.g. increase in intracellular $Ca^{+2}$ in the absence of ras-activation). T cell anergy can also result upon stimulation with antigen in the absence of co-stimulation, resulting in the cell becoming refractory to subsequent activation by the antigen even in the context of costimulation. The unresponsive state can often be overridden by the presence of lnterleukin-2. Anergic T-cells do not undergo clonal expansion and/or acquire effector functions.

The term "exhaustion" refers to T cell exhaustion as a state of T cell dysfunction that arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T cells. Exhaustion prevents optimal control of infection and tumors. Exhaustion can result from both extrinsic negative regulatory pathways (e.g., immunoregulatory cytokines) as well as cell intrinsic negative regulatory (costimulatory) pathways (PD-1, B7-H3, B7-H4, etc.).

"Enhancing T-cell function" means to induce, cause or stimulate a T-cell to have a sustained or amplified biological function, or renew or reactivate exhausted or inactive T-cells. Examples of enhancing T-cell function include: increased secretion of y-interferon from $CD8^+$ T-cells, increased proliferation, increased antigen responsiveness (e.g., viral, pathogen, or tumor clearance) relative to such levels before the intervention. In one embodiment, the level of enhancement is as least 50%, alternatively 60%, 70%, 80%, 90%, 100%, 1 20%, 150%, 200%. The manner of measuring this enhancement is known to one of ordinary skill in the art.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

"Immunogenecity" refers to the ability of a particular substance to provoke an immune response. Tumors are immunogenic and enhancing tumor immunogenicity aids in the clearance of the tumor cells by the immune response. Examples of enhancing tumor immunogenicity include treatment with anti-PDL antibodies and a ME inhibitor.

"Sustained response" refers to the sustained effect on reducing tumor growth after cessation of a treatment. For example, the tumor size may remain to be the same or smaller as compared to the size at the beginning of the administration phase. In some embodiments, the sustained response has a duration at least the same as the treatment duration, at least 1. 5×, 2. O×, 2.5×, or 3. O× length of the treatment duration.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some aspects, antibodies of the invention are used to delay development of a disease or to slow the progression of a disease.

The term "cancer" as used herein refers to proliferative diseases, such as the cancer is colorectal cancer, sarcoma, head and neck cancer, squamous cell carcinoma, breast cancer, pancreatic cancer, gastric cancer, non-small-cell lung carcinoma, small-cell lung cancer and mesothelioma, including refractory versions of any of the above cancers, or a combination of one or more of the above cancers. In one embodiment, the cancer is colorectal cancer and optionally the chemotherapeutic agent is Irinotecan. In embodiments in which the cancer is sarcoma, optionally the sarcoma is chondrosarcoma, leiomyosarcoma, gastrointestinal stromal tumours, fibrosarcoma, osteosarcoma. liposarcoma or malignant fibrous histiocytoma.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three complementary determining regions (CDRs). (See, e.g., Kindt et al. *Kuby Immunology,* 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

As used herein, the term "antigen binding molecule" refers in its broadest sense to a molecule that specifically binds an antigenic determinant. Examples of antigen binding molecules are immunoglobulins and derivatives, e.g. fragments, thereof.

The term "antigen-binding site of an antibody" when used herein refer to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat et al., Sequences of Proteins of Immunological Interest, 5th ed., Public Health Service, National Institutes of Health, Bethesda, MD (1991) and/or those residues from a "hypervariable loop".

The term "monospecific" antibody as used herein denotes an antibody that has one or more binding sites each of which bind to the same epitope of the same antigen.

The term "bispecific" means that the antigen binding molecule is able to specifically bind to at least two distinct antigenic determinants. Typically, a bispecific antigen binding molecule comprises at least two antigen binding sites, each of which is specific for a different antigenic determinant. In certain embodiments the bispecific antigen binding molecule is capable of simultaneously binding two antigenic determinants, particularly two antigenic determinants expressed on two distinct cells.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising at least one antigen binding site that binds to FAP or DR5 as well as another, different antigen (see, US 2008/0069820, for example).

The term "valent" as used within the current application denotes the presence of a specified number of binding sites in an antibody molecule. As such, the terms "bivalent", "tetravalent", and "hexavalent" denote the presence of two binding sites, four binding sites, and six binding sites, respectively, in an antibody molecule. The bispecific antibodies according to the invention are at least "bivalent" and may be "trivalent" or "multivalent" (e.g. "tetravalent" or "hexavalent").

Antibodies of the present invention have two or more binding sites and are bispecific. That is, the antibodies may be bispecific even in cases where there are more than two binding sites (i.e. that the antibody is trivalent or multivalent). Bispecific antibodies of the invention include, for example, multivalent single chain antibodies, diabodies and triabodies, as well as antibodies having the constant domain structure of full length antibodies to which further antigen-binding sites (e.g., single chain Fv, a VH domain and/or a VL domain, Fab, or (Fab)2) are linked via one or more peptide-linkers. The antibodies can be full length from a single species, or be chimerized or humanized.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

As used herein, the expressions "cell", "cell line", and "cell culture" are used interchangeably and all such designations include progeny. Thus, the words "transfectants" and "transfected cells" include the primary subject cell and cultures derived there from without regard for the number of transfers. It is also understood that all progeny may not be precisely identical in DNA content, due to deliberate or inadvertent mutations. Variant progeny that have the same function or biological activity as screened for in the originally transformed cell are included.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

As used herein, the term "binding" or "specifically binding" refers to the binding of the antibody to an epitope of the antigen in an in-vitro assay, preferably in a surface plasmon resonance assay (SPR, BIAcore, GE-Healthcare Uppsala, Sweden). The affinity of the binding is defined by the terms ka (rate constant for the association of the antibody from the antibody/antigen complex), kD (dissociation constant), and KD (kD/ka). Binding or specifically binding means a binding affinity (KD) of $10^{-8}$ mol/l or less, preferably $10^{-9}$ M to $10^{-13}$ mol/l.

Binding of the antibody to the death receptor can be investigated by a BIAcore assay (GE-Healthcare Uppsala, Sweden). The affinity of the binding is defined by the terms ka (rate constant for the association of the antibody from the antibody/antigen complex), kD (dissociation constant), and KD (kD/ka)

"Reduced binding", for example reduced binding to an Fc receptor, refers to a decrease in affinity for the respective interaction, as measured for example by SPR. For clarity the term includes also reduction of the affinity to zero (or below the detection limit of the analytic method), i.e. complete abolishment of the interaction. Conversely, "increased binding" refers to an increase in binding affinity for the respective interaction.

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. Suitable assays to measure T cell activation are known in the art described herein.

A "target cell antigen" as used herein refers to an antigenic determinant presented on the surface of a target cell, for example a cell in a tumor such as a cancer cell or a cell of the tumor stroma. In particular "target cell antigen" refers to Folate Receptor 1. As used herein, the terms "first" and "second" with respect to antigen binding moieties etc., are used for convenience of distinguishing when there is more than one of each type of moiety.

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins referred to as antigens herein, e.g., PD-1 and PD-L1, can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants.

As used herein, the terms "engineer, engineered, engineering," particularly with the prefix "glyco-," as well as the term "glycosylation engineering" are considered to include any manipulation of the glycosylation pattern of a naturally occurring or recombinant polypeptide or fragment thereof. Glycosylation engineering includes metabolic engineering of the glycosylation machinery of a cell, including genetic manipulations of the oligosaccharide synthesis pathways to achieve altered glycosylation of glycoproteins expressed in cells. Furthermore, glycosylation engineering includes the effects of mutations and cell environment on glycosylation. In one embodiment, the glycosylation engineering is an alteration in glycosyltransferase activity. In a particular embodiment, the engineering results in altered glucosaminyltransferase activity and/or fucosyltransferase activity.

The combination therapies in accordance with the invention have a synergistic effect. A "synergistic effect" of two compounds is one in which the effect of the combination of the two agents is greater than the sum of their individual effects and is statistically different from the controls and the single drugs. In another embodiment, the combination therapies disclosed herein have an additive effect. An "additive effect" of two compounds is one in which the effect of the combination of the two agents is the sum of their individual effects and is statistically different from either the controls and/or the single drugs.

"LRRK2" refers to Leucine-rich repeat kinase 2, also known as dardarin and PARKS, and includes any native LRRK2 from any vertebrate source, including mammals such as primates (e.g. humans) non-human primates (e.g. cynomolgus monkeys) and rodents (e.g. mice and rats), unless otherwise indicated. The amino acid sequence of human LRRK2 is shown in Uniprot accession no. Q5S007 (version 174, SEQ ID NO:27). The term "LRRK2" encompasses "full-length," unprocessed LRRK2 as well as any form of LRRK2 that results from processing in the cell. The term also encompasses naturally occurring variants of LRRK2, e.g., splice variants or allelic variants.

The term "LRRK2 inhibitor", as used therein refers to compounds which target, decrease or inhibit LRRK2 kinase activity. In some embodiments, LRRK2 inhibitors have an IC50 value below 1 μM, below 500 nM, below 200 nM, below 100 nM, below 50 nM, below 25 nM, below 10 nM, below 5 nM, 2 nM or below 1 nM. In some embodiments, the LRRK2 inhibitor decreases LRRK2 kinase activity at least about 10%, at least about 20%, at least about 30%, at least about 40%, at least about 50%, at least about 60%, at least about 70%, at least about 75%, at least about 80%, at least about 85%, at least about 90%, at least about 95% or at least about 99%. IC50 values can for instance be measured according to the procedure described in WO2011151360. For example, an assay can be used to determine a compound's potency in inhibiting activity of LRRK2 by determining, $K_{iapp}$, IC50, or percent inhibition values. Briefly, in a polypropylene plate, LRRK2, fluorescently-labeled peptide substrate, ATP and test compound are incubated together. Using a LabChip 3000 (Caliper Life Sciences), after the reaction the substrate is separated by capillary electrophoresis into two populations: phosphorylated and unphosphorylated. The relative amounts of each can be quantitated by quantifying the fluorescence intensity.

Some kinase inhibitors described in the prior art are multitargeted kinase inhibitors (i.e. pan-kinase inhibitors), and hence, not selective for LRRK2. An example of such non-selective kinase inhibitor is sunitinib, a multitargeted receptor tyrosine kinase inhibitor (see for example Paetis et al, 2009). Inhibiting immune cell function by multitargeted kinase inhibition might be undesirable (see Broekman et al, 2011). Without being bound by theory, multitargeted kinase inhibition can lead to loss of function in relevant immune cells since, e.g. activation of T cells as herein described can be negatively affected by multitargeted kinase inhibition.

In preferred embodiments of the present invention, the LRRK2 inhibitor is not a multitargeted kinase inhibitor. In one embodiment a multitargeted kinase inhibitor at a concentration of 1 μM inhibits binding of more than 5, 6, 7, 8, 9, 10, 15, 20, 30, 40, 50, 60, 70, 80, 90, or 100 kinases to their ligand by 99% as compared to binding to their ligand without the inhibitor. In one embodiment, the LRRK2 inhibitor is not sunitinib.

In preferred embodiments of the invention, the LRRK2 inhibitor is selective. In one embodiment, the LRRK2 inhibitor has a high selectivity. Selective or having a high selectivity means that the LRRK2 inhibitor (at a physiologically relevant concentration) inhibits no or only few kinases other than LRRK2.

In one embodiment, the LRRK2 inhibitor (at a physiologically relevant concentration) inhibits less than 1, 2, 3, 4, 5, 6, 7, 8, 9, 10, 11, 12, 13, 14, 15, 16, 17, 18, 19, or 20 kinases other than LRRK2. In one embodiment, the LRRK2 inhibitor (at a physiologically relevant concentration) inhibits not more than 1, 2, 3, 4, 5, 6, 7, 8, 9, 10, 11, 12, 13, 14, 15, 16, 17, 18, 19, or 20 kinases. Kinases other than LRRK2 are herein referred to as unrelated kinases. A selectivity score S can be determined to quantify selectivity, as shown in Example 8. In one embodiment, the selectivity score S(65) of the inhibitor (e.g. the LRRK2 inhibitor) is defined as the ratio of number of kinases inhibited by 65% of binding to their ligand as compared to binding to their ligand without the inhibitor divided by the number of kinases tested. In one embodiment, the selectivity score S(90) of the inhibitor (e.g. the LRRK2 inhibitor) is defined as the ratio of number of kinases inhibited by 90% of binding to their ligand as compared to binding to their ligand without the inhibitor divided by the number of kinases tested. In one embodiment, the selectivity score S(99) of the inhibitor (e.g. the LRRK2 inhibitor) is defined as the ratio of number of kinases inhibited by 99% of binding to their ligand as compared to binding to their ligand without the inhibitor divided by the number of kinases tested. In one embodiment, the selectivity score S is determined for a specified concentration (e.g., 0.1 μM, 1 μM, or 10 μM) of the inhibitor (e.g. the LRRK2 inhibitor). Kinase—ligand binding (and inhibition thereof) can be measured using assays as known in the art and hereinbefore described and as described in Example 8.

In a preferred embodiment, determining the selectivity score comprises determining inhibition of kinase—ligand binding for a set of kinases. In one embodiment, the set of kinases comprises 50, 100, 150, 200, 250, 300, 350, 400, 450 or 500 (e.g. human) kinases. In one embodiment, the set of kinases comprises about 400 human kinases. In one embodiment, the set of kinases comprises 403 (human) kinases. In one embodiment, the set of kinases comprises 403 non-mutated human kinases.

In a preferred embodiment, the set of kinases comprises (or consists of) AAK1, ABL1, ABL2, ACVR1, ACVR1B, ACVR2A, ACVR2B, ACVRL1, ADCK3, ADCK4, AKT1, AKT2, AKT3, ALK, AMPK-alpha1, AMPK-alpha2, ANKK1, ARKS, ASK1, ASK2, AURKA, AURKB, AURKC, AXL, BIKE, BLK, BMPR1A, BMPR1B, BMPR2, BMX, BRAF, BRK, BRSK1, BRSK2, BTK, BUB1, CAMK1, CAMK1B, CAMK1D, CAMK1G, CAMK2A, CAMK2B, CAMK2D, CAMK2G, CAMK4, CAMKK1, CAMKK2, CASK, CDC2L1, CDC2L2, CDC2L5, CDK11, CDK2, CDK3, CDK4-cyclinD1, CDK4-cyclinD3, CDK5, CDK7, CDK8, CDK9, CDKL1, CDKL2, CDKL3, CDKL5, CHEK1, CHEK2, CIT, CLK1, CLK2, CLK3, CLK4, CSF1R, CSK, CSNK1A1, CSNK1A1L, CSNK1D, CSNK1E, CSNK1G1, CSNK1G2, CSNK1G3, CSNK2A1, CSNK2A2, CTK, DAPK1, DAPK2, DAPK3, DCAMKL1, DCAMKL2, DCAMKL3, DDR1, DDR2, DLK, DMPK, DMPK2, DRAK1, DRAK2, DYRK1A, DYRK1B, DYRK2, EGFR, EIF2AK1, EPHA1, EPHA2, EPHA3, EPHA4, EPHA5, EPHA6, EPHA7, EPHA8, EPHB1, EPHB2, EPHB3, EPHB4, EPHB6, ERBB2, ERBB3, ERBB4, ERK1, ERK2, ERK3, ERK4, ERK5, ERK8, ERN1, FAK, FER, FES, FGFR1, FGFR2, FGFR3, FGFR4, FGR, FLT1, FLT3, FLT4, FRK, FYN, GAK, GCN2 (Kin.Dom.2,S808G), GRK1, GRK2, GRK3, GRK4, GRK7, GSK3A, GSK3B, HASPIN, HCK, HIPK1, HIPK2, HIPK3, HIPK4, HPK1, HUNK, ICK, IGF1R, IKK-alpha, IKK-beta, IKK-epsilon, INSR, INSRR, IRAK1, IRAK3, IRAK4, ITK, JAK1 (JH1domain-catalytic), JAK1 (JH2domain-pseudokinase), JAK2 (JH1domain-catalytic), JAK3 (JH1domain-catalytic), JNK1, JNK2, JNK3, KIT, LATS1, LATS2, LCK, LIMK1, LIMK2, LKB1, LOK, LRRK2, LTK, LYN, LZK, MAK, MAP3K1, MAP3K15, MAP3K2, MAP3K3, MAP3K4, MAP4K2, MAP4K3, MAP4K4, MAP4K5, MAPKAPK2, MAPKAPK5, MARK1, MARK2, MARK3, MARK4, MAST1, MEK1, MEK2, MEK3, MEK4, MEK5, MEK6, MELK, MERTK, MET, MINK, MKK7, MKNK1, MKNK2, MLCK, MLK1, MLK2, MLK3, MRCKA, MRCKB, MST1, MST1R, MST2, MST3, MST4, MTOR, MUSK, MYLK, MYLK2, MYLK4, MYO3A, MYO3B, NDR1, NDR2, NEK1, NEK10, NEK11, NEK2, NEK3, NEK4, NEK5, NEK6, NEK7, NEK9, NIK, NIM1, NLK, OSR1, p38-alpha, p38-beta, p38-delta, p38-gamma, PAK1, PAK2, PAK3, PAK4, PAK6, PAK7, PCTK1, PCTK2, PCTK3, PDGFRA, PDGFRB, PDPK1, PFCDPK1 (P.falciparum), PFPKS (P.falciparum), PFTAIRE2, PFTK1, PHKG1, PHKG2, PIK3C2B, PIK3C2G, PIK3CA, PIK3CB, PIK3CD, PIK3CG, PIK4CB, PIKFYVE, PIM1, PIM2, PIM3, PIP5K1A, PIP5K1C, PIP5K2B, PIP5K2C, PKAC-alpha, PKAC-beta, PKMYT1, PKN1, PKN2, PKNB (M.tuberculosis), PLK1, PLK2, PLK3, PLK4, PRKCD, PRKCE, PRKCH, PRKCI, PRKCQ, PRKD1, PRKD2, PRKD3, PRKG1, PRKG2, PRKR, PRKX, PRP4, PYK2, QSK, RAF1, RET, RIOK1, RIOK2, RIOK3, RIPK1, RIPK2, RIPK4, RIPK5, ROCK1, ROCK2, ROS1, RPS6KA4 (Kin-.Dom.1-N-terminal), RPS6KA4 (Kin.Dom.2-C-terminal), RPS6KA5 (Kin.Dom.1-N-terminal), RPS6KA5 (Kin-.Dom.2-C-terminal), RSK1 (Kin.Dom.1-N-terminal), RSK1 (Kin.Dom.2-C-terminal), RSK2 (Kin.Dom.1-N-terminal), RSK2 (Kin.Dom.2-C-terminal), RSK3 (Kin.Dom.1-N-terminal), RSK3 (Kin.Dom.2-C-terminal), RSK4 (Kin.Dom.1-N-terminal), RSK4 (Kin.Dom.2-C-terminal), S6K1, SBK1, SGK, SgK110, SGK2, SGK3, SIK, SIK2, SLK, SNARK, SNRK, SRC, SRMS, SRPK1, SRPK2, SRPK3, STK16, STK33, STK35, STK36, STK39, SYK, TAK1, TAOK1, TAOK2, TAOK3, TBK1, TEC, TESK1, TGFBR1, TGFBR2, TIE1, TIE2, TLK1, TLK2, TNIK, TNK1, TNK2, TNNI3K, TRKA, TRKB, TRKC, TRPM6, TSSK1B, TSSK3, TTK, TXK, TYK2, TYRO3, ULK1, ULK2, ULK3, VEGFR2, VPS34, VRK2, WEE1, WEE2, WNK1, WNK2, WNK3, WNK4, YANK1, YANK2, YANK3, YES, YSK1, YSK4, ZAK, ZAP70.

In one embodiment, the LRRK2 inhibitor at concentration of 0.1 μM has a selectivity score (S65) of below 0.09, below 0.08, below 0.07, below 0.06, below 0.05, below 0.04, below 0.03, below 0.02, or below 0.01. In a preferred embodiment, the LRRK2 inhibitor at concentration of 0.1 μM has a selectivity score (S65) of below 0.05.

In one embodiment, the LRRK2 inhibitor at concentration of 1 μM has a selectivity score (S65) of below 0.35, below 0.3, below 0.25, below 0.2, below 0.15, below 0.1, below 0.05, below 0.04, below 0.03, below 0.02, or below 0.01. In a preferred embodiment, the LRRK2 inhibitor at concentration of 1 μM has a selectivity score (S65) of below 0.2.

In one embodiment, the LRRK2 inhibitor at concentration of 10 μM has a selectivity score (S65) of below 0.6, below 0.55, below 0.4, below 0.35, below 0.3, below 0.25, below 0.2, below 0.15, below 0.10, below 0.05, below 0.04, below 0.03 below 0.02, or below 0.01. In a preferred embodiment, the LRRK2 inhibitor at concentration of 10 μM has a selectivity score (S65) of below 0.5.

In one embodiment, the LRRK2 inhibitor at concentration of 0.1 μM has a selectivity score (S90) of below 0.035, below 0.03, below 0.025, below 0.02, below 0.015, below 0.01, below 0.005, below 0.004, below 0.003, below 0.002, or below 0.001. In a preferred embodiment, the LRRK2 inhibitor at concentration of 0.1 μM has a selectivity score (S90) of below 0.025.

In one embodiment, the LRRK2 inhibitor at concentration of 1 μM has a selectivity score (S90) of below 0.15, below 0.1, below 0.09, below 0.08, below 0.07, below 0.06, below 0.05, below 0.04, below 0.03, below 0.02, below 0.01 below 0.005, below 0.0025, or below 0.001. In a preferred embodiment, the LRRK2 inhibitor at concentration of 1 μM has a selectivity score (S90) of below 0.1.

In one embodiment, the LRRK2 inhibitor at concentration of 10 μM has a selectivity score (S90) of below 0.45, below 0.40, below 0.35, below 0.3, below 0.25, below 0.2, below 0.15, below 0.1, below 0.05, below 0.04, below 0.03, below 0.02, or below 0.01. In a preferred embodiment, the LRRK2 inhibitor at concentration of 10 μM has a selectivity score (S90) of below 0.35.

In one embodiment, the LRRK2 inhibitor at concentration of 0.1 μM has a selectivity score (S99) of below 0.015, below 0.014, below 0.013, below 0.012, below 0.011, below 0.010, below 0.009, below 0.008, below 0.007, below 0.006, below 0.005, below 0.004L below 0.003, below 0.002, or below 0.001. In a preferred embodiment, the LRRK2 inhibitor at concentration of 0.1 μM has a selectivity score (S99) of below 0.01.

In one embodiment, the LRRK2 inhibitor at concentration of 1 μM has a selectivity score (S99) of below 0.035, below 0.03, below 0.025, below 0.02, below 0.015, below 0.01, below 0.005, below 0.004, below 0.003, below 0.002, or below 0.001. In a preferred embodiment, the LRRK2 inhibitor at concentration of 1 μM has a selectivity score (S99) of below 0.01.

In one embodiment, the LRRK2 inhibitor at concentration of 10 μM has a selectivity score (S99) of below 0.2, below 0.15, below 0.1, below 0.09, below 0.08, below 0.07, below 0.06, below 0.05, below 0.04, below 0.03, below 0.02, below 0.01 below 0.005, below 0.0025, or below 0.001. In a preferred embodiment, the LRRK2 inhibitor at concentration of 10 μM has a selectivity score (S99) of below 0.1.

In one embodiment, the LRRK2 inhibitor at a concentration of 0.1 μM inhibits LRRK2 activity by more than 50%, more than 60%, more than 70%, more than 80%, more than 90%, more than 95%, or more than 97%. In a preferred embodiment, the LRRK2 inhibitor at a concentration of 0.1 μM inhibits LRRK2 activity by more than 97%.

In one embodiment, the LRRK2 inhibitor at a concentration of 1 μM inhibits LRRK2 activity with by than 50%, more than 60%, more than 70%, more than 80%, more than 90%, more than 95%, or more than 97%. In a preferred embodiment, the LRRK2 inhibitor at a concentration of 1 μM inhibits LRRK2 activity by more than 98%.

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain C1-C8 alkyl groups are methyl, ethyl, propyl, isopropyl, butyl, isobutyl, tert-butyl, the isomeric pentyls, the isomeric hexyls, the isomeric heptyls and the isomeric octyls, particularly methyl, ethyl, propyl, butyl and pentyl. Particular examples of alkyl are methyl, ethyl, isopropyl, butyl, isobutyl, tert-butyl and pentyl. Methyl, ethyl, propyl and ispropyl are particular examples of "alkyl" in the compound of formula (I).

The term "alkenyl", alone or in combination, signifies a straight-chain or branched-chain alkyl group with 2 to 6 carbon atoms, containing at least one double bond. Particular examples of "alkenyl" are ethenyl, propenyl, butenyl, pentenyl and hexenyl.

The term "alkynyl", alone or in combination, signifies a straight-chain or branched-chain alkyl group with 2 to 6 carbon atoms, containing at least one triple bond. Particular examples of "alkynyl" are ethynyl, propynyl, butynyl, pentynyl and hexynyl.

The term "cycloalkyl", alone or in combination, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl and cyclohexyl, cycloheptyl and cyclooctyl. A particular example of "cycloalkyl" is cyclopropyl.

The term "heterocycle" or "heterocylcyl", alone or in combination, signifies a ring system with 3 to 8 carbon atoms and 1 to 4 heteroatoms, wherein the heterocycle can be aromatic, and wherein the heterocycle can be monocyclic or bicyclic. Examples of "heterocyclyl" are morpholinyl, piperidinyl, pyrrolidinyl, pyrrolidinone-yl, octahydro-pyrido[1,2-a]pyrazin-2-yl, azetidinyl, piperazinyl, 3-oxa-8-aza-bicyclo[3.2.1]oct-8-yl, 2-oxa-5-aza-bicyclo[2.2.1]hept-5-yl, 8-oxa-3-aza-bicyclo[3.2.1]oct-3-yl, oxa-6-aza-spiro[3.3]hept-6-yl, [1,4]oxazepan-4-yl, 1-(2-oxa-5-aza-bicyclo[2.2.1]hept-5-yl), dioxanyl, tetrahydropyranyl, pyridinyl, 8-oxabicyclo[3.2.1]octan-3-yl, pyrimidinyl, tetrahydrofuranyl, piperidinone, oxetanyl, pyridazinyl, pyrazolyl, tetrazolyl, triazolyl, oxadiazolyl, imidazolyl, thiazolyl, oxazolyl, isoxazolyl, dihydrobenzofuranyl, dihydrobenzodioxine and hexahydro-pyrrolo[1,2-]pyrazinyl. Particular examples of "heterocycle" are pyrimidine, pyrazole, 3H-pyrrolo[2,3-d]pyrimidine and morpholino, more particular examples of "heterocycle" are pyrimidine and morpholino. A particular example of "heterocycle" is pyrimidine. In some embodiments of the invention heterocyclyl is optionally substituted with one, two, three or four substituents independently selected from deuterium, hydroxy, alkyl, hydroxyalkyl, halo, alkoxy, cyano, alkylcarbonyl, haloalkyl, alkylsulfonyl, (cycloalkyl)carbonyl, oxetanyl, alkylpiperidinyl, dialkylamino, alkoxyalkyl, alkyl(cycloalkyl)carbonyl, dioxolanylalkyl, (di alkyl amino)carbonyl, morpholinylcarbonyl, alkylaminocarbonyl and (halopyrrolidinyl)carbonyl.

The term "heteroatom", alone or in combination, signifies an atom different from carbon or hydrogen. Particular examples of heteroatoms are oxygen, nitrogen and sulfur, more particular oxygen and nitrogen.

The term "alkoxy" or "alkyloxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert-butoxy. Particular examples of "alkoxy" are methoxy and ethoxy, more particular methoxy.

The term "cycloalkoxy" or "cycloalkyloxy", alone or in combination, signifies a group of the formula cycloalkyl-O— in which the term "cycloalkyl" has the previously given significance. Particular examples of "cycloalkoxy" are cyclopropyloxy, cyclobutyloxy and cyclopentyloxy, more particular cyclopropyloxy.

The term "oxy", alone or in combination, signifies the —O— group.

The terms "halogen" or "halo", alone or in combination, signifies fluorine, chlorine, bromine or iodine and particularly fluorine, chlorine or bromine, more particularly fluorine or chlorine. The term "halo", in combination with another group, denotes the substitution of said group with at least one halogen, particularly substituted with one to five halogens, particularly one to four halogens, i.e. one, two, three or four halogens.

The term "haloalkyl", alone or in combination, denotes an alkyl group substituted with at least one halogen, particularly substituted with one to five halogens, particularly one to three halogens. Particular examples of "haloalkyl" are chloromethyl, chloroethyl, chloropropyl, fluoromethyl, difluoromethyl, trifluoromethyl, fluoroethyl, difluoroethyl, trifluoroethyl, fluoropropyl and fluorobutyl, more particular chloromethyl, fluoromethyl and trifluoromethyl.

The term "haloalkoxy", alone or in combination, denotes an alkoxy group substituted with at least one halogen, particularly substituted with one to five halogens, particularly one to three halogens. Particular examples of "haloalkyoxy" are chloromethoxy, chloroethoxy, chloropropoxy, fluoromethoxy, difluoromethoxy, trifluoromethoxy, fluoroethoxy, difluoroethoxy, trifluoroethoxy, fluoropropoxy and fluorobutoxy, more particular chloromethoxy, fluoromethoxy and trifluoromethoxy.

The terms "hydroxyl" and "hydroxy", alone or in combination, signify the —OH group.

The term "carbonyl", alone or in combination, signifies the —C(O)— group.

The terms "carboxy or "hydroxycarbonyl", alone or in combination, are interchangeable and signify the —C(O)—OH group.

The term "alkoxycarbonyl", alone or in combination, signifies the —C(O)—OR group, wherein R is alkyl as defined herein.

The term "amino", alone or in combination, signifies the primary amino group (—$NH_2$), the secondary amino group (—NH—), or the tertiary amino group (—N—).

The term "aminocarbonyl" alone or in combination, signifies the —C(O)—R— group, wherein R is amino as defined herein.

The terms "alkylaminocarbonyl" or "(alkylamino)carbonyl, alone or in combination, signify the —C(O)—NHR— group, wherein R is alkyl as defined herein.

The term "dialkylamino" alone or in combination, signifies the amino group substituted with two alkyl, wherein the amino and the alkyl are as defined herein.

The term "alkylamino", alone or in combination, signifies an alkyl group attached to an amino group. Particular examples of "alkylamino" are methylamino and ethylamino.

The term "sulfonyl", alone or in combination, signifies the —$SO_2$— group.

The term "alkylsulfonyl", alone or in combination, signifies the —$SO_2$—R group, wherein R is alkyl as defined herein.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3rd Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

II. Compositions and Methods

In one aspect, the invention is based on the use of a therapeutic combination of a PD-1 axis binding antagonist and a LRRK1 inhibitor, e.g., for the treatment of cancer.

Combination Therapies of a PD-1 Axis Binding Antagonist and a LRRK2 Inhibitor Broadly, the present invention relates to PD-1 axis binding antagonist and their use in combination with a LRRK2 inhibitor. The advantage of the combination over monotherapy is that the PD-1 axis binding antagonist enhances T cell function by reducing T cell exhaustion while the LRRK2 inhibitor increases presentation of tumor antigen, e.g., on MHC I complexes of an immune cell.

In one aspect, provided herein is a method for treating or delaying progression of cancer in an individual comprising administering to the individual an effective amount of a PD-1 axis binding antagonist and a LRRK2 inhibitor. In some embodiments, the treatment results in sustained response in the individual after cessation of the treatment. The methods of this invention may find use in treating conditions where enhanced immunogenicity is desired such as increasing tumor immunogenicity for the treatment of cancer. A variety of cancers may be treated, or their progression may be delayed.

In some embodiments, the individual has endometrial cancer. The endometrial cancer may be at early stage or late state. In some embodiments, the individual has melanoma. The melanoma may be at early stage or at late stage. In some embodiments, the individual has colorectal cancer. The colorectal cancer may be at early stage or at late stage. In some embodiments, the individual has lung cancer, e.g., non-small cell lung cancer. The non-small cell lung cancer may be at early stage or at late stage. In some embodiments, the individual has pancreatic cancer. The pancreatic cancer may be at early stage or late state. In some embodiments, the individual has a hematological malignancy. The hematological malignancy may be early stage or late stage. In some embodiments, the individual has ovarian cancer. The ovarian cancer may be at early stage or at late stage. In some embodiments, the individual has breast cancer. The breast cancer may be at early stage or at late stage. In some embodiments, the individual has renal cell carcinoma. The renal cell carcinoma may be at early stage or at late stage.

In some embodiments, the individual is a mammal, such as domesticated animals (e.g., cows, sheep, cats, dogs, and horses), primates (e.g., humans and non-human primates such as monkeys), rabbits, and rodents (e.g., mice and rats). In some embodiments, the individual treated is a human.

In another aspect, provided herein is a method of enhancing immune function in an individual having cancer comprising administering an effective amount a PD-1 axis binding antagonist and a LRRK2 inhibitor.

In some embodiments, the T cells in the individual have enhanced priming, activation, proliferation and/or effector function relative to prior to the administration of the PD-1 axis antagonist and the LRRK2 inhibitor. In some embodiments, the T cell effector function is secretion of at least one of IL-2, IFN-γ and TNF-α. In one embodiment, administering of an anti-PDL-1 antibody and a LRRK2 inhibitor results in increased T cell secretion of IL-2, IFN-γ and TNF-α. In some embodiments, the T cell is a CD8+ T cell. In some embodiments, the T cell priming is characterized by elevated CD44 expression and/or enhanced cytolytic activity in CD8 T cells. In some embodiments, the CD8 T cell activation is characterized by an elevated frequency of CD8-positive T cells. In some embodiments, the CD8 T cell is an antigen-specific T-cell. In some embodiments, the immune evasion by signaling through PD-L1 surface expression is inhibited. In some embodiments, the cancer has elevated levels of T-cell infiltration.

In some embodiments, the combination therapy of the invention comprises administration of a PD-1 axis binding antagonist and a LRRK2 inhibitor. The PD-1 axis binding antagonist and the LRRK2 inhibitor may be administered in any suitable manner known in the art. For example, a PD-1 axis binding antagonist and a LRRK2 inhibitor may be administered sequentially (at different times) or concurrently (at the same time). In some embodiments, the PD-1 axis binding antagonist is administered continuously. In some embodiments, the PD-1 axis binding antagonist is administered intermittently. In some embodiments, the PD-1 axis binding antagonist is administered before administration of the LRRK2 inhibitor. In some embodiments, the PD-1 axis binding antagonist is administered simultaneously with administration of the LRRK2 inhibitor. In some embodiments, the PD-1 axis binding antagonist is administered after administration of the LRRK2 inhibitor.

In some embodiments, provided is a method for treating or delaying progression of cancer in an individual comprising administering to the individual an effective amount of a PD-1 axis binding antagonist and a LRRK2 inhibitor, further comprising administering an additional therapy. The additional therapy may also be radiation therapy, surgery (e.g., lumpectomy and a mastectomy), chemotherapy, gene therapy, DNA therapy, viral therapy, R A therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as antinausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PI3K/A T/mTOR pathway, HSP90 inhibitor, tubulin inhibitor, apoptosis inhibitor, and/or chemopreventative agent. The additional therapy may be one or more of the chemotherapeutic agents described hereabove.

The PD-1 axis binding antagonist and the LRRK2 inhibitor may be administered by the same route of administration or by different routes of administration. In some embodiments, the PD-1 axis binding antagonist is administered intravenously, intramuscularly, subcutaneously, topically, orally, transdermally, intraperitoneally, intraprbitally, by implantation, by inhalation, intrathecally, intraventricularly, or intranasally. In some embodiments, the PD-1 axis binding antagonist is administered orally, intravenously, intramuscularly, subcutaneously, topically, orally, transdermally, intraperitoneally, intraorbitally, by implantation, by inhalation, intrathecally, intraventricularly, or intranasally. An effective amount of the PD-1 axis binding antagonist and the LRRK2 inhibitor may be administered for prevention or treatment of disease. The appropriate dosage of the PD-1 axis binding antagonist and/or the LRRK2 inhibitor may be determined based on the type of disease to be treated, the type of the PD-1 axis binding antagonist and/or the LRRK2 inhibitor, the severity and course of the disease, the clinical condition of the individual, the individual's clinical history and response to the treatment, and the discretion of the attending physician.

Any of the PD-1 axis binding antagonists and the LRRK2 inhibitors known in the art or described below may be used in the methods.

In a further aspect, the present invention provides a pharmaceutical composition comprising a PD-1 axis binding antagonists as described herein, a LRRK1 inhibitor as described herein and a pharmaceutically acceptable carrier.

In a further aspect, the invention provides for a kit comprising a PD-1 axis binding antagonist, and a package insert comprising instructions for using the PD-1 axis binding antagonist with a LRRK2 inhibitor to treat or delay progression of cancer in an individual.

In a further aspect, the invention provides for a kit comprising a PD-1 axis binding antagonist and a LRRK2 inhibitor, and a package insert comprising instructions for using the PD-1 axis binding antagonist and the LRRK2 inhibitor to treat or delay progression of cancer in an individual.

In one of the embodiments, the PD-1 axis binding antagonist is an anti-PD-1 antibody or an anti-PDL-1 antibody. In one embodiment, the PD-1 axis binding antagonist is an anti-PD-1 immunoadhesin.

In a further aspect, the invention provides a kit comprising:

(i) a first container comprising a composition which comprises a LRRK2 inhibitor as described herein; and (ii) a second container comprising a composition comprising a PD-1 axis binding antagonist.

Exemplary LRRK2 Inhibitors for Use According to the Invention

In some embodiments, the LRRK2 inhibitor has a molecular weight of 200-900 dalton. In some embodiments, the LRRK2 inhibitor has a molecular weight of 400-700 dalton. In some embodiments, the LRRK2 inhibitor has an IC50 value below 1 μM, below 500 nM, below 200 nM, below 100 nM, below 50 nM, below 25 nM, below 10 nM, below nM, 2 nM or below 1 nM. In a preferred embodiment, the LRRK2 inhibitor has an IC50 value below 50 nM. In some embodiments, the LRRK2 inhibitor has an $K_{iapp}$ value below 1 μM, below 500 nM, below 200 nM, below 100 nM, below 50 nM, below 25 nM, below nM, below 5 nM, 2 nM or below 1 nM. In a preferred embodiments, the LRRK2 inhibitor has an $K_{iapp}$ value below 50 nM.

In one embodiment, an inhibitor having an IC50 value for LRRK2 of below 100 nM is not considered a LRRK2 inhibitor.

In some embodiments, the LRRK2 inhibitor is selected from the compounds disclosed in patent applications WO2011151360, WO2012062783, WO2013079493, WO2013079495, WO2013079505, WO2013079494, WO2013079496, WO2013164321 or WO2013164323.

In some embodiments, the LRRK2 inhibitor is selected from the compounds disclosed in the patent application WO2011151360. In some embodiments, the LRRK2 inhibitor is selected from the compounds disclosed in the patent application WO2012062783.

In some embodiments, the LRRK2 inhibitor is selected from the compounds specifically exemplified in patent applications WO2011151360, WO2012062783, WO2013079493, WO2013079495, WO2013079505, WO2013079494, WO2013079496, WO2013164321 or WO2013164323.

In some embodiments, the LRRK2 inhibitor is selected from the compounds specifically exemplified in the patent application WO2011151360. In some embodiments, the LRRK2 inhibitor is selected from the compounds specifically exemplified in the patent application WO2012062783.

In some embodiments, the LRRK2 inhibitor comprises an aromatic cycle, which is attached to a heterocycle via a nitrogen atom, wherein the nitrogen atom can form part of the heterocycle.

In some embodiments, the LRRK2 inhibitor comprises an aromatic cycle, which is attached to a heterocycle via a nitrogen atom, wherein the nitrogen atom can form part of the heterocycle, and wherein the heterocycle comprises two heteroatoms.

In some embodiments, the LRRK2 inhibitor is a compound of formula (I)

(I)

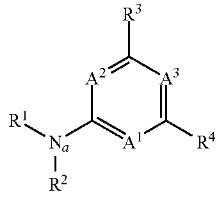

wherein, $A^1$ is —N— or —$CR^5$—;

$A_2$ is —N— or —$CR^6$—;

$A_3$ is —N— or —$CR^7$—;

$N_a$ is —N—;

$R^1$ is alkylamino(haloalkylpyrimidinyl), cyanoalkyl(alkylpyrazolyl), alkylamino(halopyrimidinyl), oxetanyl (halopiperidinyl)halopyrazolyl, halo(N-alkyl-3H-pyrrolo[2,3-d]pyrimidine-amine), 5,11-dialkylpyrimido[4,5-b][1,4]benzodiazepin-6-one, phenyl optionally substituted with one, two or three substituents independently selected from $R_a$, pyrazolyl optionally substituted with one, two or three substituents independently selected from $R_a$, or a condensed bicyclic system optionally substituted with one, two or three substituents independently selected from $R_a$;

$R_a$ is (heterocyclyl)carbonyl, (heterocyclyl)alkyl, heterocyclyl, alkoxy, aminocarbonyl, alkylaminocarbonyl, amino(alkylamino)carbonyl, oxetanylaminocarbonyl, (tetrahydropyranyl)aminocarbonyl, (dialkylamino)carbonyl, (cycloalkylamino)carbonyl, hydroxy, haloalkoxy, cycloalkoxy, (hydroxyalkyl)aminocarbonyl, (alkoxyalkyl)aminocarbonyl, (alkylpiperidinyl)aminocarbonyl, (alkoxyalkyl)alkylaminocarbonyl, (hydroxyalkyl)(alkylamino)carbonyl, (cyanocycloalkyl)aminocarbonyl, (cycloaklyl)alkylaminocarbonyl, (haloazetidinyl)aminocarbonyl, (haloalkyl)aminocarbonyl, morpholinylcarbonylalkyl, morpholinylalkyl, alkyl, fluorine, chlorine, bromine, iodine, (perdeuteromorpholinyl)carbonyl, (halocycloalkyl)aminocarbonyl, oxetanyloxy, (cycloalkyl)alkoxy, cycloalkyl, cyano, alkenyl, alkynyl, alkoxyalkyl, hydroxyalkyl, (cycloalkyl)alkyl, alkylsulfonyl, phenyl, haloalkyl, cyanophenyl, cycloalkylsulfonyl, cyanoalkyl, alkylsulfonylphenyl, (dialkylamino)carbonylphenyl, halophenyl, (alkyloxetanyl)alkyl, (dialkylamino)phenyl, (cycloalkylsulfonyl)phenyl, alkoxycycloalkyl, (alkylamino)carbonylalkyl, pyridazinylalkyl, pyrimidinylalkyl, (alkylpyrazolyl)alkyl, triazolylalkyl, (alkyltriazolyl)alkyl, hydroxycycloalkyl, (oxadiazolyl)alkyl, (dialkylamino)carbonylalkyl, pyrrolidinylcarbonylalkyl, cyanocycloalkyl, alkoxycarbonylalkyl, (haloalkyl)aminocarbonylalkyl, (cycloalkyl)alkylaminocarbonylalkyl, (alkylamino)carbonylcycloalkyl, alkylpiperidinyl(alkylamino)carbonyl, alkylpyrazolyl(alkylamino)carbonyl, (hydroxycycloalkyl)alkylaminocarbonyl, (hydroxycycloalkyl)alkyl, (dialkylimidazolyl)alkyl, (alkyloxazolyl)alkyl, alkoxyalkylsulfonyl, hydroxycarbonyl, morpholinylsulfonyl or alkyl(oxadiazolyl)alkyl, $R^2$ is alkyl or hydrogen;

or $R^1$ and $R^2$ together with $N_a$ form a morpholino optionally substituted with one, two or three alkyl;

$R^3$ and $R^4$ are independently selected from alkoxy, cycloalkylamino, (cycloalkyl)alkylamino, (tetrahydrofuranyl)alkylamino, alkoxyalkylamino, (tetrahydropyranyl)amino, (tetrahydropyranyl)oxy, (tetrahydropyranyl)alkylamino, haloalkylamino, piperidinyl, pyrrolidinyl, (oxetanyl)oxy, haloalkoxy, hydrogen, halogen, alkylamino, morpholinyl and alkyl(cycloalkyloxy)indazolyl;

or $R^3$ is hydrogen, and $R^4$ together with $R^5$ form a pyrrolyl substituted with $R^8$, wherein the pyrrolyl is fused to the aromatic cycle comprising $A^1$, $A^2$ and $A^3$;

$R^5$ and $R^6$ are independently selected from hydrogen and alkyloxy;

$R^7$ is hydrogen, halogen, alkyl, cycloalkyl, alkenyl, alkynyl, cyano, haloalkoxy, (cycloalkyl)alkyl, haloalkyl, (alkylpiperazinyl)piperidinylcarbonyl or morpholinocarbonyl; and $R^8$ is pyrrolyl substituted with cyano(alkylpyrrolyl) or cyanophenyl;

or a pharmaceutically acceptable salt thereof.

In some embodiments, the LRRK2 inhibitor is a compound of formula (I)

(I)

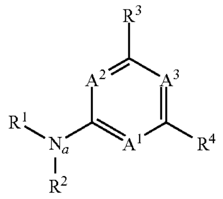

wherein, $A^1$ is —N— or —$CR^5$—;

$A^2$ is —N— or —$CR^6$—;

$A^3$ is —N— or —$CR^7$—;

$N_a$ is —N—;

$R^1$ is alkylamino(haloalkylpyrimidinyl), cyanoalkyl(alkylpyrazolyl), alkylamino(halopyrimidinyl), oxetanyl(halopiperidinyl)halopyrazolyl, halo(N-alkyl-3H-pyrrolo[2,3-d]pyrimidine-amine), 5,11-dialkylpyrimido[4,5-b][1,4]benzodiazepin-6-one, phenyl optionally substituted with one, two or three substituents independently selected from $R_a$, pyrazolyl optionally substituted with one, two or three substituents independently selected from $R_a$, or a condensed bicyclic system optionally substituted with one, two or three substituents independently selected from $R_a$;

$R_a$ is (heterocyclyl)carbonyl, (heterocyclyl)alkyl, heterocyclyl, alkoxy, aminocarbonyl, alkylaminocarbonyl, amino(alkylamino)carbonyl, oxetanylaminocarbonyl, (tetrahydropyranyl)aminocarbonyl, (dialkylamino)carbonyl, (cycloalkylamino)carbonyl, hydroxy, haloalkoxy, cycloalkoxy, (hydroxyalkyl)aminocarbonyl, (alkoxyalkyl)aminocarbonyl, (alkylpiperidinyl)aminocarbonyl, (alkoxyalkyl)alkylaminocarbonyl, (hydroxyalkyl)(alkylamino)carbonyl, (cyanocycloalkyl)aminocarbonyl, (cycloaklyl)alkylaminocarbonyl, (haloazetidinyl)aminocarbonyl, (haloalkyl)aminocarbonyl, morpholinylcarbonylalkyl, morpholinylalkyl, alkyl, fluorine, chlorine, bromine, iodine, (perdeuteromorpholinyl)carbonyl, (halocycloalkyl)aminocarbonyl, oxetanyloxy, (cycloalkyl)alkoxy, cycloalkyl, cyano, alkenyl, alkynyl, alkoxyalkyl, hydroxyalkyl, (cycloalkyl)alkyl, alkylsulfonyl, phenyl, haloalkyl, cyanophenyl, cycloalkylsulfonyl, cyanoalkyl, alkylsulfonylphenyl, (dialkylamino)carbonylphenyl, halophenyl, (alkyloxetanyl)alkyl, (dialkylamino)phenyl, (cycloalkylsulfonyl)phenyl, alkoxycycloalkyl, (alkylamino)carbonylalkyl, pyridazinylalkyl, pyrimidinylalkyl, (alkylpyrazolyl)alkyl, triazolylalkyl, (alkyltriazolyl)alkyl, hydroxycycloalkyl, (oxadiazolyl)alkyl, (dialkylamino)carbonylalkyl, pyrrolidinylcarbonylalkyl, cyanocycloalkyl, alkoxycarbonylalkyl, (haloalkyl)aminocarbonylalkyl, (cycloalkyl)alkylaminocarbonylalkyl, (alkylamino)carbonylcycloalkyl, alkylpiperidinyl(alkylamino)carbonyl, alkylpyrazolyl(alkylamino)carbonyl, (hydroxycycloalkyl)alkylaminocarbonyl, (hydroxycycloalkyl)alkyl, (dialkylimidazolyl)alkyl, (alkyloxazolyl)alkyl, alkoxyalkylsulfonyl, hydroxycarbonyl, morpholinylsulfonyl or alkyl(oxadiazolyl)alkyl, $R^2$ is alkyl or hydrogen;

or $R^1$ and $R^2$ together with $N_a$ form a morpholino optionally substituted with one, two or three alkyl;

$R^3$ and $R^4$ are independently selected from alkoxy, cycloalkylamino, (cycloalkyl)alkylamino, (tetrahydrofuranyl)alkylamino, alkoxyalkylamino, (tetrahydropyranyl)amino, (tetrahydropyranyl)oxy, (tetrahydropyranypalkylamino, haloalkylamino, piperidinyl, pyrrolidinyl, (oxetanyl)oxy, haloalkoxy, hydrogen, halogen, alkylamino, morpholinyl and alkyl(cycloalkyloxy)indazolyl;

or $R^3$ is hydrogen, and $R^4$ together with $R^5$ form a pyrrolyl substituted with $R^8$, wherein the pyrrolyl is fused to the aromatic cycle comprising $A^1$, $A^2$ and $A^3$;

$R^5$ and $R^6$ are independently selected from hydrogen and alkyloxy;

$R^7$ is hydrogen, halogen, alkyl, cycloalkyl, alkenyl, alkynyl, cyano, haloalkoxy, (cycloalkyl)alkyl, haloalkyl, (alkylpiperazinyl)piperidinylcarbonyl or morpholinocarbonyl; and $R^8$ is pyrrolyl substituted with cyano(alkylpyrrolyl) or cyanophenyl;

or a pharmaceutically acceptable salt thereof, wherein the LRRK2 inhibitor is not (i) a multitargeted kinase inhibitor, or (ii) sunitinib.

In some embodiments, the LRRK2 inhibitor is a compound of formula (I)

(I)

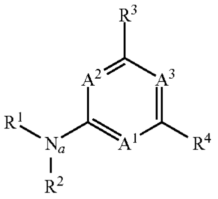

wherein, $A^1$ is —N— or —$CR^5$—;

$A^2$ is —N— or —$CR^6$—;

$A^3$ is —N— or —$CR^7$—;

$N_a$ is —N—;

$R^1$ is alkylamino(haloalkylpyrimidinyl), cyanoalkyl(alkylpyrazolyl), alkylamino(halopyrimidinyl), oxetanyl (halopiperidinyl)halopyrazolyl, halo(N-alkyl-3H-pyrrolo[2,3-d]pyrimidine-amine) or 5,11-dialkylpyrimido [4,5-b][1,4]benzodiazepin-6-one;

$R^2$ is hydrogen;

or $R^1$ and $R^2$ together with $N_a$ form a morpholino optionally substituted with one, two or three alkyl;

$R^3$ and $R^4$ are independently selected from hydrogen, halogen, alkylamino, morpholinyl and alkyl(cycloalkyloxy)indazolyl;

or $R^3$ is hydrogen, and $R^4$ together with $A^1$ form a pyrrolyl substituted with $R^8$, wherein the pyrrolyl is fused to the aromatic cycle comprising $A^1$, $A^2$ and $A^3$;

$R^5$ and $R^6$ are independently selected from hydrogen and alkyloxy;

$R^7$ is haloalkyl, (alkylpiperazinyl)piperidinylcarbonyl or morpholinocarbonyl; and $R^8$ is pyrrolyl substituted with cyano(alkylpyrrolyl) or cyanophenyl;

or a pharmaceutically acceptable salt thereof.

In some embodiments, the LRRK2 inhibitor is a compound of formula ($I_a$)

($I_a$)

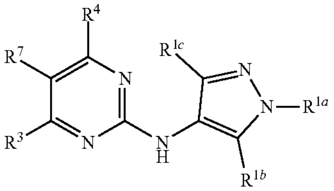

wherein $R^{1a}$ is cyanoalkyl or oxetanyl(halopiperidinyl).

$R^{1b}$ and $R^{1c}$ are independently selected from hydrogen, alkyl and halogen;

$R^3$ and $R^4$ are independently selected from hydrogen and alkylamino; and $R^7$ is haloalkyl;

or a pharmaceutically acceptable salt thereof.

In some embodiments, the LRRK2 inhibitor is a compound of formula ($I_b$)

wherein ($I_b$)

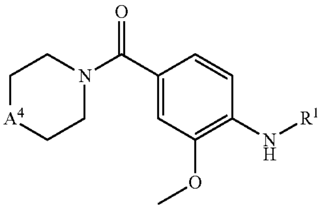

$R^1$ is alkylamino(halopyrimidinyl), halo(N-alkyl-3H-pyrrolo[2,3-d]pyrimidine-amine) or 5,11-dialkylpyrimido [4,5-b][1,4]benzodiazepin-6-one;

$R^3$ is halogen;

$A^4$ is —O— or —$CR^9$—; and $R^9$ is alkylpiperazinyl;

or a pharmaceutically acceptable salt thereof.

In some embodiments, the LRRK2 inhibitor is a compound of formula ($I_c$)

($I_c$)

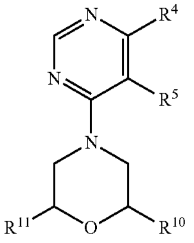

wherein, $R^4$ is alkyl(cycloalkyloxy)indazolyl, and $R^5$ is hydrogen;

or $R^4$ together with $R^5$ forms a pyrrolyl substituted with $R^8$, wherein the pyrrolyl is fused to the pyrimidine of the compound of formula ($I_c$);

$R^8$ is pyrrolyl substituted with cyano(alkylpyrrolyl) or cyanophenyl; and $R^{10}$ and $R^{11}$ are independently selected from hydrogen and alkyl;

or a pharmaceutically acceptable salt thereof.

In some embodiments, the LRRK2 inhibitor is selected from

[4-[[4-(ethylamino)-5-(trifluoromethyl)pyrimidin-2-yl]amino]-2-fluoro-5-methoxy-phenyl]-morpholino-methanone (7915);

2-methyl-2-[3-methyl-4-[[4-(methylamino)-5-(trifluoromethyl)pyrimidin-2-yl]amino]pyrazol-1-yl]propanenitrile;

N2-[5-chloro-1-[3-fluoro-1-(oxetan-3-yl)-4-piperidyl]pyrazol-4-yl]-N4-methyl-5-(trifluoromethyl)pyrimidine-2,4-diamine (9605);

[4-[[5-chloro-4-(methylamino)pyrimidin-2-yl]amino]-3-methoxy-phenyl]-morpholino-methanone (HG-10-102-01);

[4-[[5-chloro-4-(methylamino)-3H-pyrrolo[2,3-d]pyrimidin-2-yl]amino]-3-methoxy-phenyl]-morpholino-methanone (JH-II-127);

2-[2-methoxy-4-[4-(4-methylpiperazin-1-yl)piperidine-1-carbonyl]anilino]-5,11-dimethyl-pyrimido[4,5-b][1,4]benzodiazepin-6-one (LRRK2-IN-1);

3-(4-morpholino-7H-pyrrolo[2,3-d]pyrimidin-5-yl)benzonitrile (PF-06447475);

cis-2,6-dimethyl-4-[6-[5-(1-methylcyclopropoxy)-1H-indazol-3-yl]pyrimidin-4-yl]morpholine (MLi-2); and 1-methyl-4-(4-morpholino-7H-pyrrolo[2,3-d]pyrimidin-5-yl)pyrrole-2-carbonitrile;

or a pharmaceutically acceptable salt thereof.

In some embodiments, the LRRK2 inhibitor is selected from

[4-[[4-(ethylamino)-5-(trifluoromethyl)pyrimidin-2-yl]amino]-2-fluoro-5-methoxy-phenyl]-morpholino-methanone;

N2-[5-chloro-1-[3-fluoro-1-(oxetan-3-yl)-4-piperidyl]pyrazol-4-yl]-N4-methyl-5-(trifluoromethyl)pyrimidine-2,4-diamine;

[4-[[5-chloro-4-(methylamino)pyrimidin-2-yl]amino]-3-methoxy-phenyl]-morpholino-methanone;

1-methyl-4-(4-morpholino-7H-pyrrolo[2,3-d]pyrimidin-5-yl)pyrrole-2-carbonitrile;

2-[2-methoxy-4-[4-(4-methylpiperazin-1-yl)piperidine-1-carbonyl]anilino]-5,11-dimethyl-pyrimido[4,5-b][1,4]benzodiazepin-6-one; and cis-2,6-dimethyl-4-[6-[5-(1-methylcyclopropoxy)-1H-indazol-3-yl]pyrimidin-4-yl]morpholine;

or a pharmaceutically acceptable salt thereof.

In some embodiments, the LRRK2 inhibitor is [4-[[4-(ethylamino)-5-(trifluoromethyl)pyrimidin-2-yl]amino]-2-fluoro-5-methoxy-phenyl]-morpholino-methanone, or a pharmaceutically acceptable salt thereof.

In some embodiments, the LRRK2 inhibitor is N2-[5-chloro-1-[3-fluoro-1-(oxetan-3-yl)-4-piperidyl]pyrazol-4-yl]-N4-methyl-5-(trifluoromethyl)pyrimidine-2,4-diamine, or a pharmaceutically acceptable salt thereof.

In some embodiments, the LRRK2 inhibitor is [4-[[5-chloro-4-(methylamino)pyrimidin-2-yl]amino]-3-methoxy-phenyl]-morpholino-methanone, or a pharmaceutically acceptable salt thereof.

In some embodiments, the LRRK2 inhibitor is 1-methyl-4-(4-morpholino-7H-pyrrolo[2,3-d]pyrimidin-5-yl)pyrrole-2-carbonitrile, or a pharmaceutically acceptable salt thereof.

In some embodiments, the LRRK2 inhibitor is 2-[2-methoxy-4-[4-(4-methylpiperazin-1-yl)piperidine-1-carbonyl]anilino]-5,11-dimethyl-pyrimido[4,5-b][1,4]benzodiazepin-6-one, or a pharmaceutically acceptable salt thereof.

In some embodiments, the LRRK2 inhibitor is cis-2,6-dimethyl-4-[6-[5-(1-methylcyclopropoxy)-1H-indazol-3-yl]pyrimidin-4-yl]morpholine, or a pharmaceutically acceptable salt thereof.

Exemplary PD-1 Axis Binding Antagonists for Use in the Invention

Provided herein are methods for treating or delaying progression of cancer in an individual comprising administering to the individual an effective amount of a LRRK2 inhibitor and a PD-1 axis binding antagonist. For example, a PD-1 axis binding antagonist includes a PD-1 binding antagonist, a PD-L1 binding antagonist and a PD-L2 binding antagonist. Alternative names for "PD-1" include CD279 and SLEB2. Alternative names for "PD-L1" include B7-H1, B7-4, CD274, and B7-H. Alternative names for "PD-L2" include B7-DC, Btdc, and CD273. In some embodiments, PD-1, PD-L1, and PD-L2 are human PD-1, PD-L1 and PD-L2.

In some embodiments, the PD-1 binding antagonist is a molecule that inhibits the binding of PD-1 to its ligand binding partners. In a specific aspect the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, the PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or oligopeptide.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PD-L2-Fc fusion soluble receptor described in WO2010/027827 and WO2011/066342.

In some embodiments, the anti-PD-1 antibody is nivolumab (CAS Registry Number:946414-94-4). In a still further embodiment, provided is an isolated anti-PD-1 antibody comprising a heavy chain variable region comprising the heavy chain variable region amino acid sequence from SEQ ID NO:1 and/or a light chain variable region comprising the light chain variable region amino acid sequence from SEQ ID NO:2. In a still further embodiment, provided is an isolated anti-PD-1 antibody comprising a heavy chain and/or a light chain sequence, wherein:

(a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence:

(SEQ ID NO: 1)
VQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATN

DDYWGQGTLVTVSSASTKGPSVFPLAPCSRSTSESTAALGCLVKDYFPE

PVTVSWNSGALTSGVHTFPAVLQSSGLYSLSSVVTVPSSSLGTKTYTCN

VDHKPSNTKVDKRVESKYGPPCPPCPAPEFLGGPSVFLFPPKPKDTLMI

SRTPEVTCVVVDVSQEDPEVQFNWYVDGVEVHNAKTKPREEQFNSTYRV

VSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK, or (b) the light chain sequences has at least 85%, at least 90%, at least 91%, at least 92%, at least 93%, at least 94%, at least 95%, at least 96%, at least 97%, at least 98%, at least 99% or 100% sequence identity to the light chain sequence:

(SEQ ID NO: 2)
EIVLTQSPATLSLSPGERATLSCRASQSVSSYLAWYQQKPGQAPRLLIY

DASNRATGIPARFSGSGSGTDFTLTISSLEPEDFAVYYCQQSSNWPRTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.

In some embodiments, the anti-PD-1 antibody is pembrolizumab (CAS Registry Number: 1374853-91-4). In a still further embodiment, provided is an isolated anti-PD-1 antibody comprising a heavy chain variable region comprising the heavy chain variable region amino acid sequence from SEQ ID NO:3 and/or a light chain variable region comprising the light chain variable region amino acid sequence from SEQ ID NO:4. In a still further embodiment, provided is an isolated anti-PD-1 antibody comprising a heavy chain and/or a light chain sequence, wherein:

(a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence:

(SEQ ID NO: 3)
QVQLVQSGVE

VKKPGASVKVSCKASGYTFT NYYMYWVRQA PGQGLEWMGG

INPSNGGTNF NEKFKNRVTLTTDSSTTTAY

MELKSLQFDD TAVYYCARRDYRFDMGFDYW

GQGTTVTVSSASTKGPSVFP

LAPCSRSTSE STAALGCLVKDYFPEPVTVS

WNSGALTSGVHTFPAVLQSS

GLYSLSSVVT VPSSSLGTKTYTCNVDHKPS

NTKVDKRVESKYGPPCPPCP

APEFLGGPSV FLFPPKPKDTLMISRTPEVT

-continued

CVVVDVSQEDPEVQFNWYVD

GVEVHNAKTK PREEQFNSTYRVVSVLTVLH

QDWLNGKEYKCKVSNKGLPS

SIEKTISKAK GQPREPQVYTLPPSQEEMTK

NQVSLTCLVKGFYPSDIAVE

WESNGQPENN YKTTPPVLDSDGSFFLYSRL

TVDKSRWQEGNVFSCSVMHE

ALHNHYTQKS LSLSLGK, or (b) the light chain sequences has at least 85%, at least 90%, at least 91%, at least 92%, at least 93%, at least 94%, at least 95%, at least 96%, at least 97%, at least 98%, at least 99% or 100% sequence identity to the light chain sequence:

(SEQ ID NO: 4)
EIVLTQSPATLSLSPGERATLSCRASKGVSTSGYSYLHWYQQKPGQAPR

LLIYLASYLESGVPARFSGSGSGTDFTLTISSLEPEDFAVYYCQHSRDL

PLTFGGGTKVEIKRTVAAPSVFIFPPSDEQLKSGTASVVCLLNNFYPRE

AKVQWKVDNALQSGNSQESVTEQDSKDSTYSLSSTLTLSKADYEKHKVY

ACEVTHQGLSSPVT KSFNRGEC.

In some embodiments, the PD-L1 binding antagonist is anti-PD-L1 antibody. In some embodiments, the anti-PD-L1 binding antagonist is selected from the group consisting of YW243.55.S70, MPDL3280A, MDX-1105, and MEDI4736. MDX-1105, also known as BMS-936559, is an anti-PD-L1 antibody described in WO2007/005874. Antibody YW243.55.S70 is an anti-PD-L1 described in WO 2010/077634 A1. MEDI4736 is an anti-PD-L1 antibody described in WO2011/066389 and US2013/034559, each incorporated herein by reference as if set forth in their entirety.

Examples of anti-PD-L1 antibodies useful for the methods of this invention, and methods for making thereof are described in PCT patent application WO 2010/077634 A1 and U.S. Pat. No. 8,217,149, each incorporated herein by reference as if set forth in their entirety. In some embodiments, the PD-1 axis binding antagonist is an anti-PD-L1 antibody. In some embodiments, the anti-PD-L1 antibody is capable of inhibiting binding between PD-L1 and PD-1 and/or between PD-L1 and B7-1. In some embodiments, the anti-PD-L1 antibody is a monoclonal antibody. In some embodiments, the anti-PD-L1 antibody is an antibody fragment selected from the group consisting of Fab, Fab'-SH, Fv, scFv, and $(Fab')_2$ fragments. In some embodiments, the anti-PD-L1 antibody is a humanized antibody. In some embodiments, the anti-PD-L1 antibody is a human antibody. The anti-PD-L1 antibodies useful in this invention, including compositions containing such antibodies, such as those described in WO 2010/077634 A1, may be used in combination with a LRRK2 inhibitor to treat cancer. In some embodiments, the anti-PD-L1 antibody comprises a heavy chain variable region comprising the amino acid sequence of SEQ ID NO:25 and a light chain variable region comprising the amino acid sequence of SEQ ID NO:26.

In another embodiment, provided is an anti-PD-L1 antibody comprising a heavy chain and a light chain variable region sequence, wherein:

(a) the heavy chain further comprises and HVR-H1, HVR-H2 and an HVRH3 sequence having at least 85% sequence identity to GFTFSDSWIH (SEQ ID NO:10), AWISPYGGSTYYADSVKG (SEQ ID NO:11), and RHWPGGFDY (SEQ ID NO:12), respectively, or (b) the light chain further comprises an HVR-L1, HVR-L2 and an HVR-L3 sequence having at least 85% sequence identity to RASQDVSTAVA (SEQ ID NO:13), SASFLYS (SEQ ID NO:14) and QQYLYHPAT (SEQ ID NO:15), respectively.

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HCFR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
HC-FR1
                                        (SEQ ID NO: 16)
EVQLVESGGGLVQPGGSLRLSCAAS

HC-FR2
                                        (SEQ ID NO: 17)
WVRQAPGKGLEWV

HC-FR3
                                        (SEQ ID NO: 18)
RFTISADTSKNTAYLQMNSLRAEDTAVYYCAR

HC-FR4
                                        (SEQ ID NO: 19)
WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
                                        (SEQ ID NO: 21)
DIQMTQSPSSLSASVGDRVTITC

LC-FR2
                                        (SEQ ID NO: 22)
WYQQKPGKAPKLLIY

LC-FR3
                                        (SEQ ID NO: 23)
GVPSRFSGSGSGTDFTLTISSLQPEDFATYYC

LC-FR4
                                        (SEQ ID NO: 24)
FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect the minimal effector function results from an "effectorless Fc mutation" or aglycosylation. In still a further embodiment, the effector-less Fc mutation is an N297A or D265A/N297A substitution in the constant region.

In a still further embodiment, provided is an isolated anti-PD-L1 antibody comprising a heavy chain and a light chain variable region sequence, wherein:

(a) the heavy chain sequence has at least 85% sequence identity to the heavy chain sequence:

```
                                        (SEQ ID NO: 25)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSA,
```

or (b) the light chain sequence has at least 85% sequence identity to the light chain sequence:

```
                                        (SEQ ID NO: 26)
DIQMTQSPSSLSASVGDRVTITCRASQDVSTAVAWYQQKPGKAPKLLIY

SASFLYSGVPSRFSGSGSGTDFTLTISSLQPEDFATYYCQQYLYHPATF

GQGTKVEIKR
```

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HCFR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
                                        (SEQ ID NO: 16)
HC-FR1 EVQLVESGGGLVQPGGSLRLSCAAS

                                        (SEQ ID NO: 17)
HC-FR2 WVRQAPGKGLEWV

                                        (SEQ ID NO: 18)
HC-FR3 RFTISADTSKNTAYLQMNSLRAEDTAVYYCAR

                                        (SEQ ID NO: 19)
HC-FR4 WGQGTLVTVSA
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
                                         (SEQ ID NO: 21)
LC-FR1 DIQMTQSPSSLSASVGDRVTITC
                                         (SEQ ID NO: 22)
LC-FR2 WYQQKPGKAPKLLIY
                                         (SEQ ID NO: 23)
LC-FR3 GVPSRFSGSGSGTDFTLTISSLQPEDFATYYC
                                         (SEQ ID NO: 24)
LC-FR4 FGQGTKVEIKR
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further embodiment, the effector-less Fc mutation is an N297A or D265A/N297A substitution in the constant region.

In another further embodiment, provided is an isolated anti-PD-L1 antibody comprising a heavy chain and a light chain variable region sequence, wherein:

(a) the heavy chain sequence has at least 85% sequence identity to the heavy chain sequence:

```
                                         (SEQ ID NO: 7)
EVQLVESGGGLVQPGGSLRLSCAASGFTFSDSWIHWVRQAPGKGLEWVA

WISPYGGSTYYADSVKGRFTISADTSKNTAYLQMNSLRAEDTAVYYCAR

RHWPGGFDYWGQGTLVTVSS,
```

or (b) the light chain sequence has at least 85% sequence identity to the light chain sequence:

```
                                         (SEQ ID NO: 26)
DIQMTQSPSSLSASVGDRVTITCRASQDVSTAVAWYQQKPGKAPKLLIY

SASFLYSGVPSRFSGSGSGTDFTLTISSLQPEDFATYYCQQYLYHPATF

GQGTKVEIKR
```

In a still further embodiment, provided is an isolated anti-PD-L1 antibody comprising a heavy chain and a light chain variable region sequence, wherein:

(a) the heavy chain sequence has at least 85% sequence identity to the heavy chain sequence:

```
                                         (SEQ ID NO: 8)
EVQLVESGGGLVQPGGSLRLSCAASGFTFSDSWIHWVRQAPGKGLEWVAW
```

-continued

```
ISPYGGSTYYADSVKGRFTISADTSKNTAYLQMNSLRAEDTAVYYCARRH

WPGGFDYWGQGTLVTVSSASTK,
```

or (b) the light chain sequences has at least 85% sequence identity to the light chain sequence:

```
                                         (SEQ ID NO: 9)
DIQMTQSPSSLSASVGDRVTITCRASQDVSTAVAWYQQKPGKAPKLLIY

SASFLYSGVPSRFSGSGSGTDFTLTISSLQPEDFATYYCQQYLYHPATF

GQGTKVEIKR
```

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HCFR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
                                         (SEQ ID NO: 16)
HC-FR1 EVQLVESGGGLVQPGGSLRLSCAAS
                                         (SEQ ID NO: 17)
HC-FR2 WVRQAPGKGLEWV
                                         (SEQ ID NO: 18)
HC-FR3 RFTISADTSKNTAYLQMNSLRAEDTAVYYCAR
                                         (SEQ ID NO: 19)
HC-FR4 WGQGTLVTVSS
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
                                         (SEQ ID NO: 21)
LC-FR1 DIQMTQSPSSLSASVGDRVTITC
                                         (SEQ ID NO: 22)
LC-FR2 WYQQKPGKAPKLLIY
                                         (SEQ ID NO: 23)
LC-FR3 GVPSRFSGSGSGTDFTLTISSLQPEDFATYYC
                                         (SEQ ID NO: 24)
LC-FR4 FGQGTKVEIKR
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an “effector-less Fc mutation” or aglycosylation. In still a further embodiment, the effector-less Fc mutation is an N297A or D265A/N297A substitution in the constant region.

In yet another embodiment, the anti-PD-L1 antibody is MPDL3280A (CAS Registry Number: 1422185-06-5). In a still further embodiment, provided is an isolated anti-PD-L1 antibody comprising a heavy chain and/or a light chain sequence, wherein:

(a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence:

```
                                     (SEQ ID NO: 5)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYAST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPG,
```

or (b) the light chain sequences has at least 85%, at least 90%, at least 91%, at least 92%, at least 93%, at least 94%, at least 95%, at least 96%, at least 97%, at least 98%, at least 99% or 100% sequence identity to the light chain sequence:

```
                                     (SEQ ID NO: 6)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.
```

In a still further embodiment, the invention provides for compositions comprising any of the above described anti-PD-L1 antibodies in combination with at least one pharmaceutically acceptable carrier.

In a still further embodiment, provided is an isolated nucleic acid encoding a light chain or a heavy chain variable region sequence of an anti-PD-L1 antibody, wherein:

(a) the heavy chain further comprises and HVR-H1, HVR-H2 and an HVRH3 sequence having at least 85% sequence identity to GFTFSDSWIH (SEQ ID NO:10), AWISPYGGSTYYADSVKG (SEQ ID NO:11) and RHWPGGFDY (SEQ ID NO:12), respectively, and (b) the light chain further comprises an HVR-L1, HVR-L2 and an HVR-L3 sequence having at least 85% sequence identity to RASQDVSTAVA (SEQ ID NO:13), SASFLYS (SEQ ID NO:14) and QQYLYHPAT (SEQ ID NO:15), respectively.

In a specific aspect, the sequence identity is 86%, 87%, 88%, 89%, 90%, 91%, 92%, 93%, 94%, 95%, 96%, 97%, 98%, 99% or 100%. In aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LCFR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
                                     (SEQ ID NO: 16)
HC-FR1 EVQLVESGGGLVQPGGSLRLSCAAS

                                     (SEQ ID NO: 17)
HC-FR2 WVRQAPGKGLEWV

                                     (SEQ ID NO: 18)
HC-FR3 RFTISADTSKNTAYLQMNSLRAEDTAVYYCAR

                                     (SEQ ID NO: 19)
HC-FR4 WGQGTLVTVSA
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
                                     (SEQ ID NO: 21)
LC-FR1 DIQMTQSPSSLSASVGDRVTITC

                                     (SEQ ID NO: 22)
LC-FR2 WYQQKPGKAPKLLIY

                                     (SEQ ID NO: 23)
LC-FR3 GVPSRFSGSGSGTDFTLTISSLQPEDFATYYC

                                     (SEQ ID NO: 24)
LC-FR4 FGQGTKVEIKR
```

In a still further specific aspect, the antibody described herein (such as an anti-PD-1 antibody, an anti-PD-L1 antibody, or an anti-PD-L2 antibody) further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an “effector-less Fc mutation” or aglycosylation. In still a further aspect, the effector-less Fc mutation is an N297A or D265A/N297A substitution in the constant region.

In a still further aspect, provided herein are nucleic acids encoding any of the antibodies described herein. In some embodiments, the nucleic acid further comprises a vector suitable for expression of the nucleic acid encoding any of the previously described anti-PD-L1, anti-PD-1, or anti-PD-L2 antibodies. In a still further specific aspect, the vector further comprises a host cell suitable for expression of the nucleic acid. In a still further specific aspect, the host cell is a eukaryotic cell or a prokaryotic cell. In a still further specific aspect, the eukaryotic cell is a mammalian cell, such as Chinese Hamster Ovary (CHO).

The antibody or antigen binding fragment thereof, may be made using methods known in the art, for example, by a process comprising culturing a host cell containing nucleic acid encoding any of the previously described anti-PD-L1, anti-PD-1, or anti-PD-L2 antibodies or antigen-binding fragment in a form suitable for expression, under conditions suitable to produce such antibody or fragment, and recovering the antibody or fragment.

In some embodiments, the isolated anti-PD-L1 antibody is aglycosylated.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Removal of glycosylation sites form an antibody is conveniently accomplished by altering the amino acid sequence such that one of the above-described tripeptide sequences (for N-linked glycosylation sites) is removed. The alteration may be made by substitution of an asparagine, serine or threonine residue within the glycosylation site another amino acid residue (e.g., glycine, alanine or a conservative substitution).

In any of the embodiments herein, the isolated anti-PD-L1 antibody can bind to a human PD-L1, for example a human PD-L1 as shown in UniProtKB/Swiss-Prot Accession No.Q9NZQ7.1, or a variant thereof.

In a still further embodiment, the invention provides for a composition comprising an anti-PD-L1, an anti-PD-1, or an anti-PD-L2 antibody or antigen binding fragment thereof as provided herein and at least one pharmaceutically acceptable carrier. In some embodiments, the anti-PD-L1, anti-PD-1, or anti-PD-L2 antibody or antigen binding fragment thereof administered to the individual is a composition comprising one or more pharmaceutically acceptable carrier.

Any of the pharmaceutically acceptable carriers described herein or known in the art may be used.

In some embodiments, the anti-PD-L1 antibody described herein is in a formulation comprising the antibody at an amount of about 60 mg/mL, histidine acetate in a concentration of about 20 mM, sucrose in a concentration of about 120 mM, and polysorbate (e.g., polysorbate 20) in a concentration of 0.04% (w/v), and the formulation has a pH of about 5.8. In some embodiments, the anti-PD-L1 antibody described herein is in a formulation comprising the antibody in an amount of about 125 mg/mL, histidine acetate in a concentration of about 20 mM, sucrose is in a concentration of about 240 mM, and polysorbate (e.g., polysorbate 20) in a concentration of 0.02% (w/v), and the formulation has a pH of about 5.5.

Antibody Preparation

As described above, in some embodiments, the PD-1 binding antagonist is an antibody (e.g., an anti-PD-1 antibody, an anti-PD-L1 antibody, or an anti-PD-L2 antibody). The antibodies described herein may be prepared using techniques available in the art for generating antibodies, exemplary methods of which are described in more detail in the following sections.

The antibody is directed against an antigen of interest. For example, the antibody may be directed against PD-1 (such as human PD-1), PD-L1 (such as human PD-L1), PD-L2 (such as human PD-L2). Preferably, the antigen is a biologically important polypeptide and administration of the antibody to a mammal suffering from a disorder can result in a therapeutic benefit in that mammal.

In certain embodiments, an antibody described herein has a dissociation constant (Kd) of 1 μM, 150 nM, 100 nM, 50 nM, 10 nM, 1 nM, 0.1 nM, 0.01 nM, or 0.001 nM (e.g. 10-8 M or less, e.g. from 10-8 M to 10-13 M, e.g., from 10-9 M to 10-13 M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of (125I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [125I]-antigen are mixed with serial dilutions of a Fab of interest. The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20 ™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, NJ) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates (kon) and dissociation rates (koff) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio koff/kon. See, e.g., Chen et al., *J. Mol. Biol.* 293:865-881 (1999). If the on-rate exceeds 106 M-1 s-1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

Antibody Fragments

In certain embodiments, an antibody described herein is an antibody fragment. Antibody fragments include, but are not limited to, Fab, Fab', Fab'-SH, $F(ab')_2$, Fv, and scFv fragments, and other fragments described below. For a review of certain antibody fragments, see Hudson et al. *Nat. Med.* 9:129-134 (2003). For a review of scFv fragments, see, e.g., Pluckthtin, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

Chimeric and Humanized Antibodies

In certain embodiments, an antibody described herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof. In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osboum et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

Human Antibodies

In certain embodiments, an antibody described herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications*, pp. 51-63 (Marcel Dekker, Inc., New York, 1987); and Boemer et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing humanhuman hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Library-Derived Antibodies

Antibodies may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N J, 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, NJ, 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide highaffinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360. Antibodies or antibody fragments isolated from human antibody libraries are considered human antibodies or human antibody fragments herein.

Multispecific Antibodies

In certain embodiments, an antibody described herein is a multispecific antibody, e.g. a bispecific antibody. Multispecific antibodies are monoclonal antibodies that have binding specificities for at least two different sites. In some embodiments, the PD-1 axis component antagonist is multispecific. In one of the binding specificities is for a PD-1 axis component (e.g., PD-1, PD-L1, or PD-L2) and the other is for any other antigen. In some embodiments, one of the binding specificities is for IL-17 or IL-17R and the other is for any other antigen. In certain embodiments, bispecific antibodies may bind to two different epitopes of a PD-1 axis component (e.g., PD-1, PD-L1, or PD-L2), IL-17, or IL-17R. Bispecific antibodies can be prepared as full length antibodies or antibody fragments.

In some embodiments, one of the binding specificities is for a PD-1 axis component (e.g., PD-1, PD-L1, or PD-L2) and the other is for IL-17 or IL-17R. Provided herein are methods for treating or delaying progression of cancer in an individual comprising administering to the individual an effective amount of a multispecific antibody, wherein the multispecific antibody comprises a first binding specificity for a PD-1 axis component (e.g., PD-1, PD-L1, or PD-L2) and a second binding specificity for IL-17 or IL-17R. In some embodiments, a multispecific antibody may be made by any of the techniques described herein and below. Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); crosslinking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF"

comprising an antigen binding site that binds to a PD-1 axis component (e.g., PD-1, PD-L1, or PD-L2), IL-17, or IL-17R as well as another, different antigen (see, US 2008/0069820, for example).

Nucleic Acid Sequences, Vectors and Methods of Production

Polynucleotides encoding a PD1 axis binding antagonist, e.g., antibodies, may be used for production of the PD1 axis binding antagonists described herein. The PD1 axis binding antagonists used according to the invention may be expressed as a single polynucleotide that encodes the entire bispecific antigen binding molecule or as multiple (e.g., two or more) polynucleotides that are co-expressed. Polypeptides encoded by polynucleotides that are co-expressed may associate through, e.g., disulfide bonds or other means to form a functional PD1 axis binding antagonist antibody. For example, the light chain portion of a Fab fragment may be encoded by a separate polynucleotide from the portion of the bispecific antibody comprising the heavy chain portion of the Fab fragment, an Fc domain subunit and optionally (part of) another Fab fragment. When co-expressed, the heavy chain polypeptides will associate with the light chain polypeptides to form the Fab fragment. In another example, the portion of the PD-1 axis binding antagonist antigen binding portion provided therein comprising one of the two Fc domain subunits and optionally (part of) one or more Fab fragments could be encoded by a separate polynucleotide from the portion of the bispecific antibody provided therein comprising the other of the two Fc domain subunits and optionally (part of) a Fab fragment. When co-expressed, the Fc domain subunits will associate to form the Fc domain.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

Antibody Variants

In certain embodiments, amino acid sequence variants of the PD-1 axis binding antagonist antibodies are contemplated, in addition to those described above. For example, it may be desirable to improve the binding affinity and/or other biological properties of the antibodies. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

Substitution, Insertion, and Deletion Variants

In certain embodiments, variants having one or more amino acid substitutions are provided. Sites of interest for substitutional mutagenesis include the HVRs and FRs. Conservative substitutions are shown in Table B under the heading of "conservative substitutions." More substantial changes are provided in Table B under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE B

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |

TABLE B-continued

| Original Residue | Exemplary Substitutions | Preferred Substitutions |
|---|---|---|
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody used with the invention comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in a bispecific antibody or an antibody binding to DR5 of the invention may be made in order to create antibody variants with certain improved properties.

In one embodiment, bispecific antibody variants or variants of antibodies are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. Arch. Biochem. Biophys. 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

Cysteine Engineered Antibody Variants

In certain embodiments, it may be desirable to create cysteine engineered antibodies, e.g., THIOMABS, in which one or more residues of the antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

Recombinant Methods and Compositions

Antibodies of the invention may be obtained, for example, by solid-state peptide synthesis (e.g. Merrifield solid phase synthesis) or recombinant production. For recombinant production one or more polynucleotide encoding the antibodies (or fragments), e.g., as described above, is isolated and inserted into one or more vectors for further cloning and/or expression in a host cell. Such polynucleotide may be readily isolated and sequenced using conventional procedures. In one embodiment a vector, preferably an expression vector, comprising one or more of the polynucleotides of the invention is provided. Methods which are well known to those skilled in the art can be used to construct expression vectors containing the coding sequence of an antibody along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y (1989). The expression vector can be part of a plasmid, virus, or may be a nucleic acid fragment. The expression vector includes an expression cassette into which the polynucleotide encoding an antibody (fragment) (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the antibody, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells.

Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit â-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the antibody is desired, DNA encoding a signal sequence may be placed upstream of the nucleic acid encoding an antibody of the invention or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse (3-glucuronidase.

DNA encoding a short protein sequence that could be used to facilitate later purification (e.g. a histidine tag) or assist in labeling the antibody may be included within or at the ends of the antibody (fragment) encoding polynucleotide.

In a further embodiment, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one such embodiment a host cell comprises (e.g. has been transformed or transfected with) a vector comprising a polynucleotide that encodes an antibody of the invention or a part thereof. As used herein, the term "host cell" refers to any kind of cellular system which can be engineered to generate the antibody, e.g., anti-PD-1 antibodies, anti-PD-L1 antibodies, and anti-PD-L2 antibodies of the invention or fragments thereof. Host cells suitable for replicating and for supporting expression of antibodies of the invention are well known in the art. Such cells may be transfected or transduced as appropriate with the particular expression vector and large quantities of vector containing cells can be grown for seeding large scale fermenters to obtain sufficient quantities of the antibodies for clinical applications. Suitable host cells include prokaryotic micro-organisms, such as *E. coli*, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B.K.C. Lo, ed., Humana Press, Totowa, NJ), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NS0, Sp20 cell).

Standard technologies are known in the art to express foreign genes in these systems. Cells expressing a polypeptide comprising either the heavy or the light chain of an antigen binding domain such as an antibody, may be engineered so as to also express the other of the antibody chains such that the expressed product is an antibody that has both a heavy and a light chain.

Any animal species of antibody, antibody fragment, antigen binding domain or variable region can be used in the antibodies used according to the invention. Non-limiting antibodies, antibody fragments, antigen binding domains or variable regions useful in the present invention can be of murine, primate, or human origin. If the antibody is intended for human use, a chimeric form of antibody may be used wherein the constant regions of the antibody are from a human. A humanized or fully human form of the antibody can also be prepared in accordance with methods well known in the art (see e. g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, N J, 2001); and McCafferty et al., Nature 348, 552-554; Clackson et al., Nature 352, 624-628 (1991)).

Phage typically display antibody fragments, either as single-chain Fv (scFv) fragments or as Fab fragments.

In certain embodiments, the antigen binding moieties useful in the present invention are engineered to have enhanced binding affinity according to, for example, the methods disclosed in U.S. Pat. Appl. Publ. No. 2004/0132066, the entire contents of which are hereby incorporated by reference. The ability of the antibody of the invention to bind to a specific antigenic determinant can be measured either through an enzyme-linked immunosorbent assay (ELISA) or other techniques familiar to one of skill in the art, e.g. surface plasmon resonance technique (analyzed on a BIACORE T100 system) (Liljeblad, et al., Glyco J 17, 323-329 (2000)), and traditional binding assays (Heeley, Endocr Res 28, 217-229 (2002)). Competition assays may be used to identify an antibody, antibody fragment, antigen binding domain or variable domain that competes with a reference antibody for binding to a particular antigen. In certain embodiments, such a competing antibody binds to the same epitope (e.g. a linear or a conformational epitope) that is bound by the reference antibody. Detailed exemplary methods for mapping an epitope to which an antibody binds are provided in Morris (1996) "Epitope Mapping Protocols," in Methods in Molecular Biology vol. 66 (Humana Press, Totowa, NJ). In an exemplary competition assay, immobilized antigen (e.g. PD-1) is incubated in a solution comprising a first labeled antibody that binds to the antigen (e.g. V9 antibody, described in U.S. Pat. No. 6,054,297) and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to the antigen. See Harlow and Lane (1988) Antibodies: A Laboratory Manual ch.14 (Cold Spring Harbor Laboratory, Cold Spring Harbor, NY).

In certain embodiments, the antigen binding moieties useful in the present invention are engineered to have enhanced binding affinity according to, for example, the methods disclosed in U.S. Pat. Appl. Publ. No. 2004/0132066, the entire contents of which are hereby incorporated by reference. The ability of the antibody of the invention to bind to a specific antigenic determinant can be measured either through an enzyme-linked immunosorbent assay (ELISA) or other techniques familiar to one of skill in the art, e.g. surface plasmon resonance technique (analyzed on a BIACORE T100 system) (Liljeblad, et al., Glyco J 17, 323-329 (2000)), and traditional binding assays (Heeley, Endocr Res 28, 217-229 (2002)). Competition assays may be used to identify an antibody, antibody fragment, antigen binding domain or variable domain that competes with a reference antibody for binding to a particular antigen. In certain embodiments, such a competing antibody binds to the same epitope (e.g. a linear or a conformational epitope) that is bound by the reference antibody. Detailed exemplary methods for mapping an epitope to which an antibody binds are provided in Morris (1996) "Epitope Mapping Protocols," in Methods in Molecular Biology vol. 66 (Humana Press, Totowa, NJ). In an exemplary competition assay, immobilized antigen is incubated in a solution comprising a first labeled antibody that binds to the antigen and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody.

After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to the antigen. See Harlow and Lane (1988) Antibodies: A Laboratory Manual ch.14 (Cold Spring Harbor Laboratory, Cold Spring Harbor, NY).

Antibodies prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the bispecific antibody or the antibody binding to DR5 binds. For example, for affinity chromatography purification of bispecific antibodies of the invention, a matrix with protein A or protein G may be used. Sequential Protein A or G affinity chromatography and size exclusion chromatography can be used to isolate a bispecific antibody essentially as described in the Examples. The purity of the bispecific antibody or the antibody binding to DR5 can be determined by any of a variety of well-known analytical methods including gel electrophoresis, high pressure liquid chromatography, and the like.

Assays

Antibodies, e.g., anti-PD-1 axis binding antagonist antibodies provided herein may be identified, screened for, or characterized for their physical/chemical properties and/or biological activities by various assays known in the art.

Affinity Assays

The affinity of the antibodies, e.g., anti-PD-1 axis binding antagonist antibodies provided herein for their respective antigen, e.g., PD-1, PD-L1, can be determined in accordance with the methods set forth in the Examples by surface plasmon resonance (SPR), using standard instrumentation such as a BIAcore instrument (GE Healthcare), and receptors or target proteins such as may be obtained by recombinant expression. Alternatively, binding of antibodies provided therein to their respective antigen may be evaluated using cell lines expressing the particular receptor or target antigen, for example by flow cytometry (FACS).

$K_D$ may be measured by surface plasmon resonance using a BIACORE® T100 machine (GE Healthcare) at 25° C. To analyze the interaction between the Fc-portion and Fc receptors, His-tagged recombinant Fc-receptor is captured by an anti-Penta His antibody (Qiagen) ("Penta His") immobilized on CM5 chips and the bispecific constructs are used as analytes. Briefly, carboxymethylated dextran biosensor chips (CM5, GE Healthcare) are activated with N-ethyl-N'-(3-dimethylaminopropyl)-carbodiimide hydrochloride (EDC) and N-hydroxysuccinimide (NHS) according to the supplier's instructions. Anti Penta-His antibody ("Penta His") is diluted with 10 mM sodium acetate, pH 5.0, to 40

μg/ml before injection at a flow rate of 5 μl/min to achieve approximately 6500 response units (RU) of coupled protein. Following the injection of the ligand, 1 M ethanolamine is injected to block unreacted groups. Subsequently the Fc-receptor is captured for 60 s at 4 or 10 nM. For kinetic measurements, four-fold serial dilutions of the bispecific construct (range between 500 nM and 4000 nM) are injected in HBS-EP (GE Healthcare, 10 mM HEPES, 150 mM NaCl, 3 mM EDTA, 0.05% Surfactant P20, pH 7.4) at 25° C. at a flow rate of 30 μl/min for 120 s.

To determine the affinity to the target antigen, bispecific constructs are captured by an anti human Fab specific antibody (GE Healthcare) that is immobilized on an activated CMS-sensor chip surface as described for the anti Penta-His antibody ("Penta His"). The final amount of coupled protein is approximately 12000 RU. The bispecific constructs are captured for 90 s at 300 nM. The target antigens are passed through the flow cells for 180 s at a concentration range from 250 to 1000 nM with a flowrate of 30 μl/min. The dissociation is monitored for 180 s.

Bulk refractive index differences are corrected for by subtracting the response obtained on reference flow cell. The steady state response was used to derive the dissociation constant $K_D$ by non-linear curve fitting of the Langmuir binding isotherm. Association rates ($k_{on}$) and dissociation rates ($k_{off}$) are calculated using a simple one-to-one Langmuir binding model (BIACORE® T100 Evaluation Software version 1.1.1) by simultaneously fitting the association and dissociation sensorgrams. The equilibrium dissociation constant ($K_D$) is calculated as the ratio $k_{off}/k_{on}$. See, e.g., Chen et al., J Mol Biol 293, 865-881 (1999).

Binding Assays and Other Assays

In one aspect, an antibodies, e.g., anti-PD-1 axis binding antagonist antibodies of the invention is tested for its antigen binding activity, e.g., by known methods such as ELISA, Western blot, etc.

In another aspect, competition assays may be used to identify an antibody or fragment that competes with a specific reference antibody for binding to the respective antigens. In certain embodiments, such a competing antibody binds to the same epitope (e.g., a linear or a conformational epitope) that is bound by a specific reference antibody. Detailed exemplary methods for mapping an epitope to which an antibody binds are provided in Morris (1996) "Epitope Mapping Protocols," in *Methods in Molecular Biology* vol. 66 (Humana Press, Totowa, NJ). Further methods are described in the example section.

Activity Assays

In one aspect, assays are provided for identifying antibodies, e.g., anti-PD-1 axis binding antagonist antibodies provided herein having biological activity. Biological activity may include, e.g., inducing DNA fragmentation, induction of apoptosis and lysis of targeted cells. Antibodies having such biological activity in vivo and/or in vitro are also provided.

In certain embodiments, an antibody of the invention is tested for such biological activity. Assays for detecting cell lysis (e.g. by measurement of LDH release) or apoptosis (e.g. using the TUNEL assay) are well known in the art. Assays for measuring ADCC or CDC are also described in WO 2004/065540 (see Example 1 therein), the entire content of which is incorporated herein by reference.

Pharmaceutical Formulations

Pharmaceutical formulations of antibodies, e.g., anti-PD-1 axis binding antagonist antibodies as described herein are prepared by mixing such antibody having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

A typical formulation of a LRRK2 inhibitor is prepared by mixing a LRRK2 inhibitor and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005.

The formulation of a LRRK2 inhibitor may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Another embodiment of the invention provides a pharmaceutical composition or medicament containing a LRRK2 inhibitor and a therapeutically inert carrier, diluent or excipient, as well as a method of using the LRRK2 inhibitors to prepare such composition and medicament. In one example, the LRRK2 inhibitor may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a LRRK2 inhibitor is formulated in an acetate buffer, at pH 5. In another embodiment, the LRRK2 inhibitor is sterile. The LRRK2 inhibitor may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

Exemplary LRRK Inhibitor Formulation A

Film coated tablets containing the following ingredients can be manufactured in a conventional manner:

| Ingredients | Per tablet | |
|---|---|---|
| Kernel: | | |
| LRRK2 inhibitor | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Exemplary LRRK Inhibitor Formulation B

Capsules containing the following ingredients can be manufactured in a conventional manner:

| Ingredients | Per capsule |
|---|---|
| LRRK2 inhibitor | 25.0 mg |
| Lactose | 150.0 mg |
| Maize starch | 20.0 mg |
| Talc | 5.0 mg |

The components are sieved and mixed and filled into capsules of size 2.

Exemplary LRRK Inhibitor Formulation C

Injection solutions can have the following composition:

| | |
|---|---|
| LRRK2 inhibitor | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

Exemplary LRRK Inhibitor Formulation D

Sachets of the following composition can be manufactured in a conventional manner:

| | |
|---|---|
| LRRK2 inhibitor | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidon K 30 | 10.0 mg |
| Magnesium stearate | 10.0 mg |
| Flavoring additives | 1.0 mg |

Therapeutic Methods and Compositions

The therapeutic combinations comprising one or more of the anti-PD-1 axis binding antagonist antibody and the LRRK2 inhibitor provided herein may be used in therapeutic methods.

In one aspect, an anti-PD-1 axis binding antagonist antibody for use as a medicament is provided for use in combination with a LRRK2 inhibitor. In certain embodiments, an anti-PD-1 axis binding antagonist antibody for use in combination with a LRRK2 inhibitor is provided for use in a method of treatment. In certain embodiments, the invention provides an anti-PD-1 axis binding antagonist antibody and a LRRK2 inhibitor for use in a method of treating an individual having cancer comprising administering to the individual an effective amount of the anti-PD-1 axis binding antagonist antibody and the LRRK2 inhibitor. An "individual" according to any of the above embodiments is preferably a human. In one preferred embodiment, said cancer is pancreatic cancer, sarcoma or colorectal carcinoma. In other embodiments, the cancer is colorectal cancer, sarcoma, head and neck cancers, squamous cell carcinomas, breast cancer, pancreatic cancer, gastric cancer, non-small-cell lung carcinoma, small-cell lung cancer or mesothelioma. In embodiments in which the cancer is breast cancer, the breast cancer may be triple negative breast cancer.

In a further aspect, the invention provides the use of a therapeutic combination comprising an anti-PD-1 axis binding antagonist antibody and a LRRK2 inhibitor in the manufacture or preparation of a medicament. In one embodiment, the medicament is for treatment of cancer. In a further embodiment, the medicament is for use in a method of treating cancer comprising administering to an individual having cancer an effective amount of the medicament. In one such embodiment, the method further comprises administering to the individual an effective amount of at least one additional therapeutic agent, e.g., as described below. An "individual" according to any of the above embodiments may be a human.

In a further aspect, the invention provides a method for treating cancer. In one embodiment, the method comprises administering to an individual having cancer an effective amount of a therapeutic combination comprising an anti-PD-1 axis binding antagonist antibody and a LRRK2 inhibitor. In one such embodiment, the method further comprises administering to the individual an effective amount of at least one additional therapeutic agent, as described below. An "individual" according to any of the above embodiments may be a human. In one preferred embodiment said cancer is pancreatic cancer, sarcoma or colorectal carcinoma. In other embodiments, the cancer is colorectal cancer, sarcoma, head and neck cancers, squamous cell carcinomas, breast cancer, pancreatic cancer, gastric cancer, non-small-cell lung carcinoma, small-cell lung cancer or mesothelioma.

In a further aspect, the invention provides pharmaceutical formulations comprising any one of the anti-PD-1 axis binding antagonist antibody provided herein, e.g., for use in any of the above therapeutic methods, and a LRRK2 inhibitor. In one embodiment, a pharmaceutical formulation comprises any of the anti-PD-1 axis binding antagonist provided herein and a pharmaceutically acceptable carrier. In another embodiment, a pharmaceutical formulation comprises any of the anti-PD-1 axis binding antagonist antibody and LRRK2 inhibitors provided herein and at least one additional therapeutic agent, e.g., as described below.

An antibody can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

A LRRK2 inhibitor can be administered by any suitable means, including orally, topical (including buccal and sublingual), rectal, vaginal, transdermal, subcutaneous, intraperitoneal, intradermal, intrathecal, epidural, parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

A LRRK2 inhibitor may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

Antibodies and LRRK2 inhibitors may be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of such other agents depends on the amount of antibody and/or LRRK2 inhibitor present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a antibody and/or LRRK2 inhibitor will depend on the type of disease to be treated, the type of antibody and/or the type of LRRK inhibitor, the severity and course of the disease, whether the antibody and/or LRRK2 inhibitor is administered for preventive or therapeutic purposes, previous therapy, the patient's clinical history and response to the antibody and/or LRRK2 inhibitor and the discretion of the attending physician. The antibody is suitably administered to the patient at one time or over a series of treatments. Depending on the type and severity of the disease, about 1 μg/kg to 15 mg/kg (e.g. 0.1 mg/kg-10 mg/kg) of the antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the bispecific would be in the range from about 0.05 mg/kg to about 10 mg/kg. Thus, one or more doses of about 0.5 mg/kg, 2.0 mg/kg, 4.0 mg/kg or 10 mg/kg may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

In general, a LRRK2 inhibitor will be administered in a therapeutically effective amount by any of the accepted modes of administration for agents that serve similar utilities. Suitable dosage ranges are typically 1-500 mg daily, for example 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease. A particular manner of administration is generally oral using a convenient daily dosage regimen which can be adjusted according to the degree of affliction.

A LRRK2 inhibitor, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of LRRK2 inhibitor or, more broadly, about 0.01 to about one hundred (100) milligrams, per tablet, are accordingly suitable representative unit dosage forms.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a bispecific antibody and an additional active agent is the further chemotherapeutic agent as described herein. The label or package insert indicates that the composition is used for treating the condition of choice. Moreover, the article of manufacture may comprise (a) a first container with a composition contained therein, wherein the composition comprises a bispecific antibody; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Specific Numbered Embodiments:

1. A PD-1 axis binding antagonist for use in a method for treating or delaying progression of cancer, wherein the PD-1 axis binding antagonist is used in combination with a LRRK2 inhibitor.

2. The PD-1 axis binding antagonist for use in a method of embodiment 1, wherein the PD-1 axis binding antagonist is selected from the group consisting of a PD-1 binding antagonist, a PD-L1 binding antagonist and a PD-L2 binding antagonist.

3. The PD-1 axis binding antagonist for use in a method of embodiment 1 or 2, wherein the PD-1 axis binding antagonist inhibits the binding of PD-1 to its ligand binding partners.

4. The PD-1 axis binding antagonist for use in a method of any one of embodiments 1-3, wherein the PD-1 axis binding antagonist inhibits the binding of PD-1 to PD-L1.

5. The PD-1 axis binding antagonist for use in a method of any one of embodiments 1-4, wherein the PD-1 axis binding antagonist inhibits the binding of PD-1 to PD-L2.

6. The PD-1 axis binding antagonist for use in a method of any one of embodiments 1-5, wherein the PD-1 axis binding antagonist inhibits the binding of PD-1 to both PD-L1 and PD-L2.

7. The PD-1 axis binding antagonist for use in a method of any one of embodiments 1-6, wherein the PD-1 binding antagonist is an antibody.

8. The PD-1 axis binding antagonist for use in a method of embodiments 1-7, wherein the PD-1 axis binding antagonist is an antibody fragment selected from the group consisting of Fab, Fab'-SH, Fv, scFv, and $(Fab')_2$ fragments.

9. The PD-1 axis binding antagonist for use in a method of any one of embodiments 1-8, wherein the PD-1 axis binding antagonist is a monoclonal antibody.

10. The PD-1 axis binding antagonist for use in a method of any one of embodiments 1-9, wherein the PD-1 axis binding antagonist is a humanized antibody or a human antibody.

11. The PD-1 axis antagonist for use in a method of any one of embodiments 1-10, wherein the PD-1 axis binding agonist is an antibody comprising a heavy chain comprising HVR-H1 sequence of SEQ ID NO:10, HVR-H2 sequence of SEQ ID NO:11, and HVR-H3 sequence of SEQ ID NO:12; and a light chain comprising HVR-L1 sequence of SEQ ID NO:13, HVR-L2 sequence of SEQ ID NO:14, and HVR-L3 sequence of SEQ ID NO:15.

12. The PD-1 axis binding antagonist for use in a method of any one of embodiments 1-11, wherein the PD-1 axis binding agonist is an antibody comprising a heavy chain variable region comprising the amino acid sequence of SEQ ID NO:7 or SEQ ID NO:8 and a light chain variable region comprising the amino acid sequence of SEQ ID NO:9.

13. The PD-1 axis binding antagonist for use in a method of any one of embodiments 1-12, wherein the PD-1 axis binding antagonist is an antibody comprising a heavy chain comprising the amino acid sequence of SEQ ID NO:5 and a light chain comprising the amino acid sequence of SEQ ID NO:6.

14. The PD-1 axis binding antagonist for use in a method of any one of embodiments 1-10, wherein the PD-1 axis binding antagonist is selected from the group consisting of nivolumab, pembrolizumab, and pidilizumab.

15. The PD-1 axis binding antagonist for use in a method of embodiments 1-10 wherein the PD-1 axis binding antagonist is AMP-224.

16. The PD-1 axis binding antagonist for use in a method of any one of embodiments 1-10, wherein the PD-1 axis binding agonist is selected from the group consisting of YVV243.55.570, atezolizumab, MDX-1105, and durvalumab.

17. The PD-1 axis binding antagonist for use in a method of any one of embodiments 1-16, wherein the LRRK2 inhibitor has a molecular weight of 200-900 dalton.

18. The PD-1 axis binding antagonist for use in a method of any one of embodiments 1-17, wherein the LRRK2 inhibitor has a molecular weight of 400-700 dalton.

19. The PD-1 axis binding antagonist for use in a method of any one of embodiments 1-18, wherein the LRRK2 inhibitor comprises an aromatic cycle, which is attached to a heterocycle via a nitrogen atom, wherein the nitrogen atom can form part of the heterocycle.

20. The PD-1 axis binding antagonist for use in a method of any one of embodiment 19, wherein the heterocycle comprises at least two heteroatoms.

21. The PD-1 axis binding antagonist for use in a method of any one of embodiments 1-20, wherein the LRRK2 inhibitor has an IC50 value below 1 μM, below 500 nM, below 200 nM, below 100 nM, below 50 nM, below 25 nM, below 10 nM, below 5 nM, 2 nM or below 1 nM.

22. The PD-1 axis binding antagonist for use in a method of any one of embodiments 1-21, wherein the LRRK2 inhibitor is a compound of formula (I)

(I)

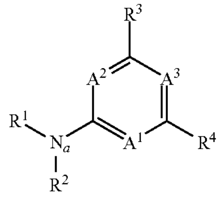

wherein, $A^1$ is —N— or —$CR^5$—;

$A^2$ is —N— or —$CR^6$—;

$A^3$ is —N— or —$CR^7$—;

$N_a$ is —N—;

$R^1$ is alkylamino(haloalkylpyrimidinyl), cyanoalkyl(alkylpyrazolyl), alkylamino(halopyrimidinyl), oxetanyl (halopiperidinyl)halopyrazolyl, halo(N-alkyl-3H-pyrrolo[2,3-d]pyrimidine-amine), 5,11-dialkylpyrimido[4,5-b][1,4]benzodiazepin-6-one, phenyl optionally substituted with one, two or three substituents independently selected from $R_a$, pyrazolyl optionally substituted with one, two or three substituents independently selected from $R_a$, or a condensed bicyclic system optionally substituted with one, two or three substituents independently selected from $R_a$;

$R_a$ is (heterocyclyl)carbonyl, (heterocyclyl)alkyl, heterocyclyl, alkoxy, aminocarbonyl, alkylaminocarbonyl, amino(alkylamino)carbonyl, oxetanylaminocarbonyl, (tetrahydropyranyl)aminocarbonyl, (dialkylamino)carbonyl, (cycloalkylamino)carbonyl, hydroxy, haloalkoxy, cycloalkoxy, (hydroxyalkyl)aminocarbonyl, (alkoxyalkyl)aminocarbonyl, (alkylpiperidinyl) aminocarbonyl, (alkoxyalkyl)alkylaminocarbonyl, (hydroxyalkyl)(alkylamino)carbonyl, (cyanocycloalkyl) aminocarbonyl, (cycloaklyl)alkylaminocarbonyl, (haloazetidinyl)aminocarbonyl, (haloalkyl)aminocarbonyl, morpholinylcarbonylalkyl, morpholinylalkyl, alkyl, fluorine, chlorine, bromine, iodine, (perdeuteromorpholinyl)carbonyl, (halocycloalkyl)aminocarbonyl, oxetanyloxy, (cycloalkyl)alkoxy, cycloalkyl, cyano, alkenyl, alkynyl, alkoxyalkyl, hydroxyalkyl, (cycloalkyl)alkyl, alkylsulfonyl, phenyl, haloalkyl, cyanophenyl, cycloalkylsulfonyl, cyanoalkyl, alkylsulfonylphenyl, (dialkylamino)carbonylphenyl, halophenyl, (alkyloxetanyl)alkyl, (dialkylamino)phenyl, (cycloalkylsulfonyl)phenyl, alkoxycycloalkyl, (alkylamino)carbonylalkyl, pyridazinylalkyl, pyrimidinylalkyl, (alkylpyrazolyl)alkyl, triazolylalkyl, (alkyltriazolyl)alkyl, hydroxycycloalkyl, (oxadiazolyl) alkyl, (dialkylamino)carbonylalkyl, pyrrolidinylcarbonylalkyl, cyanocycloalkyl, alkoxycarbonylalkyl, (haloalkyl)aminocarbonylalkyl, (cycloalkyl) alkylaminocarbonylalkyl, (alkylamino) carbonylcycloalkyl, alkylpiperidinyl(alkylamino) carbonyl, alkylpyrazolyl(alkylamino)carbonyl, (hydroxycycloalkyl)alkylaminocarbonyl, (hydroxycycloalkyl)alkyl, (dialkylimidazolyl)alkyl, (alkyloxazolyl)alkyl, alkoxyalkylsulfonyl, hydroxycarbonyl, morpholinylsulfonyl or alkyl(oxadiazolyl)alkyl, $R^2$ is alkyl or hydrogen;

or $R^1$ and $R^2$ together with $N_a$ form a morpholino optionally substituted with one, two or three alkyl;

$R^3$ and $R^4$ are independently selected from alkoxy, cycloalkylamino, (cycloalkyl)alkylamino, (tetrahydrofuranyl)alkylamino, alkoxyalkylamino, (tetrahydropyranyl)amino, (tetrahydropyranyl)oxy, (tetrahydropyranyl)alkylamino, haloalkylamino, piperidinyl, pyrrolidinyl, (oxetanyl)oxy, haloalkoxy, hydrogen, halogen, alkylamino, morpholinyl and alkyl(cycloalkyloxy)indazolyl;

or $R^3$ is hydrogen, and $R^4$ together with $R^5$ form a pyrrolyl substituted with $R^8$, wherein the pyrrolyl is fused to the aromatic cycle comprising $A^1$, $A^2$ and $A^3$;

$R^5$ and $R^6$ are independently selected from hydrogen and alkyloxy;

$R^7$ is hydrogen, halogen, alkyl, cycloalkyl, alkenyl, alkynyl, cyano, haloalkoxy, (cycloalkyl)alkyl, haloalkyl, (alkylpiperazinyl)piperidinylcarbonyl or morpholinocarbonyl; and $R^8$ is pyrrolyl substituted with cyano(alkylpyrrolyl) or cyanophenyl;

or a pharmaceutically acceptable salt thereof.

23. The PD-1 axis binding antagonist for use in a method of any one of embodiments 1-22, wherein the LRRK2 inhibitor is a compound of formula (I)

(I)

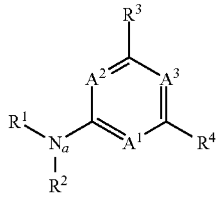

wherein, $A^1$ is —N— or —$CR^5$—;

$A^2$ is —N— or —$CR^6$—;

$A^3$ is —N— or —$CR^7$—;

$N_a$ is —N—;

$R^1$ is alkylamino(haloalkylpyrimidinyl), cyanoalkyl(alkylpyrazolyl), alkylamino(halopyrimidinyl), oxetanyl (halopiperidinyl)halopyrazolyl, halo(N-alkyl-3H-pyrrolo[2,3-d]pyrimidine-amine) or 5,11-dialkylpyrimido [4,5-b][1,4]benzodiazepin-6-one;

$R^2$ is hydrogen;

or $R^1$ and $R^2$ together with $N_a$ form a morpholino optionally substituted with one, two or three alkyl;

$R^3$ and $R^4$ are independently selected from hydrogen, halogen, alkylamino, morpholinyl and alkyl(cycloalkyloxy)indazolyl;

or $R^3$ is hydrogen, and $R^4$ together with $R^5$ form a pyrrolyl substituted with $R^8$, wherein the pyrrolyl is fused to the aromatic cycle comprising $A^1$, $A^2$ and $A^3$;

$R^5$ and $R^6$ are independently selected from hydrogen and alkyloxy;

$R^7$ is haloalkyl, (alkylpiperazinyl)piperidinylcarbonyl or morpholinocarbonyl; and $R^8$ is pyrrolyl substituted with cyano(alkylpyrrolyl) or cyanophenyl;

or a pharmaceutically acceptable salt thereof.

24. The PD-1 axis binding antagonist for use in a method of any one of embodiments 1-23, wherein the LRRK2 inhibitor is a compound of formula (I a)

($I_a$)

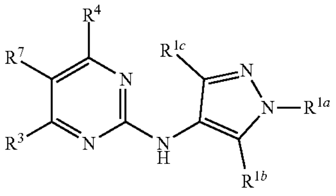

wherein $R^{1a}$ is cyanoalkyl or oxetanyl(halopiperidinyl).

$R^{1b}$ and $R^{1c}$ are independently selected from hydrogen, alkyl and halogen;

$R^3$ and $R^4$ are independently selected from hydrogen and alkylamino; and $R^7$ is haloalkyl;

or a pharmaceutically acceptable salt thereof.

25. The PD-1 axis binding antagonist for use in a method of any one of embodiments 1-23, wherein the LRRK2 inhibitor is a compound of formula ($I_b$)

($I_b$)

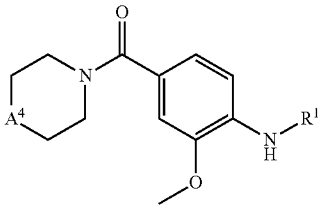

wherein $R^1$ is alkylamino(halopyrimidinyl), halo(N-alkyl-3H-pyrrolo[2,3-d]pyrimidine-amine) or 5,11-dialkylpyrimido[4,5-b][1,4]benzodiazepin-6-one;

$R^3$ is halogen;

$A^4$ is —O— or —$CR^9$—; and $R^9$ is alkylpiperazinyl;

or a pharmaceutically acceptable salt thereof.

26. The PD-1 axis binding antagonist for use in a method of any one of embodiments 1-23, wherein the LRRK2 inhibitor is a compound of formula (I c)

($I_c$)

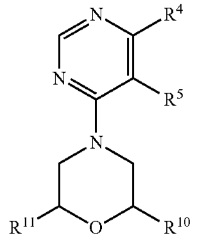

wherein, $R^4$ is alkyl(cycloalkyloxy)indazolyl, and $R^5$ is hydrogen;

or $R^4$ together with $R^5$ forms a pyrrolyl substituted with $R^8$, wherein the pyrrolyl is fused to the pyrimidine of the compound of formula (I c);

$R^8$ is pyrrolyl substituted with cyano(alkylpyrrolyl) or cyanophenyl; and $R^{10}$ and $R^{11}$ are independently selected from hydrogen and alkyl;

or a pharmaceutically acceptable salt thereof.

27. The PD-1 axis binding antagonist for use in a method of any one of embodiments 1-23, wherein the LRRK2 inhibitor is selected from

[4-[[4-(ethylamino)-5-(trifluoromethyl)pyrimidin-2-yl]amino]-2-fluoro-5-methoxy-phenyl]-morpholino-methanone;

2-methyl-2-[3-methyl-4-[[4-(methylamino)-5-(trifluoromethyl)pyrimidin-2-yl]amino]pyrazol-1-yl]propanenitrile;

N2-[5-chloro-1-[3-fluoro-1-(oxetan-3-yl)-4-piperidyl]pyrazol-4-yl]-N4-methyl-5-(trifluoromethyl)pyrimidine-2,4-diamine;

[4-[[5-chloro-4-(methylamino)pyrimidin-2-yl]amino]-3-methoxy-phenyl]-morpholino-methanone;

[4-[[5-chloro-4-(methylamino)-3H-pyrrolo[2,3-d]pyrimidin-2-yl]amino]-3-methoxy-phenyl]-morpholino-methanone;

2-[2-methoxy-4-[4-(4-methylpiperazin-1-yl)piperidine-1-carbonyl]anilino]-5,11-dimethyl-pyrimido[4,5-b][1,4]benzodiazepin-6-one;

3-(4-morpholino-7H-pyrrolo[2,3-d]pyrimidin-5-yl)benzonitrile;

cis-2,6-dimethyl-4-[6-[5-(1-methylcyclopropoxy)-1H-indazol-3-yl]pyrimidin-4-yl]morpholine;

1-methyl-4-(4-morpholino-7H-pyrrolo[2,3-d]pyrimidin-5-yl)pyrrole-2-carbonitrile;

or a pharmaceutically acceptable salt thereof.

28. The PD-1 axis binding antagonist for use in a method of any one of embodiments 1-23, wherein the LRRK2 inhibitor is [4-[[4-(ethylamino)-5-(trifluoromethyl)pyrimidin-2-yl]amino]-2-fluoro-5-methoxy-phenyl]-morpholino-methanone, or a pharmaceutically acceptable salt thereof.

29. The PD-1 axis binding antagonist for use in a method of any one of embodiments 1-23, wherein the LRRK2 inhibitor is N2-[5-chloro-1-[3-fluoro-1-(oxetan-3-yl)-4-piperidyl]pyrazol-4-yl]-N4-methyl-5-(trifluoromethyl)pyrimidine-2,4-diamine, or a pharmaceutically acceptable salt thereof.

30. The PD-1 axis binding antagonist for use in a method of any one of embodiments 1-23, wherein the LRRK2 inhibitor is [4-[[5-chloro-4-(methylamino)pyrimidin-2-yl]amino]-3-methoxy-phenyl]-morpholino-methanone, or a pharmaceutically acceptable salt thereof.

31. The PD-1 axis binding antagonist for use in a method of any one of embodiments 1-23, wherein the LRRK2 inhibitor is 1-methyl-4-(4-morpholino-7H-pyrrolo[2,3-d]pyrimidin-5-yl)pyrrole-2-carbonitrile, or a pharmaceutically acceptable salt thereof.

32. The PD-1 axis binding antagonist for use in a method of any one of embodiments 1-31, wherein the treatment results in a sustained response in the individual after cessation of the treatment.

33. The PD-1 axis binding antagonist for use in a method of embodiments 1-32, wherein at least one of the LRRK2 inhibitor and the PD-1 axis binding antagonist is administered continuously.

34. The PD-1 axis binding antagonist for use in a method of embodiments 1-32, wherein at least one of the LRRK2 inhibitor and the PD-1 axis binding antagonist is administered intermittently.

35. The PD-1 axis binding antagonist for use in a method of embodiments 1-34, wherein the PD-1 axis binding antagonist is administered before the LRRK2 inhibitor.

36. The PD-1 axis binding antagonist for use in a method of embodiments 1-35, wherein the PD-1 axis binding antagonist is administered simultaneous with the LRRK2 inhibitor.

37. The PD-1 axis binding antagonist for use in a method of embodiments 1-36, wherein the PD-1 axis binding antagonist is administered after the LRRK2 inhibitor.

38. The PD-1 axis binding antagonist for use in a method of any one of embodiments 1-37, wherein the cancer is selected from the group consisting of ovarian cancer, lung cancer, breast cancer, renal cancer, colorectal cancer, endometrial cancer.

39. The PD-1 axis binding antagonist for use in a method of embodiments 1-38, wherein at least one of the LRRK2 inhibitor and the PD-1 axis binding antagonist is administered intravenously, intramuscularly, subcutaneously, topically, orally, transdermally, intraperitoneally, intraorbitally, by implantation, by inhalation, intrathecally, intraventricularly, or intranasally.

40. The PD-1 axis binding antagonist for use in a method of any one of embodiments 1-39, wherein the LRRK2 inhibitor is administered orally.

41. The PD-1 axis binding antagonist for use in a method of any one of embodiments 1-40, wherein T cells in the individual have enhanced activation, proliferation and/or effector function relative to prior to the administration of the combination.

42. The PD-1 axis binding antagonist for use in a method of any one of embodiments 1-41 wherein T cells in the individual have enhanced activation, proliferation and/or effector function relative to administration of the PD-1 axis binding antagonist alone.

43. The PD-1 axis binding antagonist for use in a method of embodiment 40 or 41, wherein T cell effector function is secretion of at least one of IL-2, IFN-$\gamma$ and TNF-$\alpha$.

44. A kit comprising a LRRK2 inhibitor and a package insert comprising instructions for using the LRRK2 inhibitor with a PD-1 axis binding antagonist to treat or delay progression of cancer in an individual.

45. A kit comprising a LRRK2 inhibitor and a PD-1 axis binding antagonist, and a package insert comprising instructions for using the LRRK2 inhibitor and the PD-1 axis binding antagonist to treat or delay progression of cancer in an individual.

46. The kit of embodiment 44 or 45, wherein the PD-1 axis binding antagonist is an anti-PD-1 antibody or an anti-PD-L1 antibody.

47. The kit of any one of embodiments 44-46, wherein the PD-1 axis binding antagonist is an anti-PD-1 immunoadhesin.

48. A pharmaceutical product comprising (A) a first composition comprising as active ingredient a PD-1 axis binding antagonist antibody and a pharmaceutically acceptable carrier; and (B) a second composition comprising as active ingredient a LRRK2 inhibitor and a pharmaceutically acceptable carrier, for use in the combined, sequential or simultaneous, treatment of a disease, in particular cancer.

49. A pharmaceutical composition comprising a LRRK2 inhibitor, a PD-1 axis binding antagonist and a pharmaceutically acceptable carrier.

50. The pharmaceutical product of embodiment 46 or the pharmaceutical composition of embodiment 49 for use in treating or delaying progression of cancer, in particular for treating or delaying of ovarian cancer, lung cancer, breast cancer, renal cancer, colorectal cancer, endometrial cancer.

51. Use of a combination of a LRRK2 inhibitor and a PD-1 axis binding antagonist in the manufacture of a medicament for treating or delaying progression of a proliferative disease, in particular cancer.

52. The use of embodiment 49, wherein the medicament is for treatment of ovarian cancer, lung cancer, breast cancer, renal cancer, colorectal cancer, endometrial cancer.

53. A method for treating or delaying progression of a cancer in an individual comprising administering to the individual an effective amount of a LRRK2 inhibitor and a PD-1 axis binding antagonist.

54. The method of embodiment 53, wherein the PD-1 axis binding antagonist is selected from the group consisting of a PD-1 binding antagonist, a PD-L1 binding antagonist and a PD-L2 binding antagonist.

55. The method of embodiment 53 or 54, wherein the PD-1 axis binding antagonist inhibits the binding of PD-1 to its ligand binding partners.

56. The method of any one of embodiments 53-55, wherein the PD-1 axis binding antagonist inhibits the binding of PD-1 to PD-L1.

57. The method of any one of embodiments 53-56, wherein the PD-1 axis binding antagonist inhibits the binding of PD-1 to PD-L2.

58. The method of any one of embodiments 53-57, wherein the PD-1 axis binding antagonist inhibits the binding of PD-1 to both PD-L1 and PD-L2.

59. The method of any one of embodiments 53-58, wherein the PD-1 axis binding antagonist is an antibody.

60. The method of any one of embodiments 53-59, wherein the PD-1 axis binding antagonist is an antibody fragment selected from the group consisting of Fab, Fab'-SH, Fv, scFv, and (Fab')2 fragments.

61. The method of any one of embodiments 53-60, wherein the PD-1 axis binding antagonist is a monoclonal antibody.

62. The method of any one of embodiments 53-61, wherein the PD-1 axis binding antagonist is a humanized antibody or a human antibody.

63. The method of any one of embodiments 53-62, wherein the PD-1 axis binding agonist is an antibody comprising a heavy chain comprising HVR-H1 sequence of SEQ ID NO:10, HVR-H2 sequence of SEQ ID NO:11, and HVR-H3 sequence of SEQ ID NO:12; and a light chain comprising HVR-L1 sequence of SEQ ID NO:13, HVR-L2 sequence of SEQ ID NO:14, and HVR-L3 sequence of SEQ ID NO: 15.

64. The method of any one of embodiments 53-63, wherein the PD-1 axis binding agonist is an antibody comprising a heavy chain variable region comprising the amino acid sequence of SEQ ID NO:7 or SEQ ID NO:8 and a light chain variable region comprising the amino acid sequence of SEQ ID NO:9.

65. A method for treating or delaying progression of a cancer in an individual comprising administering to the individual an effective amount of a LRRK2 inhibitor and a PD-1 axis binding antagonist wherein the PD-1 axis binding antagonist is an antibody comprising a heavy chain comprising the amino acid sequence of SEQ ID NO:5 and a light chain comprising the amino acid sequence of SEQ ID NO:6.

66. The method of any one of embodiments 53-62, wherein the PD-1 axis binding antagonist is selected from the group consisting of nivolumab, pembrolizumab, and pidilizumab.

67. The method of any one of embodiments 53-62 wherein the PD-1 axis binding antagonist is AMP-224.

68. The method of any one of embodiments 53-62, wherein the PD-1 axis binding agonist is selected from the group consisting of YVV243.55.S70, atezolizumab, MDX-1105, and durvalumab.

69. The PD-1 axis binding antagonist for use in a method of any one of embodiments 53-68, wherein the LRRK2 inhibitor has a molecular weight of 200-900 dalton.

70. The PD-1 axis binding antagonist for use in a method of any one of embodiments 53-69, wherein the LRRK2 inhibitor has a molecular weight of 400-700 dalton.

71. The PD-1 axis binding antagonist for use in a method of any one of embodiments 53-70, wherein the LRRK2 inhibitor comprises an aromatic cycle, which is attached to a heterocycle via a nitrogen atom, wherein the nitrogen atom can form part of the heterocycle.

72. The PD-1 axis binding antagonist for use in a method of any one of embodiment 71, wherein the heterocycle comprises at least two heteroatoms.

73. The PD-1 axis binding antagonist for use in a method of any one of embodiments 53-72, wherein the LRRK2 inhibitor has an IC50 value below 1 μM, below 500 nM, below 200 nM, below 100 nM, below 50 nM, below 25 nM, below 10 nM, below 5 nM, 2 nM or below 1 nM.

74. The method of any one of embodiments 53-73, wherein the LRRK2 inhibitor is a compound of formula (I), wherein the LRRK2 inhibitor is a compound of formula (I)

(I)

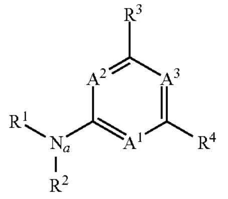

wherein, $A^1$ is —N— or —$CR^5$—;

$A^2$ is —N— or —$CR^6$—;

$A^3$ is —N— or —$CR^7$—;

$N_a$ is —N—;

$R^1$ is alkylamino(haloalkylpyrimidinyl), cyanoalkyl(alkylpyrazolyl), alkylamino(halopyrimidinyl), oxetanyl (halopiperidinyl)halopyrazolyl, halo(N-alkyl-3H-pyrrolo[2,3-d]pyrimidine-amine), 5,11-dialkylpyrimido[4,5-b][1,4]benzodiazepin-6-one, phenyl optionally substituted with one, two or three substituents independently selected from $R_a$, pyrazolyl optionally substituted with one, two or three substituents independently selected from $R_a$, or a condensed bicyclic system optionally substituted with one, two or three substituents independently selected from $R_a$;

$R_a$ is (heterocyclyl)carbonyl, (heterocyclyl)alkyl, heterocyclyl, alkoxy, aminocarbonyl, alkylaminocarbonyl, amino(alkylamino)carbonyl, oxetanylaminocarbonyl, (tetrahydropyranyl)aminocarbonyl, (dialkylamino)carbonyl, (cycloalkylamino)carbonyl, hydroxy, haloalkoxy, cycloalkoxy, (hydroxyalkyl)aminocarbonyl, (alkoxyalkyl)aminocarbonyl, (alkylpiperidinyl) aminocarbonyl, (alkoxyalkyl)alkylaminocarbonyl, (hydroxyalkyl)(alkylamino)carbonyl, (cyanocycloalkyl) aminocarbonyl, (cycloaklyl)alkylaminocarbonyl, (haloazetidinyl)aminocarbonyl, (haloalkyl)aminocarbonyl, morpholinylcarbonylalkyl, morpholinylalkyl, alkyl, fluorine, chlorine, bromine, iodine, (perdeuteromorpholinyl)carbonyl, (halocycloalkyl)aminocarbonyl, oxetanyloxy, (cycloalkyl)alkoxy, cycloalkyl, cyano, alkenyl, alkynyl, alkoxyalkyl, hydroxyalkyl, (cycloalkyl)alkyl, alkylsulfonyl, phenyl, haloalkyl, cyanophenyl, cycloalkylsulfonyl, cyanoalkyl, alkylsulfonylphenyl, (dialkylamino)carbonylphenyl, halophenyl, (alkyloxetanyl)alkyl, (dialkylamino)phenyl, (cycloalkylsulfonyl)phenyl, alkoxycycloalkyl, (alkylamino)carbonylalkyl, pyridazinylalkyl, pyrimidinylalkyl, (alkylpyrazolyl)alkyl, triazolylalkyl, (alkyltriazolyl)alkyl, hydroxycycloalkyl, (oxadiazolyl) alkyl, (dialkylamino)carbonylalkyl, pyrrolidinylcarbonylalkyl, cyanocycloalkyl, alkoxycarbonylalkyl, (haloalkyl)aminocarbonylalkyl, (cycloalkyl) alkylaminocarbonylalkyl, (alkylamino) carbonylcycloalkyl, alkylpiperidinyl(alkylamino) carbonyl, alkylpyrazolyl(alkylamino)carbonyl, (hydroxycycloalkyl)alkylaminocarbonyl, (hydroxycycloalkyl)alkyl, (dialkylimidazolyl)alkyl, (alkyloxazolyl)alkyl, alkoxyalkylsulfonyl, hydroxycarbonyl, morpholinylsulfonyl or alkyl(oxadiazolyl)alkyl, $R^2$ is alkyl or hydrogen;

or $R^1$ and $R^2$ together with $N_a$ form a morpholino optionally substituted with one, two or three alkyl;

$R^3$ and $R^4$ are independently selected from alkoxy, cycloalkylamino, (cycloalkyl)alkylamino, (tetrahydrofuranyl)alkylamino, alkoxyalkylamino, (tetrahydropyranyl)amino, (tetrahydropyranyl)oxy, (tetrahydropyranyl)alkylamino, haloalkylamino, piperidinyl, pyrrolidinyl, (oxetanyl)oxy, haloalkoxy, hydrogen, halogen, alkylamino, morpholinyl and alkyl(cycloalkyloxy)indazolyl;

or $R^3$ is hydrogen, and $R^4$ together with $R^5$ form a pyrrolyl substituted with $R^8$, wherein the pyrrolyl is fused to the aromatic cycle comprising $A^1$, $A^2$ and $A^3$;

$R^5$ and $R^6$ are independently selected from hydrogen and alkyloxy;

$R^7$ is hydrogen, halogen, alkyl, cycloalkyl, alkenyl, alkynyl, cyano, haloalkoxy, (cycloalkyl)alkyl, haloalkyl, (alkylpiperazinyl)piperidinylcarbonyl or morpholinocarbonyl; and $R^8$ is pyrrolyl substituted with cyano(alkylpyrrolyl) or cyanophenyl;

or a pharmaceutically acceptable salt thereof.

75. The method of any one of embodiments 53-74, wherein the LRRK2 inhibitor is a compound of formula (I)

(I)

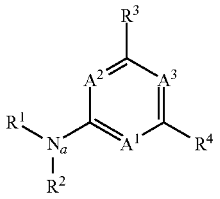

wherein, $A^1$ is —N— or —$CR^5$—;

$A^2$ is —N— or —$CR^6$—;

$A^3$ is —N— or —$CR^7$—;

$N_a$ is —N—;

$R^1$ is alkylamino(haloalkylpyrimidinyl), cyanoalkyl(alkylpyrazolyl), alkylamino(halopyrimidinyl), oxetanyl(halopiperidinyl)halopyrazolyl, halo(N-alkyl-3H-pyrrolo[2,3-d]pyrimidine-amine) or 5,11-dialkylpyrimido[4,5-b][1,4]benzodiazepin-6-one;

$R^2$ is hydrogen;

or $R^1$ and $R^2$ together with $N_a$ form a morpholino optionally substituted with one, two or three alkyl;

$R^3$ and $R^4$ are independently selected from hydrogen, halogen, alkylamino, morpholinyl and alkyl(cycloalkyloxy)indazolyl;

or $R^3$ is hydrogen, and $R^4$ together with $R^5$ form a pyrrolyl substituted with $R^8$, wherein the pyrrolyl is fused to the aromatic cycle comprising $A^1$, $A^2$ and $A^3$;

$R^5$ and $R^6$ are independently selected from hydrogen and alkyloxy;

$R^7$ is haloalkyl, (alkylpiperazinyl)piperidinylcarbonyl or morpholinocarbonyl; and $R^8$ is pyrrolyl substituted with cyano(alkylpyrrolyl) or cyanophenyl;

or a pharmaceutically acceptable salt thereof.

76. The method of any one of embodiments 53-75, wherein the LRRK2 inhibitor is a compound of formula ($I_a$)

($I_a$)

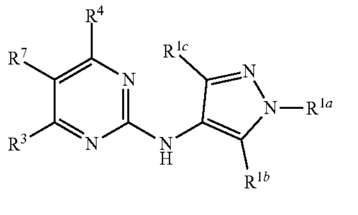

wherein $R^{1a}$ is cyanoalkyl or oxetanyl(halopiperidinyl).

$R^{1b}$ and $R^{1c}$ are independently selected from hydrogen, alkyl and halogen;

$R^3$ and $R^4$ are independently selected from hydrogen and alkylamino; and $R^7$ is haloalkyl;

or a pharmaceutically acceptable salt thereof.

77. The method of any one of embodiments 53-75, wherein the LRRK2 inhibitor is a compound of formula ($I_b$)

($I_b$)

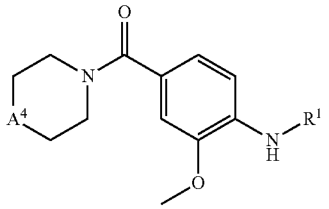

wherein $R^1$ is alkylamino(halopyrimidinyl), halo(N-alkyl-3H-pyrrolo[2,3-d]pyrimidine-amine) or 5,11-dialkylpyrimido[4,5-b][1,4]benzodiazepin-6-one;

$R^3$ is halogen;

$A^4$ is —O— or —$CR^9$—; and $R^9$ is alkylpiperazinyl;

or a pharmaceutically acceptable salt thereof.

78. The method of any one of embodiments 53-75, wherein the LRRK2 inhibitor is a compound of formula (I c)

($I_c$)

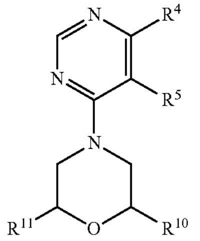

wherein, $R^4$ is alkyl(cycloalkyloxy)indazolyl, and $R^5$ is hydrogen;

or $R^4$ together with $R^5$ forms a pyrrolyl substituted with $R^8$, wherein the pyrrolyl is fused to the pyrimidine of the compound of formula ($I_c$);

$R^8$ is pyrrolyl substituted with cyano(alkylpyrrolyl) or cyanophenyl; and $R^{10}$ and $R^{11}$ are independently selected from hydrogen and alkyl;

or a pharmaceutically acceptable salt thereof.

79. The method of any one of embodiments 53-75, wherein the LRRK2 inhibitor is selected from

[4-[[4-(ethylamino)-5-(trifluoromethyl)pyrimidin-2-yl]amino]-2-fluoro-5-methoxy-phenyl]-morpholino-methanone;

2-methyl-2-[3-methyl-4-[[4-(methylamino)-5-(trifluoromethyl)pyrimidin-2-yl]amino]pyrazol-1-yl]propanenitrile;

N2-[5-chloro-1-[3-fluoro-1-(oxetan-3-yl)-4-piperidyl]pyrazol-4-yl]-N4-methyl-5-(trifluoromethyl)pyrimidine-2,4-diamine;

[4-[[5-chloro-4-(methylamino)pyrimidin-2-yl]amino]-3-methoxy-phenyl]-morpholino-methanone;

[4-[[5-chloro-4-(methylamino)-3H-pyrrolo[2,3-d]pyrimidin-2-yl]amino]-3-methoxy-phenyl]-morpholino-methanone;

2-[2-methoxy-4-[4-(4-methylpiperazin-1-yl)piperidine-1-carbonyl]anilino]-5,11-dimethyl-pyrimido[4,5-b][1,4]benzodiazepin-6-one;

3-(4-morpholino-7H-pyrrolo[2,3-d]pyrimidin-5-yl)benzonitrile; rac-(2R,6S)-2,6-dimethyl-4-[6-[5-(1-methylcyclopropoxy)-1H-indazol-3-yl]pyrimidin-4-yl]morpholine;

1-methyl-4-(4-morpholino-7H-pyrrolo[2,3-d]pyrimidin-5-yl)pyrrole-2-carbonitrile; or a pharmaceutically acceptable salt thereof.

80. The method of any one of embodiments 53-75, wherein the LRRK2 inhibitor is [4-[[4-(ethylamino)-5-(trifluoromethyl)pyrimidin-2-yl]amino]-2-fluoro-5-methoxy-phenyl]-morpholino-methanone, or a pharmaceutically acceptable salt thereof.

81. The method of any one of embodiments 53-75, wherein the LRRK2 inhibitor is N2-[5-chloro-1-[3-fluoro-1-(oxetan-3-yl)-4-piperidyl]pyrazol-4-yl]-N4-methyl-5-(trifluoromethyl)pyrimidine-2,4-diamine, or a pharmaceutically acceptable salt thereof.

82. The method of any one of embodiments 53-75, wherein the LRRK2 inhibitor is [4-[[5-chloro-4-(methylamino)pyrimidin-2-yl]amino]-3-methoxy-phenyl]-morpholino-methanone, or a pharmaceutically acceptable salt thereof.

83. The method of any one of embodiments 53-75, wherein the LRRK2 inhibitor is 1-methyl-4-(4-morpholino-7H-pyrrolo[2,3-d]pyrimidin-5-yl)pyrrole-2-carbonitrile, or a pharmaceutically acceptable salt thereof.

84. The method of any one of embodiments 53-83, wherein the treatment results in a sustained response in the individual after cessation of the treatment.

85. The method of any of embodiments 53-84, wherein at least one of the LRRK2 inhibitor and the PD-1 axis binding antagonist is administered continuously.

86. The method of any of embodiments 53-84, wherein at least one of the LRRK2 inhibitor and the PD-1 axis binding antagonist is administered intermittently.

87. The method of any of embodiments 53-86, wherein the PD-1 axis binding antagonist is administered before the LRRK2 inhibitor.

88. The method of any of embodiments 53-87, wherein the PD-1 axis binding antagonist is administered simultaneous with the LRRK2 inhibitor.

89. The method of any of embodiments 53-88, wherein the PD-1 axis binding antagonist is administered after the LRRK2 inhibitor.

90. The method of any one of embodiments 53-89, wherein the cancer is selected from the group consisting of ovarian cancer, lung cancer, breast cancer, renal cancer, colorectal cancer, endometrial cancer.

91. The method of any one of embodiments 53-90, wherein at least one of the LRRK2 inhibitor and the PD-1 axis binding antagonist is administered intravenously, intramuscularly, subcutaneously, topically, orally, transdermally, intraperitoneally, intraorbitally, by implantation, by inhalation, intrathecally, intraventricularly, or intranasally.

92. The method of any one of embodiments 53-91, wherein the LRRK2 inhibitor is administered orally.

93. The method of any one of embodiments 53-92, wherein T cells in the individual have enhanced activation, proliferation and/or effector function relative to prior to the administration of the combination.

94. The method of any one of embodiments 53-93 wherein T cells in the individual have enhanced activation, proliferation and/or effector function relative to administration of the PD-1 axis binding antagonist alone.

95. The method of embodiment 93 or 94, wherein T cell effector function is secretion of at least one of IL-2, IFN-γ and TNF-α. An invention as described herein.

96. The invention as hereinbefore described.

III. Examples

The following are examples of methods and compositions of the invention. It is understood that various other embodiments may be practiced, given the general description provided above.

The following are examples of methods and compositions of the invention. It is understood that various other embodiments may be practiced, given the general description provided above.

General Methods

Recombinant DNA Techniques

Standard methods were used to manipulate DNA as described in Sambrook et al., Molecular cloning: A laboratory manual; Cold Spring Harbor Laboratory Press, Cold Spring Harbor, New York, 1989. The molecular biological reagents were used according to the manufacturers' instructions. General information regarding the nucleotide sequences of human immunoglobulins light and heavy chains is given in: Kabat, E. A. et al., (1991) Sequences of Proteins of Immunological Interest, $5^{th}$ ed., NIH Publication No. 91-3242.

DNA Sequencing

DNA sequences were determined by double strand sequencing.

Gene Synthesis

Desired gene segments where required were either generated by PCR using appropriate templates or were synthesized by Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells.

Example 1

CRISPR/Cas9 Screening in Mouse Dendritic Cells Line

The first goal was the generation of a new sorting based CRISPR/Cas9 screening to identify novel enhancer of antigen cross-presentation in dendritic cells that can boost T cell priming and T cell mediated anticancer immunity. We first established a protocol to induce maturation and activation of the dendritic cell-like cell line DC2.4 that renders cells capable of internalizing, processing and presenting a model antigen (OVA long peptide (241-270)) on the cell surface, bound to the MHC-I. In parallel, we set up a protocol for viral transduction of DC2.4 ensuring accurate representation of complex, pooled sgRNA libraries. Conventional CRISPR/Cas9 screens rely on the specific selection (depletion or enrichment) of cells carrying individual sgRNAs in a cell population. Our platform combines the CRISPR/Cas9 screening approach with a sorting based readout allowing the selection and sorting of cells that show an increased antigen cross-presentation phenotype (FIG. 1). Indeed, by taking advantage of an anti-mouse H-2Kb/SIINFEKL antibody, we were capable to label and sort the virally transduced dendritic cells in high and low antigen cross-presenting cells by quantifying SIINFEKL peptide in the context of H-2Kb on the cell membrane. sgRNAs sequencing of the high presenting cells revealed LRRK2 as a regulator of antigen cross presentation in this model.

Example 2

Targeting LRRK2: Genetic Validation in a Mouse Dendritic Cell Line

Figure 2A:
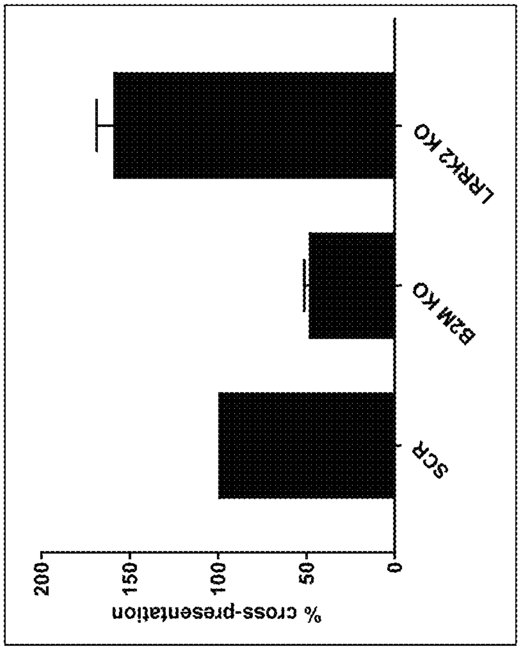
FIG. 2A, FIG. 2B: Effect of LRRK2 knockout in DC2.4 on antigen cross-presentation and T cell priming. DC2.4, virally transduced with Cas9 and sgRNAs targeting LRRK2, B2M (as negative control) or non-targeting (SCR) are used. A) FACSFIG. 2A: FACS based measurement of DC2.4 antigen cross-presentation upon activation, maturation and pulsing with OVA long peptide (241-270) and labelling with anti-mouse H-2Kb/SIINFEKL antibody. B)
Figure 2B:
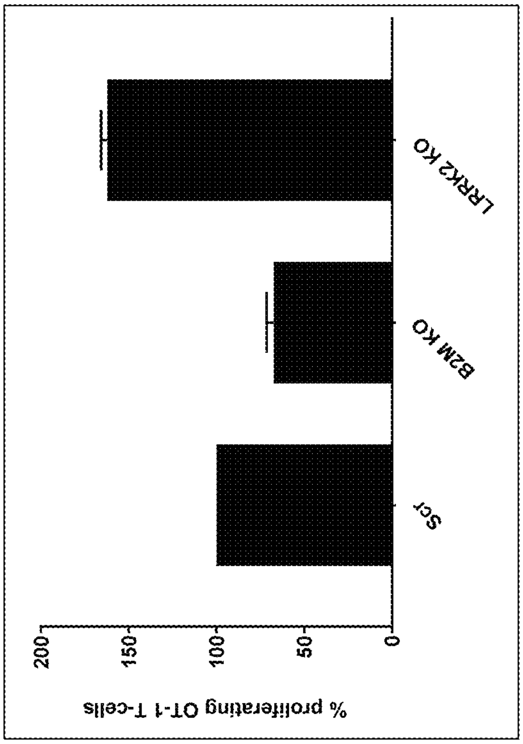
Figure 3A:
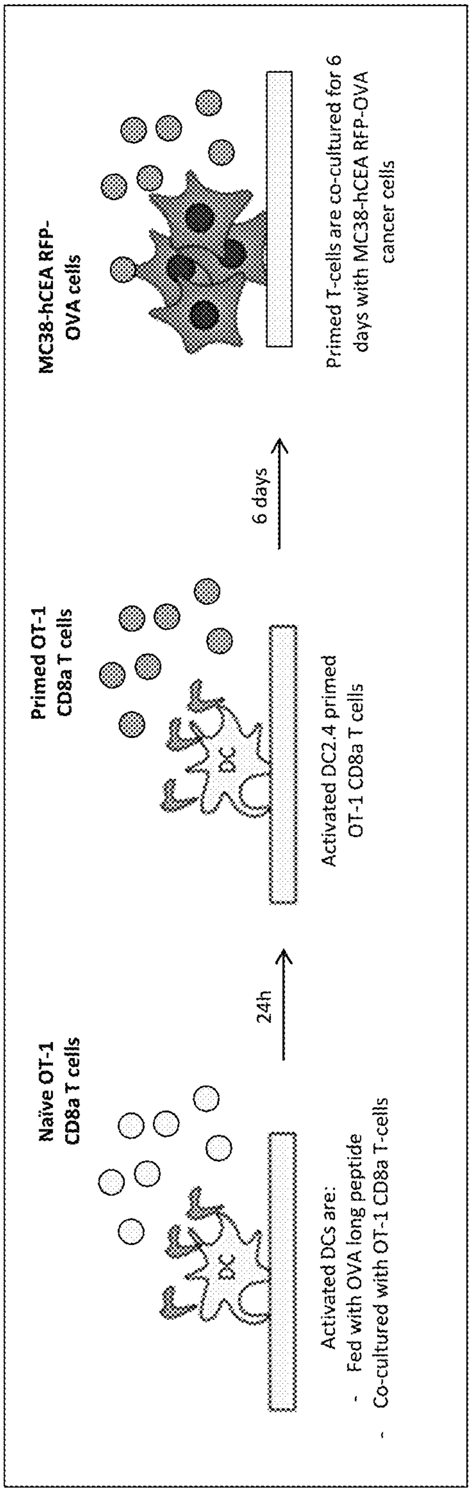
FIG. 3A, FIG. 3B: Effect of LRRK2 knockout in DC2.4 on T cell mediated cancer cell killing.
Figure 3B:
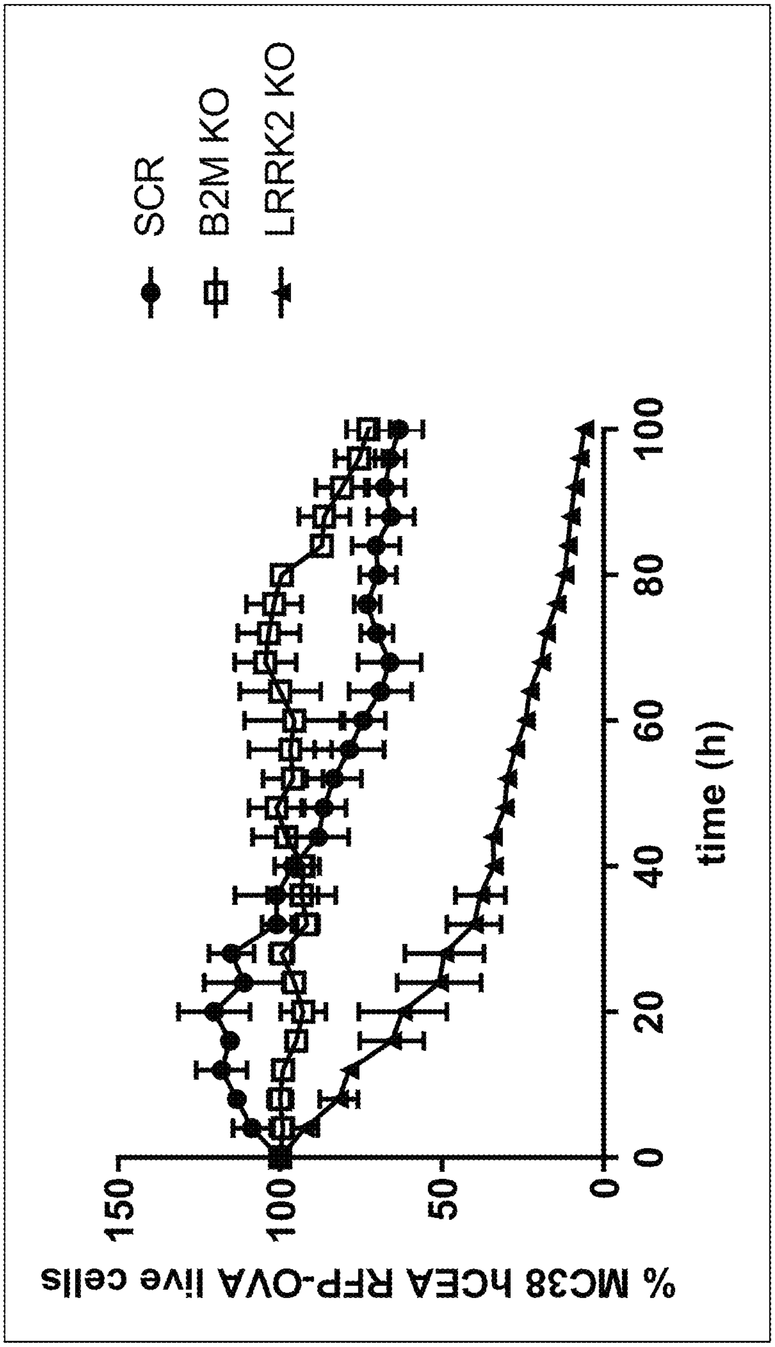
Figure 4B:
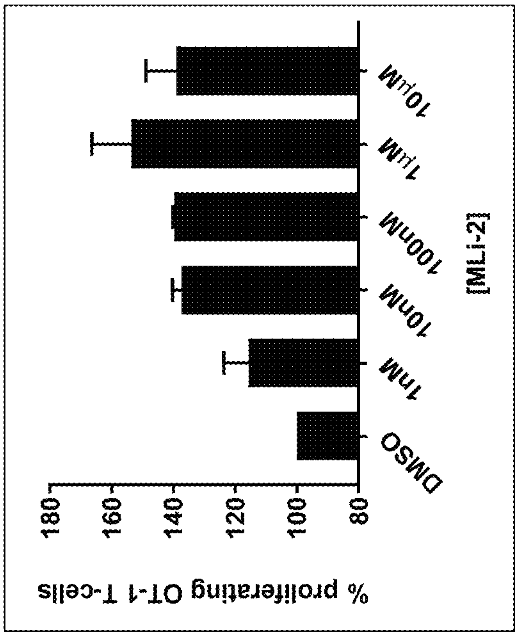
FIG. 4A, FIG. 4B, FIG. 4C, FIG. 4D, FIG. 4E, FIG. 4F, FIG. 4G, FIG. 4H: Effect of LRRK2 inhibitors MLi-2 (FIG. 4A, FIG. 4B), 9605 (FIG. 4C, FIG. 4D), LRRK2-IN-1 (FIG. 4E, FIG. 4F) and 7915 (FIG. G, FIG. H) on antigen cross-presentation and T cell priming.
Figure 4A:
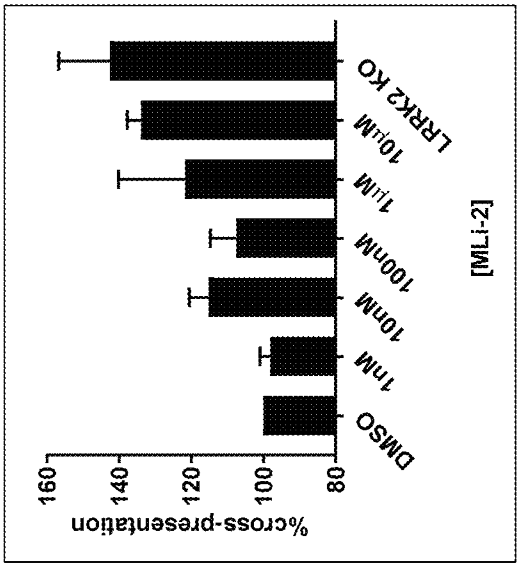
Figure 4C:
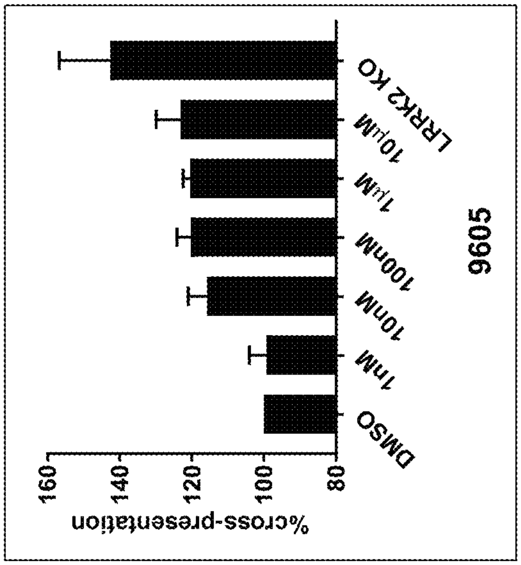
Figure 4D:
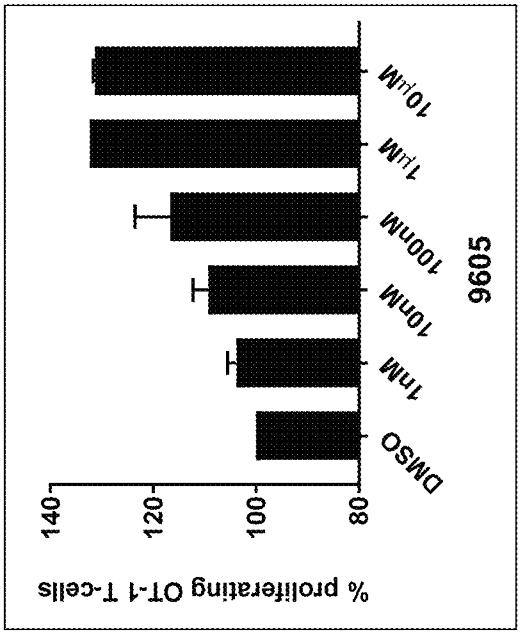
Figure 4F:
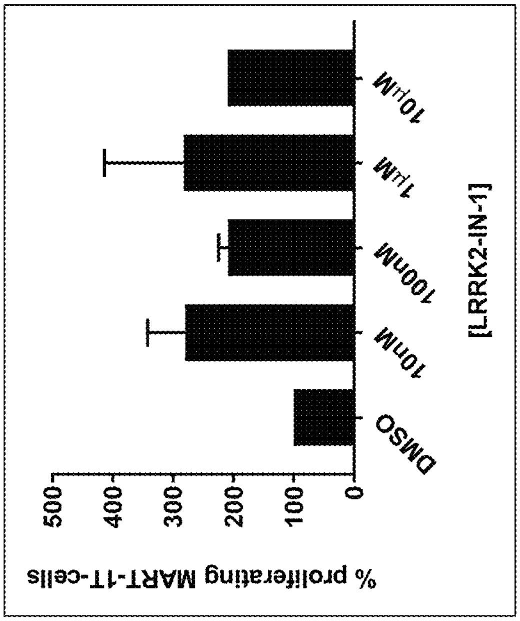
Figure 4E:
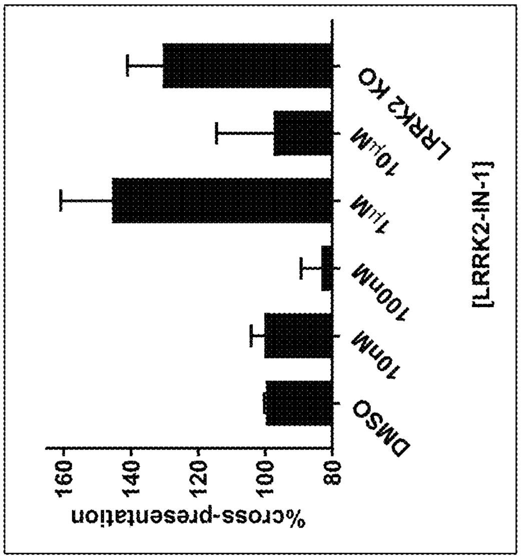
Figure 4G:
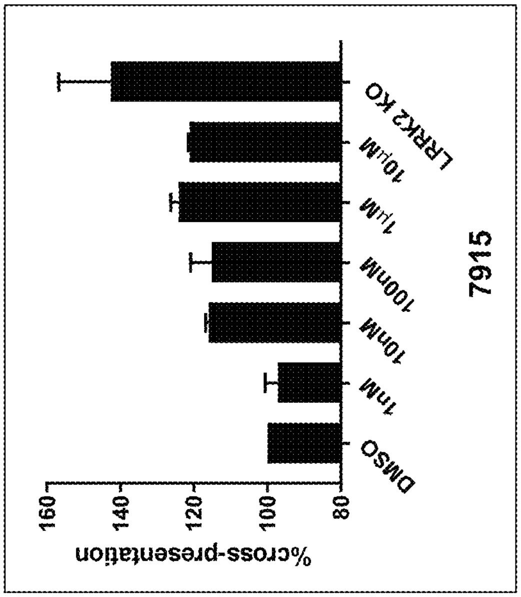
Figure 4H:
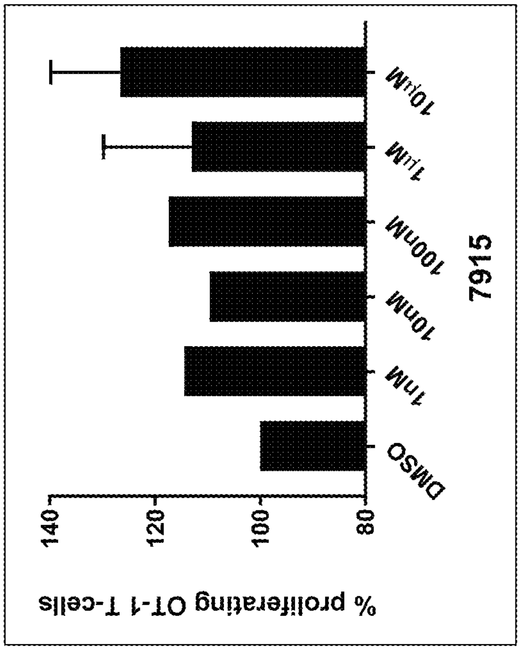
Figure 5A:
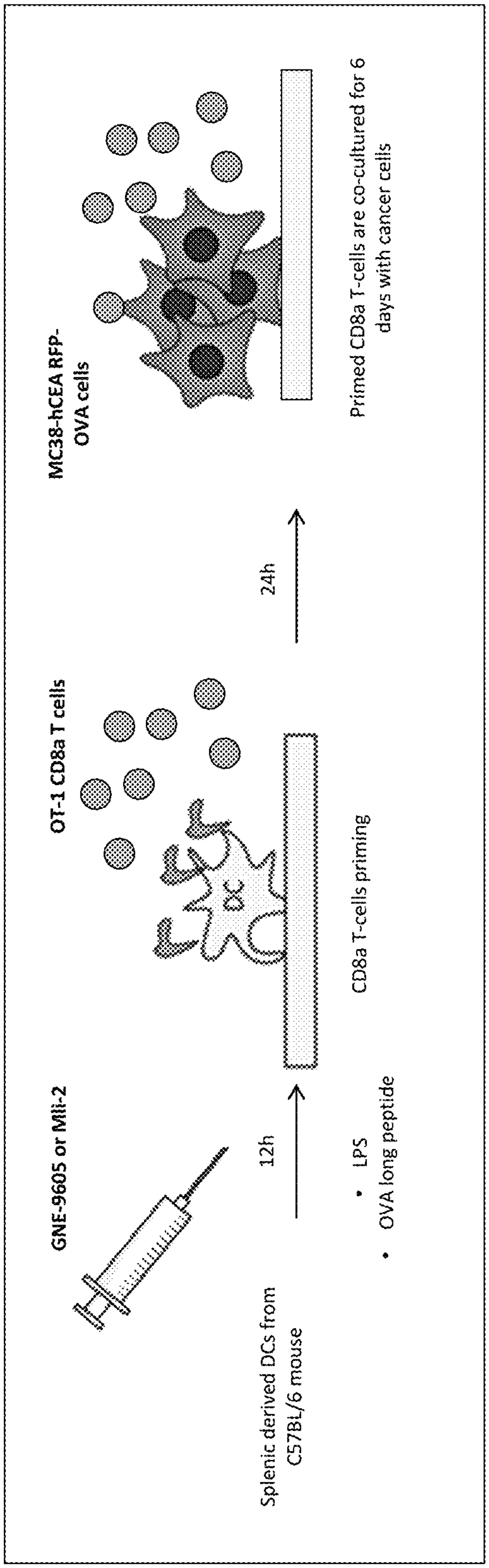
FIG. 5A, FIG. 5E: Effect of the LRRK2 inhibitors 7915, 9605, MLi-2 and LRRK2-IN-1 on T cell mediated cancer cells killing. Schematic representation of the killing assay experimental setup respectively in mouse and human setting.
Figure 5B:
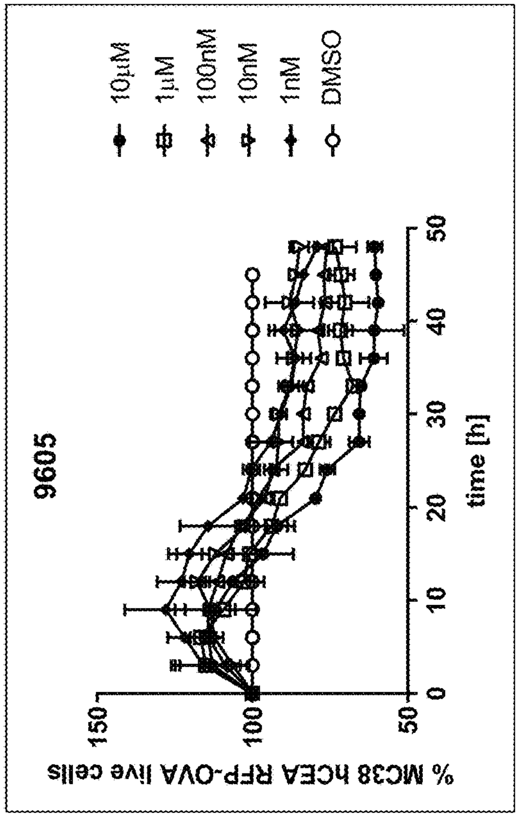
FIG. 5B, FIG. 5C, FIG. 5D) Incucyte based evaluation of T cell cytotoxicity depicted as MC38-RFP-OVA cancer cell viability upon co-cultured with CD8a T cells primed by mouse splenic dendritic cells pre-treated with different LRRK2 inhibitors (B: 9605; C: MLi-2, D: 7915). Data are normalized to DMSO treated dendritic cells co-cultured with CD8a T cells.
Figure 5C:
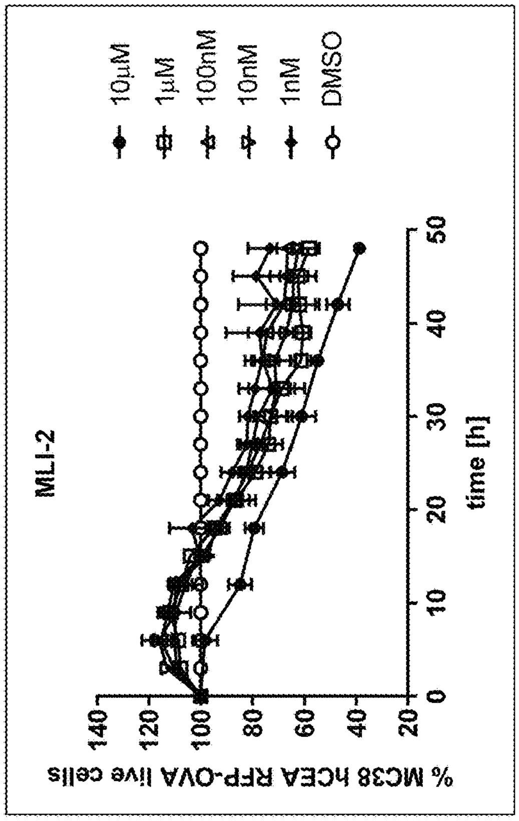
Figure 5D:
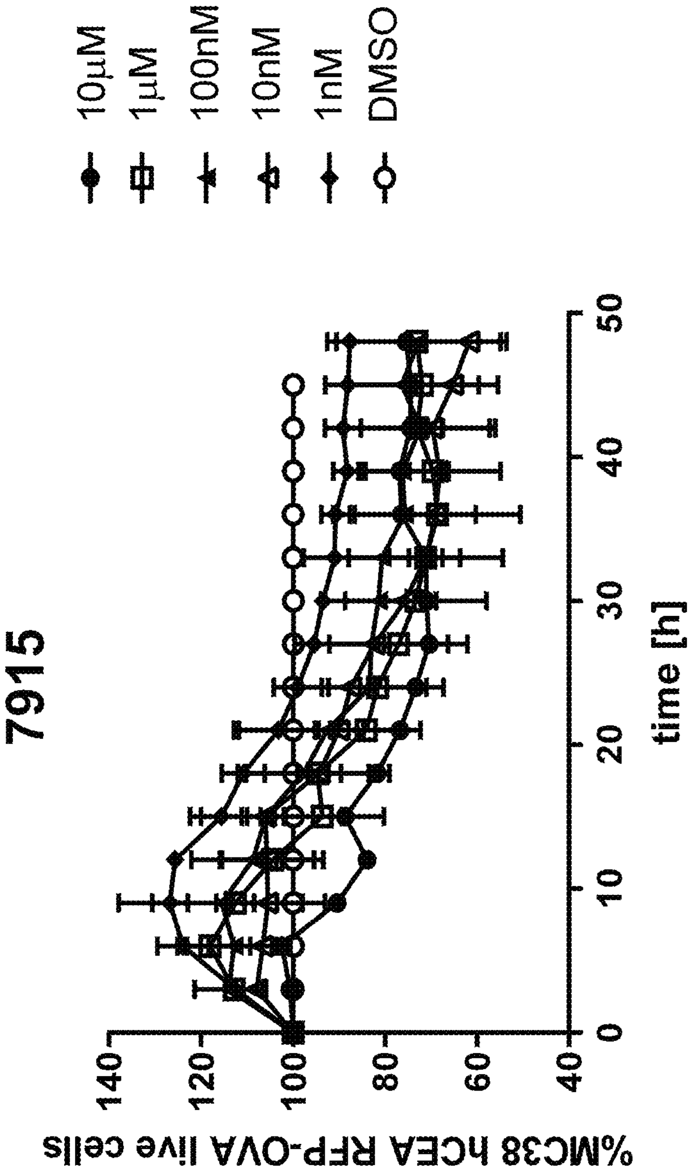
Figure 5E:
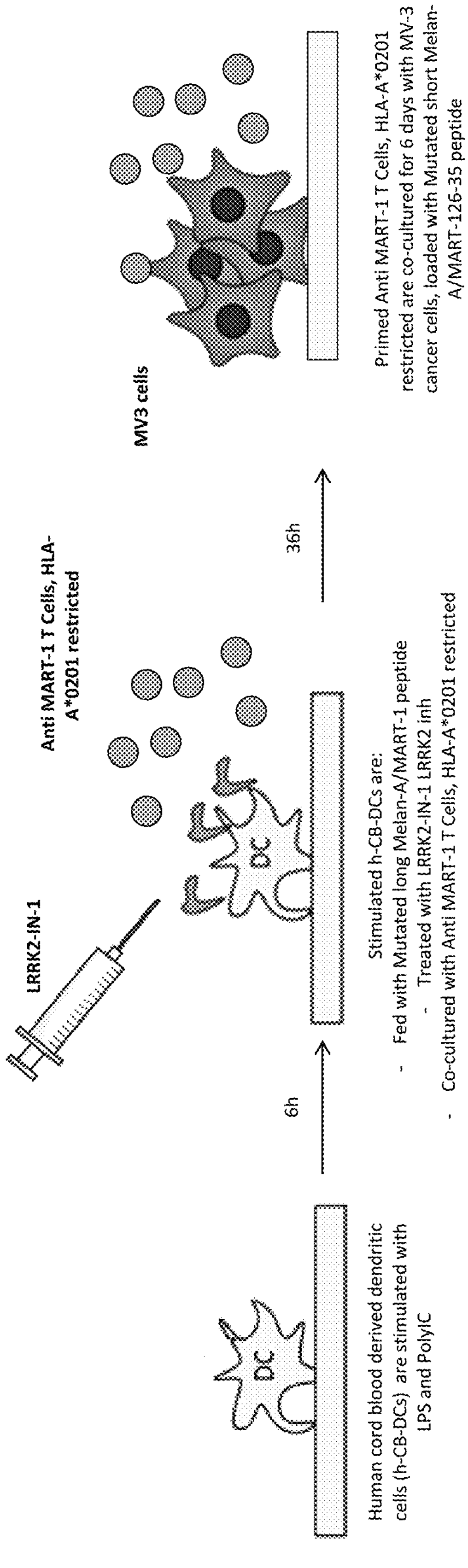
Figure 5F:
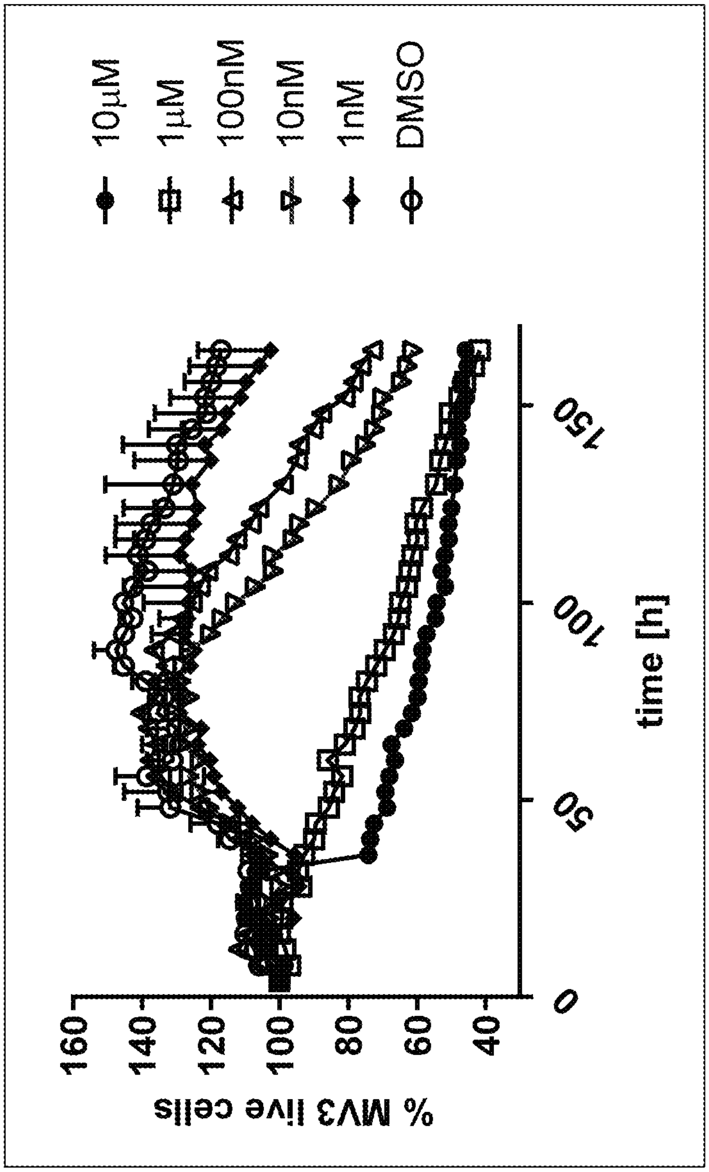
FIG. 5F) Evaluation of MV3 cancer cells viability upon co-cultured with MART-1 T Cells primed by human cord blood derived dendritic cells pre-treated with the LRRK2 inhibitor LRRK2-IN-1. Data are normalized to MV3 cells co-cultured with T cells primed in the absence of MARTI peptide. All the experiments were performed in triplicates.
Figure 6:
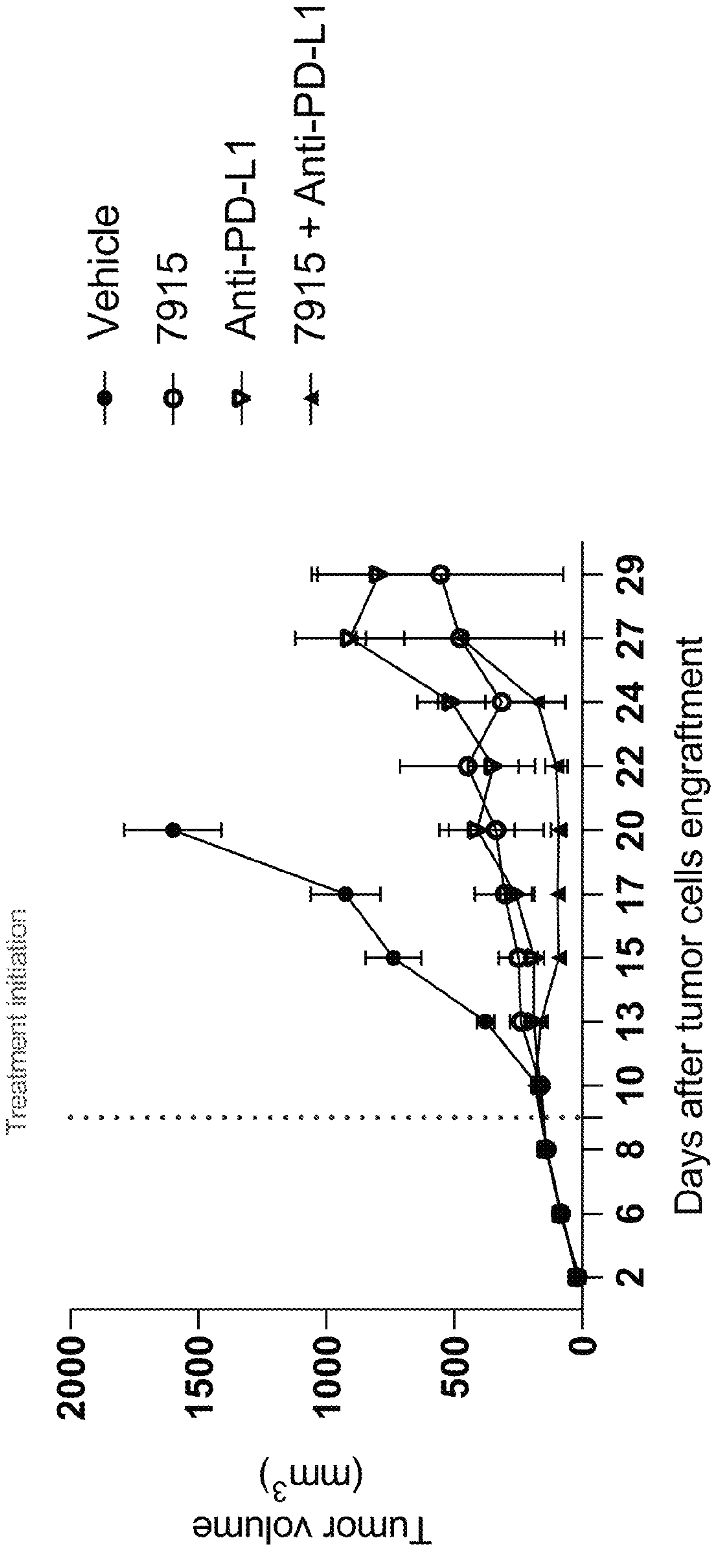
FIG. 6: In vivo efficacy of the LRRK2 inhibitor 7915 in tumor bearing mice. LRRK2 inhibitor 7915 and anti-PD-L1 (clone 6E11, atezolizumab mouse surrogate) alone or in combination significantly decrease MC-38 tumor growth in comparison with vehicle treated mice (with a respective tumor growth inhibition of 82%, 92% and 107%). The average tumor growth from day zero to day 15 is expressed in mm3. Results are expressed as mean+/−SEM. All parameters were analyzed using GraphPad Prism software.

To evaluate changes in antigen cross-presentation upon functional knockout of LRRK2, we generated single knockout DC2.4 cells for LRRK2, B2M (negative control, due to ablation of MHC-I complex on the cell surface) and for a non-targeting sgRNA (DC2.4 SCR). In the first layer of validation, we subjected the knockout cells into the same assay as for the CRISPR/Cas9 screen. In accordance to the screening results, LRRK2 knockouts show an enhanced antigen cross-presentation, evaluated as increased quantity of H2Kb-SIINFEKL complex on DC2.4 cell surface (FIG. 2-A). In parallel, we took advantage of an independent assay to further validate the LRRK2. This assay was based on the evaluation of OT-1 CD8a T cell proliferation upon co-culture with DC2.4 SCR cells or knockout for LRRK2 or B2M genes pulsed with the OVA long peptide (241-270). Consistently with the results generated in the first validation, we demonstrated that OT-1 CD8a T cells proliferate more in a co-culture with DC2.4 knockout for LRRK2 gene than the ones co-cultured with DC2.4 SCR cells. Knockout of B2m limits T cell proliferation to a minimum (FIG. 2-B). The two independent assays successfully cross-validate LRRK2 as a potential enhancer of T cell activation and thus, a potential target for cancer immunotherapy. To further validate the biological relevance of LRRK2 in boosting the T cell mediated anti-cancer immunity, we assessed the cytotoxicity of LRRK2 knockout DC2.4 primed OT-1 CD8a T cells. Briefly, Ova long peptide pulsed DC2.4 SCR cells or knockout for B2M or LRRK2 were used to prime OT-1 CD8a T. Subsequently, the primed OT-1 CD8a T cells were co-cultured with MC38 RFP-OVA cancer cells (FIG. 3-A). Cancer cell viability was analyzed using live cell imaging. In line with the cross-presentation and T cell proliferation results, we observe an enhanced cancer cell killing by OT-1 CD8a T cells primed by DC2.4 LRRK2 knockout in comparison to DC2.4 SCR and DC2.4 B2m knockout primed T cells (FIG. 3-B). Taken together these evidences show that targeting LRRK2 in dendritic cells could represent a therapeutic option to boost the T cells mediated cytotoxicity.

Example 3

Targeting LRRK2: Small Molecule Inhibitors in Primary Human and Murine Dendritic Cells The experimental evidences described in the previous examples demonstrate a potential role of LRRK2 in DC-mediated T cell priming. To further validate the biological role of LRRK2 in the dendritic cells we took advantage of four different LRRK2 inhibitor molecules: 9605, 7915, MLi-2 and LRRK2-IN-1. As for the genetic validation, we tested the effect of overnight administration of MLi-2 (FIG. 4-A), 9605 (FIG. 4-C), LRRK2-IN-1 (FIG. 4-E) and 7915 (FIG. 4-G) in a cross-presentation assay on DC2.4 SCR cells and we used DC2.4 knockout for LRRK2 as positive control. MLi-2 (FIG. 4-A), 9605 (FIG. 4-C) and 7915 (FIG. 4-G) show a dose dependent enhancement of antigen cross-presentation starting from 10 nM. LRRK2-IN-1 shows an effect on antigen cross-presentation at 1 μM (FIG. 4-E). Overall, these results suggested that the kinase activity of LRRK2 is responsible for the immune related phenotype captured in the CRISPR/Cas9 screening. Subsequently, we investigate whether the pre-treatment of freshly isolated mouse splenic dendritic cells with increasing concentrations of the compounds can enhance the OT-1 CD8a T cells activation upon co-culture. The experimental results show dose dependent increase of T cell proliferation. MLi-2 (FIG. 4-B) shows an increased T cell proliferation already at 10 nM while 9605 starts to exert a dose dependent effect at 100 nM (FIG. 4-D). Both LRRK2-IN-1 (FIG. 4-F) and 7915 (FIG. 4-H) show already at lowest concentration a stable increase of cross-presentation mediated T cell proliferation. Also in this case, the two independent assays successfully validate LRRK2 as a potential target to boost dendritic cell cross-presentation capabilities. Finally, as for the genetic validation in DC2.4, we challenge the splenic derived dendritic cells treated with the different compounds in a killing assay were we measured the MC38 RFP-OVA cancer cell viability upon 6 days of co-culture with OT-1 CD8a T cells primed by mouse splenic dendritic cells pre-treated with the two LRRK2 inhibitors (FIG. 5-A). Overtime, OT-1 CD8a T cells killed MC38 RFP-OVA cancer cells in a dose dependent manner proving that, in a mouse setting, LRRK2 inhibition by 9605, MLi-2 and 7915 recapitulates the feature observed in the knockout model and is responsible for the increased T cell mediated cytotoxicity (FIGS. 5-B, C and D, respectively)). Finally, we aimed to translate our findings in a human setting; to do this we utilized human cord blood derived dendritic cells that were pre-treated with LRRK2-IN-1 inhibitor. Accordingly, with the previous data on splenic dendritic cells and with the evidences of LRRK2-IN-1 on DC2.4 enhancement of antigen cross-presentation, we observed that MART-1 T Cells primed by human cord blood derived dendritic cells pre-treated with LRRK2-IN-1 increased the T cells proliferation (FIG. 4-F). To conclude, MART-1 T Cells primed by human cord blood derived dendritic cells pulsed with mutated long Melan-A/MART-1 peptide (EEE-PEG2-HGHSYTTAEELAGIGILT-VILGVLP-PERG2-EEE) and treated with increasing concentration of LRRK2-IN-1 were used in a 6 days killing assay on MV3 cancer cells incubated with mutated short Melan-A/MART-126-35 peptide (ELAGIGILTV) (FIG. 5-D). The experimental results show a dose dependent reduction of MV3 cancer cell viability corroborating the evidences of the genetic model and the pharmacological inhibition in the mouse setting (FIG. 5-E).

To further validate our findings seven different LRRK2 inhibitors were tested for the enhancement of dendritic cell cross-presentation capabilities and in a killing assay where T-cells primed by dendritic cells treated with the different compounds in a concentration range between 1 nM and 10 μM, were co-cultured with cancer cells (FIG. 5-G).

Collectively, our findings suggest that LRRK2 may have an impact in cancer immunotherapy by modulating antigen processing and cross-presentation.

Example 4

In Vivo Effect of Selective LRRK2 Kinase Inhibition on Tumor Growth

Animal Selection and Welfare

The experiment was carried out with 6-8 weeks female C57BL/6 mice from Janvier Labs. All procedures described in this study have been reviewed and approved by the local ethic committee (CELEAG) and validated by the French Ministry of Research. Mice was hosted in TCS BSL-2 facility by groups of 5 individuals. Mice were allowed to acclimate to the environment for 5 days prior to the beginning of the experiment. During the efficacy study, mice were monitored daily for unexpected signs of distress. Body weight was monitored 3 times a week. Mice with a cumulative clinical score or with a body weight loss >25% were sacrificed.

LRRK2 Inhibitor 7915: In Vivo Pharmacology Study Design

Mice were injected subcutaneously with 0.5×106 MC-38 tumor cells in 50% Matrigel. Tumor cell engraftment was defined as day zero. At day 8, mice were randomized into 4 groups of 10 mice each, according to the tumor volume. Treatments were initiated at day 9, when the average tumor volume reached ~150 mm3 as follows:

- Group 1: vehicle, dose 200 μL twice per day per os, twice per week intraperitoneal and intravenously once at day 8
- Group 2: 7915: dose 300 mg/kg per os administration twice per day.
- Group 3: anti PD-L1 (clone 6E11, atezolizumab mouse surrogate): dose 10 mg/kg intravenous injection once at day 8 and dose 5 mg/kg intraperitoneal injection twice per week.
- Group 4: 7915+anti-PD-L1 (clone 6E11, atezolizumab mouse surrogate): dose 300 mg/kg per os injection twice per day. Anti PD-L1: dose 10 mg/kg intravenous injection once at day 8 and dose 5 mg/kg intraperitoneal injection twice per week.

Drug Treatments 7915 (cat. num. HY-18163 from MedChemExpress). LRRK2 inhibitor was administered as free base suspensions in vehicle [1% (w/v) Avicel RC-591 and 0.2% (v/v) polysorbate 80 (Tween 80) in reverse osmosis water].

In Vivo Effect of Selective LRRK2 Kinase Inhibition on Tumor Growth

The aim of this study was to address the in vivo effect on tumor progression of LRRK2 kinase inhibition by using the LRRK2 inhibitor 7915, alone or in combination with anti-PD-L1, in immunocompetent mice engrafted with MC-38 tumor cells. C57BL/6 mice were injected subcutaneously with 0.5×106 MC-38 tumor cells. Tumor cell engraftment was defined as day zero. At day 8, mice were randomized into 4 groups. Treatments were initiated at day 9:

- Group 1: vehicle
- Group 2: 7915
- Group 3: anti PD-L1 (clone 6E11, atezolizumab mouse surrogate)
- Group 4: 7915+anti-PD-L1 (clone 6E11, atezolizumab mouse surrogate)

Tumor growth comparison between the 4 treatments indicated that, compared with Vehicle treated mice, 7915 induced 82% of tumor growth inhibition. When combined with the anti-PD-L1, tumor growth inhibition was increased to 100% but was also associated with more toxicity.

Example 5

In Vivo Effect of Selective LRRK2 Kinase Inhibition on NSG (NOD Scid Gamma Mouse) Tumor Bearing Mice Animal Selection and Welfare The experiment was carried out with 6-8 weeks female NSG mice from Jackson Laboratory. All procedures described in this study have been reviewed and approved by the local ethic committee (CELEAG) and validated by the French Ministry of Research. Mice was hosted in TCS BSL-2 facility by groups of 5 individuals. Mice were allowed to acclimate to the environment for 5 days prior to the beginning of the experiment. During the efficacy study, mice were monitored daily for unexpected signs of distress. Body weight was monitored 3 times a week. Mice with a cumulative clinical score or with a body weight loss >25% were sacrificed.

GNE-7915 LRRK2 Inhibitor: In Vivo Pharmacology Study Design

Mice were injected subcutaneously with 0.5×106 MC-38 tumor cells in 50% Matrigel. Tumor cell engraftment was defined as day zero. At day 9, mice were randomized into 2 groups of 12 mice each, according to the tumor volume. Treatments were initiated at day 10, when the average tumor volume reached ~150 mm3 as follows:

- Group 1: vehicle, dose 200 μL twice per day per os
- Group 2: GNE-7915: dose 300 mg/kg per os administration twice per day.

Drug Treatments

GNE-7915 (cat. num. HY-18163 from MedChemExpress). LRRK2 inhibitor was administered as free base suspensions in vehicle [1% (w/v) Avicel RC-591 and 0.2% (v/v) polysorbate 80 (Tween 80) in reverse osmosis water].

In Vivo Effect of Selective LRRK2 Kinase Inhibition on Tumor Growth

The aim of this study was to address the in vivo effect on tumor progression of LRRK2 kinase inhibition by using the LRRK2 inhibitor GNE-7915, in immuno-deficient mice engrafted with MC-38 tumor cells. NSG mice were injected subcutaneously with 0.5×106 MC-38 tumor cells. Tumor cell engraftment was defined as day zero. At day 9, mice were randomized into 2 groups. Treatments were initiated at day 10:

- Group 1: vehicle
- Group 2: GNE-7915

Figure 7:
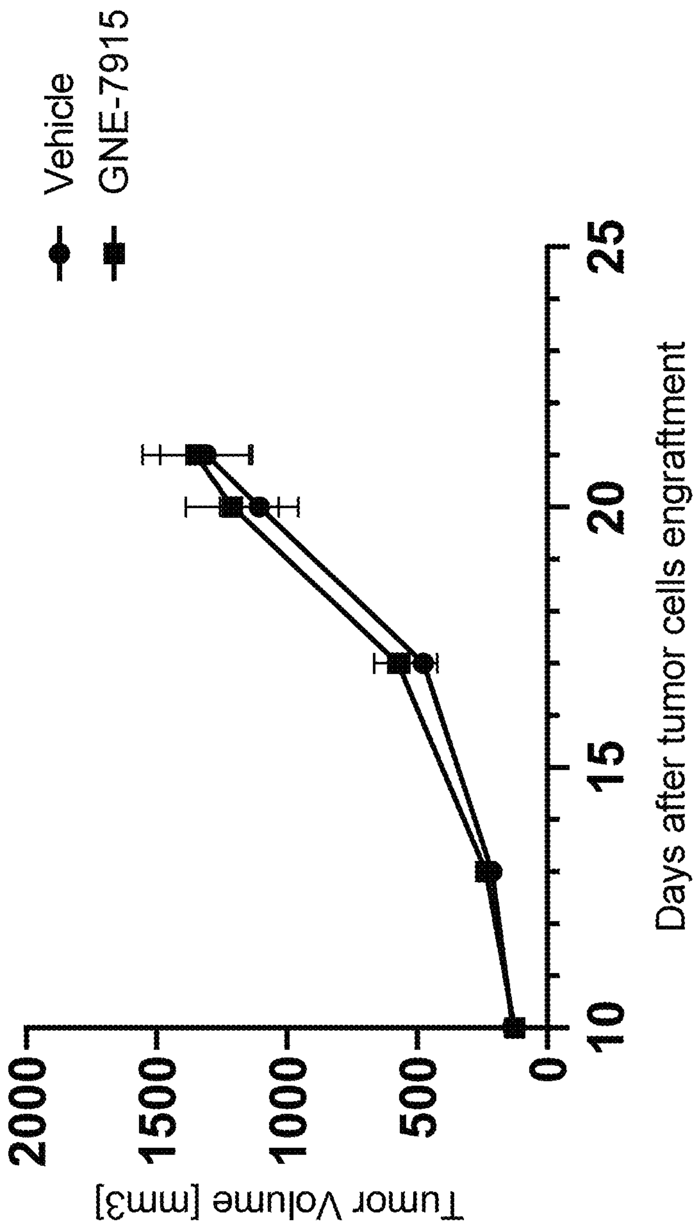
FIG. 7: In vivo efficacy of GNE-7915 on NSG (NOD scid gamma mouse) tumor bearing mice. GNE-7915 is not impacting MC-38 tumor growth in comparison with vehicle treated mice. The average tumor growth from day zero to day 21 is expressed in mm3. Results are expressed as mean +/−SEM. All parameters were analyzed using GraphPad Prism software.

Tumor growth comparison between the 2 treatments indicated that, compared with Vehicle treated mice, GNE-7915 is not modifying tumor growth (FIG. 7).

Example 6

In Vivo Effect of Selective LRRK2 Kinase Inhibition on Tumor Growth

Animal Selection and Welfare

The experiment was carried out with 6-8 weeks female C57BL/6 mice from Janvier Labs. All procedures described in this study have been reviewed and approved by the local ethic committee (CELEAG) and validated by the French Ministry of Research. Mice was hosted in TCS BSL-2 facility by groups of 5 individuals. Mice were allowed to acclimate to the environment for 5 days prior to the beginning of the experiment. During the efficacy study, mice were monitored daily for unexpected signs of distress. Body weight was monitored 3 times a week. Mice with a cumulative clinical score or with a body weight loss >25% were sacrificed.

PFE-360 and Mli-2 LRRK2 Inhibitors: In Vivo Pharmacology Study Design

Mice were injected subcutaneously with 0.5×106 MC-38 tumor cells in 50% Matrigel. Tumor cell engraftment was defined as day zero. At day 8, mice were randomized into 6 groups of 20 mice each, according to the tumor volume. Treatments were initiated at day 9, when the average tumor volume reached ~150 mm3 as follows:

Group 1: vehicle, dose 200 μL twice per day per os, twice per week intraperitoneal and intravenously once at day 8

Group 2: anti PD-L1: dose 10 mg/kg intravenous injection once at day 8 and dose 5 mg/kg intraperitoneal injection twice per week.

Group 3: PFE-360: dose 7.5 mg/kg per os injection twice per day.

Group 4: Mli-2: dose 10 mg/kg per os injection twice per day.

Group 5: PFE-360+anti-PD-L1 PFE-360: dose 7.5 mg/kg per os injection twice per day. Anti PD-L1: dose 10 mg/kg intravenous injection once at day 8 and dose 5 mg/kg intraperitoneal injection twice per week.

Group 6: Mli-2+anti-PD-L1 Mli-2: dose 10 mg/kg per os injection twice per day. Anti PD-L1: dose 10 mg/kg intravenous injection once at day 8 and dose 5 mg/kg intraperitoneal injection twice per week.

Drug Treatments

PFE-360 (cat. num. HY-120085 from MedChemExpress). Mli-2 (cat. num. S9694 from Selleckhem). LRRK2 inhibitors were administered as free base suspensions in vehicle [1% (w/v) Avicel RC-591 and 0.2% (v/v) polysorbate 80 (Tween 80) in reverse osmosis water].

In Vivo Effect of Selective LRRK2 Kinase Inhibition on Tumor Growth

The aim of this study was to address the in vivo effect on tumor progression of LRRK2 kinase inhibition by using the LRRK2 inhibitors PFE-360 and Mli-2, alone or in combination with anti-PD-L1, in immunocompetent mice engrafted with MC-38 tumor cells. C57BL/6 mice were injected subcutaneously with 0.5×106 MC-38 tumor cells. Tumor cell engraftment was defined as day zero. At day 8, mice were randomized into 6 groups. Treatments were initiated at day 9:

Group 1: vehicle

Group 2: anti PD-L1

Group 3: PFE-360

Group 4: Mli-2

Group 5: PFE-360+anti-PD-L1

Group 6: Mli-2+anti-PD-L1

Figure 8A:
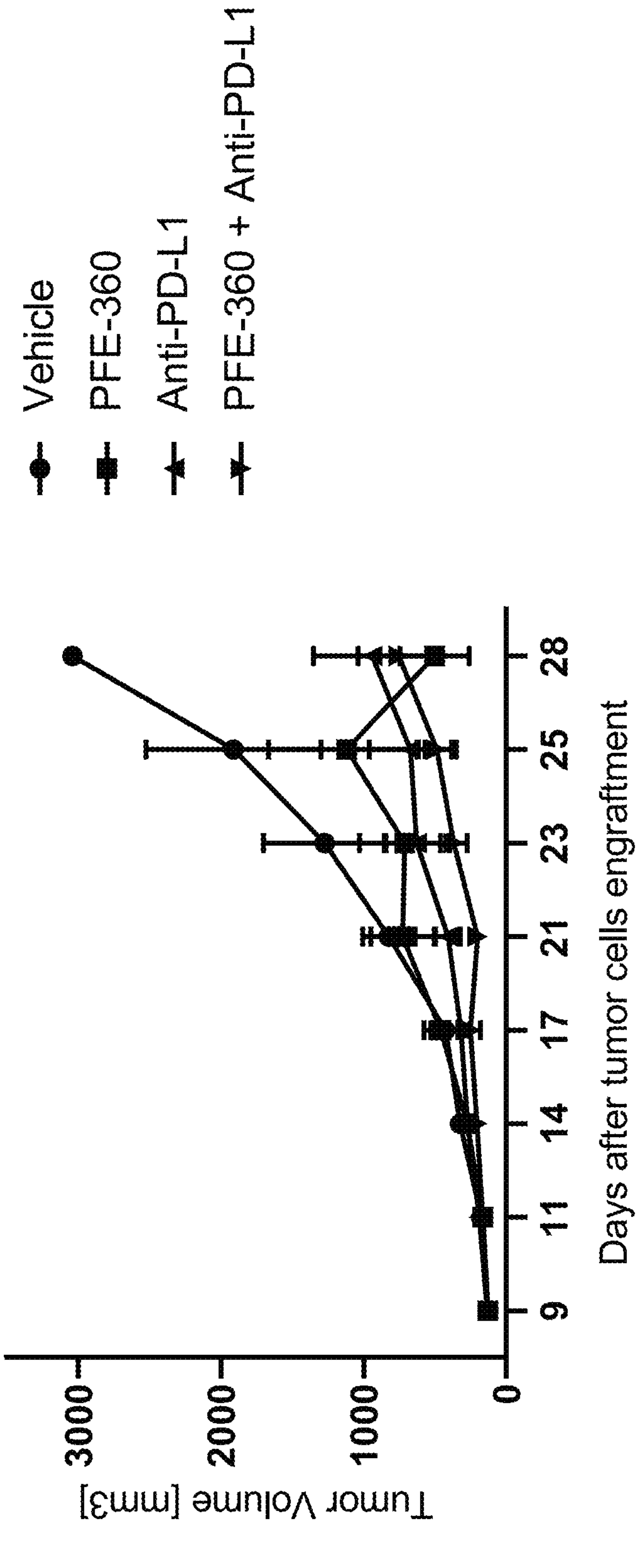
FIG. 8A, FIG. 8B: In vivo efficacy of PFE-360 (FIG. 8A) and Mli-2 (FIG. 8B) LRRK2 inhibitors in immunocompetent tumor bearing mice. PFE-360, Mli-2 and anti-PD-L1 alone or in combination significantly decrease MC-38 tumor growth in comparison with vehicle treated mice. The average tumor growth from day zero to day 28 is expressed in mm3. Results are expressed as mean+/−SEM. All parameters were analyzed using GraphPad Prism software.
Figure 8B:
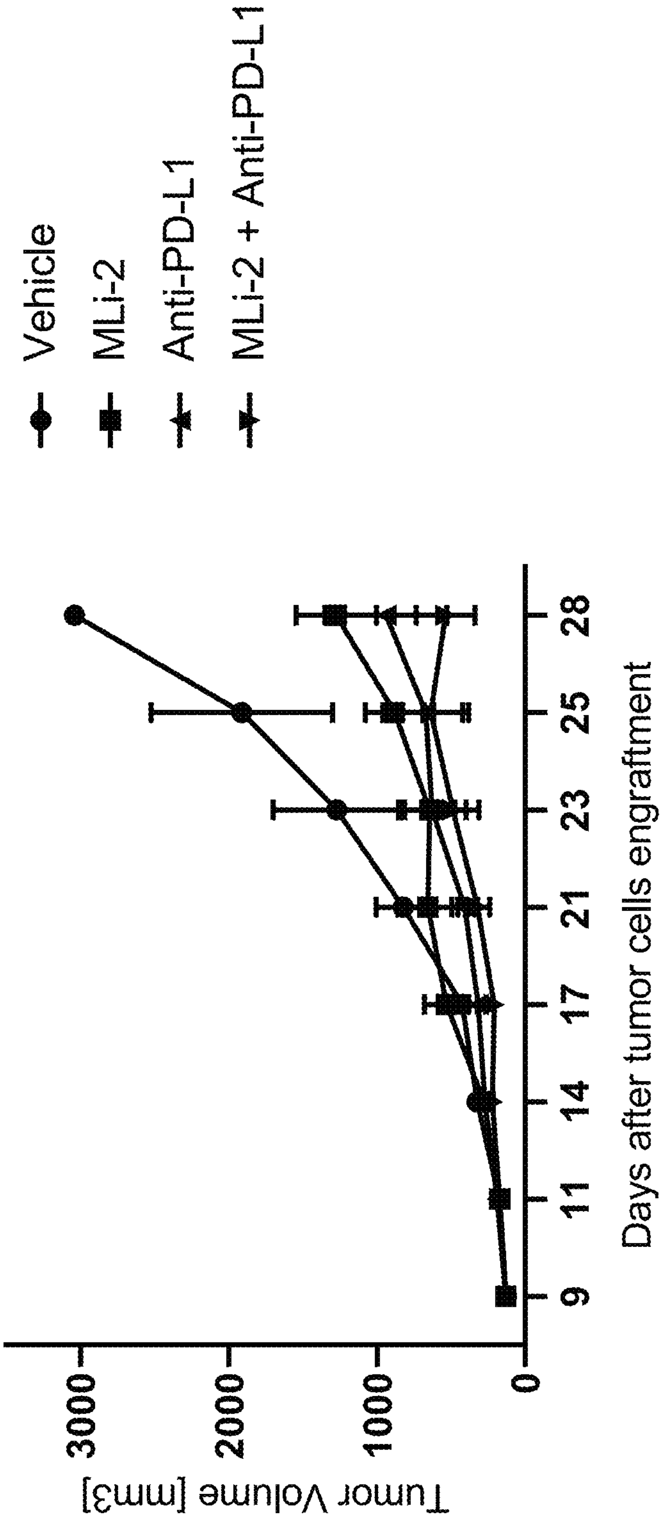

Tumor growth comparison between the 6 treatments indicated that, compared with Vehicle treated mice, the two LRRK2 inhibitors are inducing tumor growth inhibition (FIGS. 8A and B). When combined with the anti-PD-L1, tumor growth inhibition was increased.

Example 7

In Vivo Effect of Selective LRRK2 Kinase Inhibitors PFE-360 and Mli-2 on NSG (NOD Scid Gamma Mouse) Tumor Bearing Mice Animal Selection and Welfare The experiment was carried out with 6-8 weeks female NSG mice from Jackson Laboratory. All procedures described in this study have been reviewed and approved by the local ethic committee (CELEAG) and validated by the French Ministry of Research. Mice was hosted in TCS BSL-2 facility by groups of 5 individuals. Mice were allowed to acclimate to the environment for 5 days prior to the beginning of the experiment. During the efficacy study, mice were monitored daily for unexpected signs of distress. Body weight was monitored 3 times a week. Mice with a cumulative clinical score or with a body weight loss >25% were sacrificed.

PFE-360 and Mli-2 LRRK2 Inhibitor: In Vivo Pharmacology Study Design

Mice were injected subcutaneously with 0.5×106 MC-38 tumor cells in 50% Matrigel. Tumor cell engraftment was defined as day zero. At day 9, mice were randomized into 2 groups of 12 mice each, according to the tumor volume. Treatments were initiated at day 10, when the average tumor volume reached ~150 mm3 as follows:

Group 1: vehicle, dose 200 μL twice per day per os, twice per week intraperitoneal and intravenously once at day 8

Group 2: PFE-360: dose 7.5 mg/kg per os injection twice per day.

Group 3: Mli-2: dose 10 mg/kg per os injection twice per day.

Drug Treatments

PFE-360 (cat. num. HY-120085 from MedChemExpress). Mli-2 (cat. num. 59694 from Selleckhem). LRRK2 inhibitors were administered as free base suspensions in vehicle [1% (w/v) Avicel RC-591 and 0.2% (v/v) polysorbate 80 (Tween 80) in reverse osmosis water].

In Vivo Effect of Selective LRRK2 Kinase Inhibition on Tumor Growth

The aim of this study was to address the in vivo effect on tumor progression of LRRK2 kinase inhibition by using the LRRK2 inhibitors Mli-2 and PFE-360, in immuno-deficient mice engrafted with MC-38 tumor cells. NSG mice were injected subcutaneously with 0.5×106 MC-38 tumor cells. Tumor cell engraftment was defined as day zero. At day 9, mice were randomized into 3 groups. Treatments were initiated at day 10:

Group 1: vehicle

Group 2: PFE-360

Group 3: Mli-2

Figure 9:
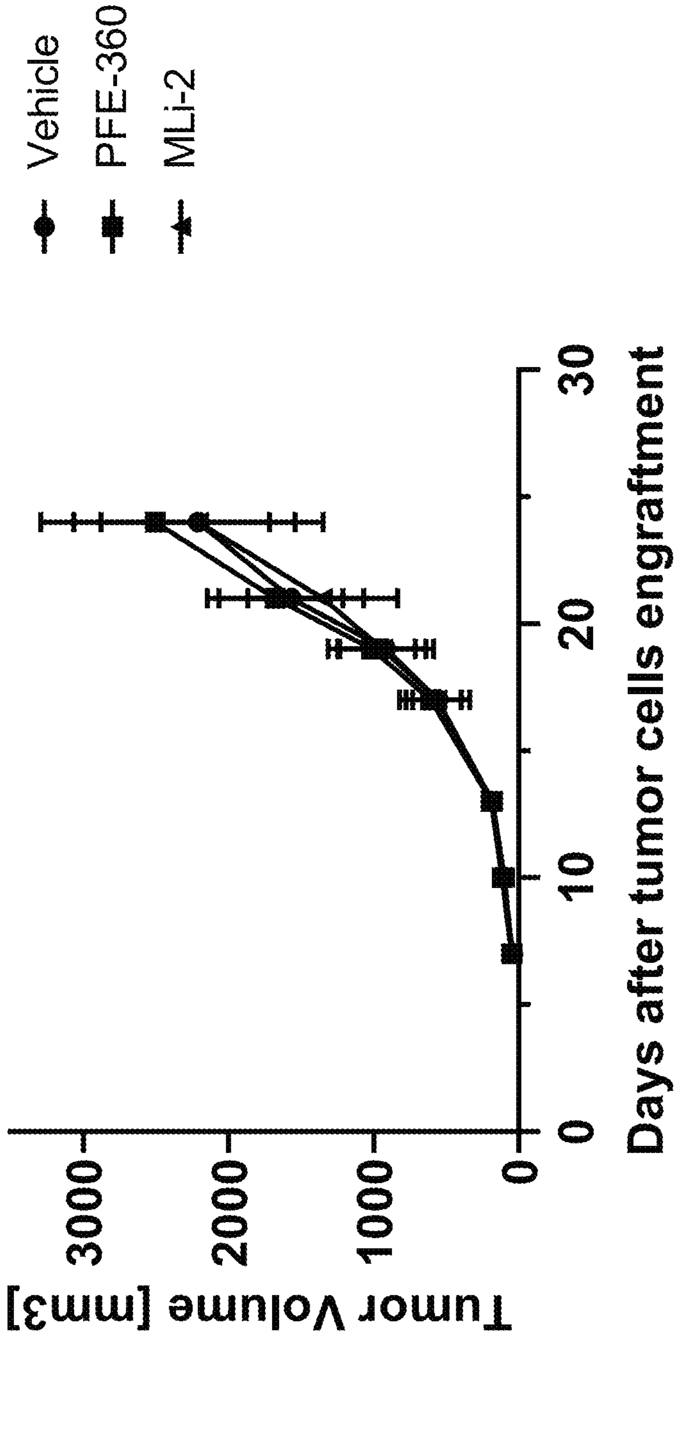

Tumor growth comparison between the 3 treatments indicated that, compared with Vehicle treated mice, PFE-360 and Mli-2 are not modifying tumor growth (FIG. 9).

Example 8

In Vitro Kinase Selectivity Assay

The in vitro kinase selectivity for the tested compounds were determined by running a KINOMEScan® (DiscoverX, CA, USA). Mli2, PFE-360 and, as a reference, the pan-kinase inhibitor sunitinib were tested for their selectivity against 403 non-mutated kinases (Refer to https://www.discoverx-.com/services/drug-discovery-development-services/kinase-profiling/kinomescan for technical and experimental details).

As shown in FIGS. 10A-C and FIG. 11, MLi-2 possess the highest selectivity scores at all three concentrations tested and is 5-fold (S90 at 0.1 μM), 25-fold (S90 at 1 μM) and 20-fold (S90 at 10 μM) more selective than the pan-kinase inhibitor sunitinib. PFE-360 is at all concentration on average 2-fold more selective than sunitinib. For example, Sunitinib at 0.1 μM still inhibits the binding of 14 different kinases by 90% or more whereas MLi-2 and PFE360 show the same effect for three and 9 kinases respectively.

Importantly, the inhibition of LRRK2 at 0.1 uM reduces to less than 50% for sunitinib while MLi-2 and PFE-360 keep their potency in inhibiting LRRK2 at low concentrations (98% and 100%, respectively).

Taking the potency difference into account, the difference in selectivity becomes even more apparent. Sunitinib at a concentration to inhibit >90% LRRK2 (11.1M) inhibits 71 unrelated kinases to >90%. In contrast, PFE-360 and Mli-2 at their lowest concentration to inhibit >90 LRRK2 (0.1 uM) inhibit only 9 and 3 unrelated kinases to >90%, respectively. In conclusion, PFE-360 and Mli-2 are more selective and more potent LRRK2 inhibitors compared to the pan-kinase inhibitor sunitinib.

The selective inhibition of LRRK2 without inhibiting a broad spectrum of unrelated kinases is advantageous and contributes to the synergistic effect of LRRK2 and PD-1 axis binding antagonists as demonstrated herein.

Selectivity scores S(65), S(90) and S (99) in FIG. 11 are calculated as the ratio of number of non-mutated kinases inhibited by 65%, 90 or 99% divided by the total number of non-mutated kinases tested.

Specific References

T. F. Gajewski et al 2014, Nat Immunol, Adaptive immune cells in the tumor microenvironment R. Wallings et al 2015, FEBS J, Cellular processes associated with LRRK2 function and dysfunction L. Berland et al 2019, J Thorac Dis, Current views on tumor mutational burden in patients with non-small cell lung cancer treated by immune checkpoint inhibitors Bjorg J. Waro et al 2018, Brain Behav., Exploring cancer in LRRK2 mutation carriers and idiopathic Parkinson's disease A. Gardet et al 2010, J Immunol, LRRK2 Is Involved in the IFN-γ Response and Host Response to Pathogens M. R. Cookson et al 2015, Curr Neurol Neurosci Rep., LRRK2 Pathways Leading to Neurodegeneration R. L. Wallings et al 2019, Biochem Soc Trans., LRRK2 regulation of immune-pathways and inflammatory disease J. Thevenet et al 2011, PLOS ONE, Regulation of LRRK2 Expression Points to a Functional Role in Human Monocyte Maturation Zhihua Liu et al 2011, Nature Immunology, The kinase LRRK2 is a regulator of the transcription factor NFAT that modulates the severity of inflammatory bowel disease C. J. Gloeckner et al 2009, J Neurochem, The Parkinson disease-associated protein kinase LRRK2 exhibits MAPKKK activity and phosphorylates MKK3/6 and MKK4/7, in vitro An Phu Tran Nguyen et al 2018, Adv Neurobiol, Understanding the GTPase Activity of LRRK2: Regulation, Function, and Neurotoxicity Paetis et al 2009, BioDrugs, Sunitinib: A Multitargeted Receptor Tyrosine Kinase Inhibitor in the Era of Molecular Cancer Therapies Broekman et al 2011, J Clin Oncol, Tyrosine kinase inhibitors: Multi-targeted or single-targeted?

Sequences

Exemplary Anti-PD-1 Antagonist Sequences

| Description | Sequence | Seq ID No |
|---|---|---|
| anti-PD-L1 antibody heavy chain | QVQLVESGGGVVQPGRSLRLDCKASGITFSNSGMHWVRQAP<br>GKGLEWVAVIWYDGSKRYYADSVKGRFTISRDNSKNTLFLQ<br>MNSLRAEDTAVYYCATNDDYWGQGTLVTVSSASTKGPSVFP<br>LAPCSRSTSESTAALGCLVKDYFPEPVTVSWNSGALTSGVHTF<br>PAVLQSSGLYSLSSVVTVPSSSLGTKTYTCNVDHKPSNTKVDK<br>RVESKYGPPCPPCPAPEFLGGPSVFLFPPKPKDTLMISRTPEVT<br>CVVVDVSQEDPEVQFNWYVDGVEVHNAKTKPREEQFNSTYR<br>VVSVLTVLHQDWLNGKEYKCKVSNKGLPSSIEKTISKAKGQP<br>REPQVYTLPPSQEEMTKNQVSLTCLVKGFYPSDIAVEWESNG<br>QPENNYKTTPPVLDSDGSFFLYSRLTVDKSRWQEGNVFSCSV<br>MHEALHNHYTQKSLSLSLGK | 1 |
| anti-PD-L1 antibody light chain | EIVLTQSPATLSLSPGERATLSCRASQSVSSYLAWYQQKPGQA<br>PRLLIYDASNRATGIPARFSGSGSGTDFTLTISSLEPEDFAVYYC<br>QQSSNWPRTFGQGTKVEIKRTVAAPSVFIFPPSDEQLKSGTAS<br>VVCLLNNFYPREAKVQWKVDNALQSGNSQESVTEQDSKDST<br>YSLSSTLTLSKADYEKHKVYACEVTHQGLSSPVTKSFNRGEC | 2 |
| anti-PD-L1 antibody heavy chain | QVQLVQSGVEVKKPGASVKVSCKASGYTFTNYYMYWVRQA<br>PGQGLEWMGGINPSNGGTNFNEKFKNRVTLTTDSSTTTAYME<br>LKSLQFDDTAVYYCARRDYRFDMGFDYWGQGTTVTVSSAST<br>KGPSVFPLAPCSRSTSESTAALGCLVKDYFPEPVTVSWNSGAL<br>TSGVHTFPAVLQSSGLYSLSSVVTVPSSSLGTKTYTCNVDHKP<br>SNTKVDKRVESKYGPPCPPCPAPEFLGGPSVFLFPPKPKDTLMI<br>SRTPEVTCVVVDVSQEDPEVQFNWYVDGVEVHNAKTKPREE<br>QFNSTYRVVSVLTVLHQDWLNGKEYKCKVSNKGLPSSIEKTI<br>SKAKGQPREPQVYTLPPSQEEMTKNQVSLTCLVKGFYPSDIA<br>VEWESNGQPENNYKTTPPVLDSDGSFFLYSRLTVDKSRWQEG<br>NVFSCSVMHEALHNHYTQKSLSLSLGK | 3 |
| anti-PD-L1 antibody light chain | EIVLTQSPATLSLSPGERATLSCRASKGVSTSGYSYLHWYQQK<br>PGQAPRLLIYLASYLESGVPARFSGSGSGTDFTLTISSLEPEDFA<br>VYYCQHSRDLPLTFGGGTKVEIKRTVAAPSVFIFPPSDEQLKS<br>GTASVVCLLNNFYPREAKVQWKVDNALQSGNSQESVTEQDS<br>KDSTYSLSSTLTLSKADYEKHKVYACEVTHQGLSSPVT<br>KSFNRGEC | 4 |
| anti-PD-L1 antibody heavy chain | EVQLVESGGGLVQPGGSLRLSCAASGFTFSDSWIHWVRQAPG<br>KGLEWVAWISPYGGSTYYADSVKGRFTISADTSKNTAYLQM<br>NSLRAEDTAVYYCARRHWPGGFDYWGQGTLVTVSSASTKGP<br>SVFPLAPSSKSTSGGTAALGCLVKDYFPEPVTVSWNSGALTSG<br>VHTFPAVLQSSGLYSLSSVVTVPSSSLGTQTYICNVNHKPSNT<br>KVDKKVEPKSCDKTHTCPPCPAPELLGGPSVFLFPPKPKDTLM<br>ISRTPEVTCVVVDVSHEDPEVKFNWYVDGVEVHNAKTKPREE<br>QYASTYRVVSVLTVLHQDWLNGKEYKCKVSNKALPAPIEKTI<br>SKAKGQPREPQVYTLPPSREEMTKNQVSLTCLVKGFYPSDIAV | 5 |

-continued

| Description | Sequence | Seq ID No |
|---|---|---|
| | EWESNGQPENNYKTTPPVLDSDGSFFLYSKLTVDKSRWQQG NVFSCSVMHEALHNHYTQKSLSLSPG | |
| anti-PD-L1 antibody light chain | DIQMTQSPSSLSASVGDRVTITCRASQDVSTAVAWYQQKPGK APKLLIYSASFLYSGVPSRFSGSGSGTDFTLTISSLQPEDFATYY CQQYLYHPATFGQGTKVEIKRTVAAPSVFIFPPSDEQLKSGTA SVVCLLNNFYPREAKVQWKVDNALQSGNSQESVTEQDSKDS TYSLSSTLTLSKADYEKHKVYACEVTHQGLSSPVTKSFNRGE C | 6 |
| anti-PD-L1 antibody VH | EVQLVESGGGLVQPGGSLRLSCAASGFTFSDSWIHWVRQAPG KGLEWVAWISPYGGSTYYADSVKGRFTISADTSKNTAYLQM NSLRAEDTAVYYCARRHWPGGFDYWGQGTLVTVSS | 7 |
| anti-PD-L1 antibody VH | EVQLVESGGGLVQPGGSLRLSCAASGFTFSDSWIHWVRQAPG KGLEWVAWISPYGGSTYYADSVKGRFTISADTSKNTAYLQM NSLRAEDTAVYYCARRHWPGGFDYWGQGTLVTVSSASTK | 8 |
| anti-PD-L1 antibody VL | DIQMTQSPSSLSASVGDRVTITCRASQDVSTAVAWYQQKPGK APKLLIYSASFLYSGVPSRFSGSGSGTDFTLTISSLQPEDFATYY CQQYLYHPATFGQGTKVEIKR | 9 |
| HVR-H1 | GFTFSDSWIH | 10 |
| HVR-H2 | AWISPYGGSTYYADSVKG | 11 |
| HVR-H3 | RHWPGGFDY | 12 |
| HVR-L1 | RASQDVSTAVA | 13 |
| HVR-L2 | SASFLYS | 14 |
| HVR-L3 | QQYLYHPAT | 15 |
| anti-PDL1 antibody HC-FR1 | EVQLVESGGGLVQPGGSLRLSCAAS | 16 |
| anti-PDL1 antibody HC-FR2 | WVRQAPGKGLEWV | 17 |
| anti-PDL1 antibody HC-FR3 | RFTISADTSKNTAYLQMNSLRAEDTAVYYCAR | 18 |
| anti-PDL1 antibody HC-FR4 | WGQGTLVTVSA | 19 |
| anti-PDL1 antibody HC-FR4 | WGQGTLVTVSS | 20 |
| LC-FR1 | DIQMTQSPSSLSASVGDRVTITC | 21 |
| LC-FR2 | WYQQKPGKAPKLLIY | 22 |
| LC-FR3 | GVPSRFSGSGSGTDFTLTISSLQPEDFATYYC | 23 |
| LC-FR4 | FGQGTKVEIKR | 24 |
| anti-PDL1 antibody VH | EVQLVESGGGLVQPGGSLRLSCAASGFTFSDSWIHWVRQAPG KGLEWVAWISPYGGSTYYADSVKGRFTISADTSKNTAYLQM NSLRAEDTAVYYCARRHWPGGFDYWGQGTLVTVSA | 25 |
| anti-PDL1 antibody VL | DIQMTQSPSSLSASVGDRVTITCRASQDVSTAVAWYQQKPGK APKLLIYSASFLYSGVPSRFSGSGSGTDFTLTISSLQPEDFATYY CQQYLYHPATFGQGTKVEIKR | 26 |
| LRRK2 | MASGSCQGCEEDEETLKKLIVRLNNVQEGKQIETLVQILEDLL VFTYSERASKLFQGKNIHVPLLIVLDSYMRVASVQQVGWSLL CKLIEVCPGTMQSLMGPQDVGNDWEVLGVHQLILKMLTVHN ASVNLSVIGLKTLDLLLTSGKITLLILDEESDIFMLIFDAMHSFP ANDEVQKLGCKALHVLFERVSEEQLTEFVENKDYMILLSALT NFKDEEEIVLHVLHCLHSLAIPCNNVEVLMSGNVRCYNIVVE AMKAFPMSERIQEVSCCLLHRLTLGNFFNILVLNEVHEFVVKA | 27 |

-continued

| Description | Sequence | Seq ID No |
|---|---|---|
| | VQQYPENAALQISALSCLALLTETIFLNQDLEEKNENQENDDE<br>GEEDKLFWLEACYKALTWHRKNKHVQEAACWALNNLLMY<br>QNSLHEKIGDEDGHFPAHREVMLSMLMHSSSKEVFQASANAL<br>STLLEQNVNFRKILLSKGIHLNVLELMQKHIHSPEVAESGCKM<br>LNHLFEGSNTSLDIMAAVVPKILTVMKRHETSLPVQLEALRAI<br>LHFIVPGMPEESREDTEFHHKLNMVKKQCFKNDIHKLVLAAL<br>NRFIGNPGIQKCGLKVISSIVHFPDALEMLSLEGAMDSVLHTL<br>QMYPDDQEIQCLGLSLIGYLITKKNVFIGTGHLLAKILVSSLYR<br>FKDVAEIQTKGFQTILAILKLSASFSKLLVHHSFDLVIFHQMSS<br>NIMEQKDQQFLNLCCKCFAKVAMDDYLKNVMLERACDQNN<br>SIMVECLLLLGADANQAKEGSSLICQVCEKESSPKLVELLLNS<br>GSREQDVRKALTISIGKGDSQIISLLLRRLALDVANNSICLGGF<br>CIGKVEPSWLGPLFPDKTSNLRKQTNIASTLARMVIRYQMKSA<br>VEEGTASGSDGNFSEDVLSKFDEWTFIPDSSMDSVFAQSDDLD<br>SEGSEGSFLVKKKSNSISVGEFYRDAVLQRCSPNLQRHSNSLG<br>PIFDHEDLLKRKRKILSSDDSLRSSKLQSHMRHSDSISSLASER<br>EYITSLDLSANELRDIDALSQKCCISVHLEHLEKLELHQNALTS<br>FPQQLCETLKSLTHLDLHSNKFTSFPSYLLKMSCIANLDVSRN<br>DIGPSVVLDPTVKCPTLKQFNLSYNQLSFVPENLTDVVEKLEQL<br>ILEGNKISGICSPLRLKELKILNLSKNHISSLSENFLEACPKVES<br>FSARMNFLAAMPFLPPSMTILKLSQNKFSCIPEAILNLPHLRSL<br>DMSSNDIQYLPGPAHWKSLNLRELLFSHNQISILDLSEKAYLW<br>SRVEKLHLSHNKLKEIPPEIGCLENLTSLDVSYNLELRSFPNEM<br>GKLSKIWDLPLDELHLNFDFKHIGCKAKDIIRFLQQRLKKAVP<br>YNRMKLMIVGNTGSGKTTLLQQLMKTKKSDLGMQSATVGID<br>VKDWPIQIRDKRKRDLVLNVWDFAGREEFYSTHPHFMTQRA<br>LYLAVYDLSKGQAEVDAMKPWLFNIKARASSSPVILVGTHLD<br>VSDEKQRKACMSKITKELLNKRGFPAIRDYHFVNATEESDAL<br>AKLRKTIINESLNFKIRDQLVVGQLIPDCYVELEKIILSERKNVP<br>IEFPVIDRKRLLQLVRENQLQLDENELPHAVHFLNESGVLLHF<br>QDPALQLSDLYFVEPKWLCKIMAQILTVKVEGCPKHPKGIISR<br>RDVEKFLSKKRKFPKNYMSQYFKLLEKFQIALPIGEEYLLVPSS<br>LSDHRPVIELPHCENSEIIIRLYEMPYFPMGFWSRLINRLLEISP<br>YMLSGRERALRPNRMYWRQGIYLNWSPEAYCLVGSEVLDNH<br>PESFLKITVPSCRKGCILLGQVVDHIDSLMEEWFPGLLEIDICG<br>EGETLLKKWALYSFNDGEEHQKILLDDLMKKAEEGDLLVNP<br>DQPRLTIPISQIAPDLILADLPRNIMLNNDELEFEQAPEFLLGDG<br>SFGSVYRAAYEGEEVAVKIFNKHTSLRLLRQELVVLCHLHHP<br>SLISLLAAGIRPRMLVMELASKGSLDRLLQQDKASLTRTLQHR<br>IALHVADGLRYLHSAMIIYRDLKPHNVLLFTLYPNAAIIAKIAD<br>YGIAQYCCRMGIKTSEGTPGFRAPEVARGNVIYNQQADVYSF<br>GLLLYDILTTGGRIVEGLKFPNEFDELEIQGKLPDPVKEYGCAP<br>WPMVEKLIKQCLKENPQERPTSAQVFDILNSAELVCLTRRILL<br>PKNVIVECMVATHHNSRNASIWLGCGHTDRGQLSFLDLNTEG<br>YTSEEVADSRILCLALVHLPVEKESWIVSGTQSGTLLVINTED<br>GKKRHTLEKMTDSVTCLYCNSFSKQSKQKNFLLVGTADGKL<br>AIFEDKTVKLKGAAPLKILNIGNVSTPLMCLSESTNSTERNVM<br>WGGCGTKIFSFSNDFTIQKLIETRTSQLFSYAAFSDSNIITVVVD<br>TALYIAKQNSPVVEVWDKKTEKLCGLIDCVHFLREVMVKEN<br>KESKHKMSYSGRVKTLCLQKNTALWIGTGGGHILLLDLSTRR<br>LIRVIYNFCNSVRVMMTAQLGSLKNVMLVLGYNRKNTEGTQ<br>KQKEIQSCLTVWDINLPHEVQNLEKHIEVRKELAEKMRRTSV<br>E | |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method for increasing DC-mediated T cell priming in a subject, the method comprising administering a first effective amount of a selective LRRK2 inhibitor and a second effective amount of an anti-PD-L1 antibody, wherein the first effective amount of the selective LRRK2 inhibitor increases DC-mediated T cell priming in the subject, wherein the first effective amount of LRRK2 inhibitor is from about 10 mg/kg to about 300 mg/kg, wherein the selective LRRK2 inhibitor is selected from the group consisting of

[4-[ ] 4-(ethylamino)-5-(trifluoromethyl) pyrimidin-2-yl] amino]-2-fluoro-5-methoxy-phenyl]-morpholino-methanone;

2-methyl-2-[3-methyl-4-[[4-(methylamino)-5-(trifluoromethyl) pyrimidin-2-yllamino] pyrazol-1-yl] propanenitrile;

N2-[5-chloro-1-[3-fluoro-1-(oxetan-3-yl)-4-piperidyl] pyrazol-4-yl]-N4-methyl-5-(trifluoromethyl) pyrimidine-2,4-diamine;

[4-[ ] 5-chloro-4-(methylamino) pyrimidin-2-yl] amino]-3-methoxy-phenyl]-morpholino-methanone;

[4-[ ] 5-chloro-4-(methylamino)-3H-pyrrolo [2,3-d]pyrimidin-2-yl] amino]-3-methoxy-phenyl]-morpholino-methanone;

2-[2-methoxy-4-[4-(4-methylpiperazin-1-yl) piperidine-1-carbonyl] anilino]-5,11-dimethyl-pyrimido [4,5-b][1,4] benzodiazepin-6-one;

3-(4-morpholino-7H-pyrrolo [2,3-d]pyrimidin-5-yl) benzonitrile;

cis-2,6-dimethyl-4-[6-[5-(1-methylcyclopropoxy)-1H-indazol-3-yl] pyrimidin-4-yl] morpholine; and 1-methyl-4-(4-morpholino-7H-pyrrolo [2,3-d]pyrimidin-5-yl) pyrrole-2-carbonitrile;

or a pharmaceutically acceptable salt thereof, and wherein the anti-PD-L1 antibody is atezolizumab.

* * * * *